United States Patent
Fujiwara et al.

(10) Patent No.: US 10,066,253 B2
(45) Date of Patent: Sep. 4, 2018

(54) METHOD OF MEASURING BLOOD COMPONENT AMOUNT

(71) Applicant: PHC Holdings Corporation, Tokyo (JP)

(72) Inventors: Masaki Fujiwara, Ehime (JP); Tomohiro Yamamoto, Ehime (JP)

(73) Assignee: PHC Holdings Corporation, Tokyo (JP)

( * ) Notice: Subject to any disclaimer, the term of this patent is extended or adjusted under 35 U.S.C. 154(b) by 122 days.

(21) Appl. No.: 15/034,725

(22) PCT Filed: Nov. 11, 2014

(86) PCT No.: PCT/JP2014/005666
§ 371 (c)(1),
(2) Date: May 5, 2016

(87) PCT Pub. No.: WO2015/079635
PCT Pub. Date: Jun. 4, 2015

(65) Prior Publication Data
US 2016/0273017 A1 Sep. 22, 2016

(30) Foreign Application Priority Data

Nov. 27, 2013 (JP) ................................ 2013-244987

(51) Int. Cl.
*G01N 27/327* (2006.01)
*C12Q 1/00* (2006.01)
(Continued)

(52) U.S. Cl.
CPC ........... *C12Q 1/006* (2013.01); *G01N 27/307* (2013.01); *G01N 27/3272* (2013.01); *G01N 27/3274* (2013.01); *G01N 27/4166* (2013.01)

(58) Field of Classification Search
CPC ..................... G01N 27/327–27/3274
See application file for complete search history.

(56) References Cited

U.S. PATENT DOCUMENTS 7,955,492 B2 * 6/2011 Fujiwara ............ A61B 5/14546
204/403.03
9,618,517 B2 * 4/2017 MacKintosh .......... G01N 33/66
(Continued)

FOREIGN PATENT DOCUMENTS

CN 1938590 3/2007
EP 1 691 192 8/2006
(Continued)

OTHER PUBLICATIONS

JPO computer-generated English language translation of JP 5239860 B1. Downloaded Dec. 20, 2017. (Year: 2017).*
(Continued)

*Primary Examiner* — Alexander Stephan Noguerola
(74) *Attorney, Agent, or Firm* — Hamre, Schumann, Mueller & Larson, P.C.

(57) ABSTRACT

Provided is a method for measuring a blood component amount that can sufficiently and properly correct the blood component amount by measuring an Hct value with high accuracy and high reliability, and a sensor and a measuring device that are used in the method.
A method for measuring a blood component amount uses a biosensor to calculate a blood component amount in blood. The biosensor includes the following: a first electrode system having a first working electrode and a first counter electrode; a second electrode system having a second working electrode and a second counter electrode; and a reagent portion arranged in a form that covers at least a part of the first electrode system, but does not cover the second working electrode. The method includes the following: a first step of detecting a first current value that flows through the first electrode system and calculating an apparent blood component amount in the blood based on the first current value, during a period in which a first voltage is applied to the first electrode system and a second voltage is applied to the (Continued)

second electrode system while the first voltage is being applied; followed by a second step of stopping the application of the first voltage to the first electrode system, applying a third voltage to the second electrode system, and detecting a second current value; and a step of calculating a true blood component amount using the apparent blood component amount and the second current value.

11 Claims, 41 Drawing Sheets

(51) Int. Cl.
*G01N 27/30* (2006.01)
*G01N 27/416* (2006.01)

(56) References Cited

U.S. PATENT DOCUMENTS

| | | | |
|---|---|---|---|
| 2005/0103624 | A1 | 5/2005 | Bhullar et al. |
| 2006/0175205 | A1 | 8/2006 | Cui et al. |
| 2007/0138026 | A1 | 6/2007 | Fujiwara et al. |
| 2010/0000880 | A1* | 1/2010 | Itoh .................... G01N 27/3274 205/777.5 |
| 2010/0190441 | A1 | 7/2010 | Okuda et al. |
| 2011/0139634 | A1* | 6/2011 | Chou ................. G01N 27/3274 205/792 |
| 2011/0272294 | A1 | 11/2011 | Fujiwara |

FOREIGN PATENT DOCUMENTS

| | | |
|---|---|---|
| JP | 2003-501627 | 1/2003 |
| JP | 3369183 B | 1/2003 |
| JP | 2009-188992 | 8/2009 |
| JP | 5239860 B | 7/2013 |
| WO | 94/29731 | 12/1994 |
| WO | 00/73785 | 12/2000 |
| WO | 2010/087191 | 8/2010 |
| WO | 2012/042211 | 4/2012 |
| WO | 2012/164271 | 12/2012 |

OTHER PUBLICATIONS

Extended European Search Report issued in corresponding European Application No. 14865528.5, dated Nov. 16, 2016, 5 pages.
International Search Report for PCT/JP2014/005666, dated Feb. 10, 2015, 4 pages.
Office Action issued in corresponding Chinese Patent Application No. 201480064988.6, dated Nov. 3, 2017, 19 pages with translation.

* cited by examiner (a)

(b)

(a)

(b)

(a)

(b)

(a)

(b)

(a)

(b)

(a)

(b)

(a)

(b)

(a)

(b)

METHOD OF MEASURING BLOOD COMPONENT AMOUNT

TECHNICAL FIELD

The present invention relates to a method for measuring a blood component amount.

BACKGROUND ART

Sensors for measuring blood components have been conventionally used in, e.g., clinical examinations or self-monitoring of blood glucose levels by diabetics. The sensors for measuring blood components may have a configuration in which a cover is disposed on an insulating substrate via a spacer. A working electrode and a counter electrode are formed on the surface of the insulating substrate. A reagent containing an oxidoreductase, a mediator (electron carrier), etc. is placed on the working electrode and the counter electrode. This portion is an analytical portion. One end of a flow path for the introduction of blood is connected to the analytical portion. The other end of the flow path is open to the outside and serves as a blood inlet. Analysis of blood components (e.g., blood glucose levels) using such a sensor may be performed in the following manner. First, the sensor is set in a special-purpose measuring device (meter). Then, a lancet is used to prick the finger tip or the like and draw a small amount of blood, which is brought into contact with the blood inlet of the sensor. The blood is sucked into the flow path of the sensor by capillary action, passes through the flow path to the analytical portion, and comes into contact with the reagent. An oxidation-reduction reaction occurs between components of the blood and the oxidoreductase, so that a current flows via the mediator. After the current is detected, the measuring device calculates a blood component amount based on the detected current value and displays the blood component amount.

In this manner, the blood component amount can be measured using the sensor. However, the measured value may be affected by hematocrit (Hct). Therefore, in order to obtain an accurately measured value, it is necessary to measure an Hct value and to correct the blood component amount based on the Hct value. For example, there is a sensor that includes two working electrodes and one reference electrode to measure an Hct value and corrects the blood component amount with the Hct value (see Patent Document 1). Moreover, there is a method that uses a mediator to measure an Hct value (see Patent Document 2). However, the conventional techniques have problems in the accuracy and reliability of the measured Hct value, and thus cannot sufficiently and properly correct the blood component amount.

PRIOR ART DOCUMENTS

Patent Documents

Patent Document 1: JP 2003-501627 A
Patent Document 2: Japanese Patent No. 3369183

DISCLOSURE OF INVENTION

Problem to be Solved by the Invention

It is an object of the present invention to provide a method for measuring a blood component amount that can sufficiently and properly correct the blood component amount by reducing the effect of the Hct value.

Means for Solving Problem

The present invention relates to a method for measuring a blood component amount (also referred to as a "first method for measuring a blood component amount" in the present description) that uses a biosensor to calculate a blood component amount in blood. The biosensor includes the following: a first electrode system having a first working electrode and a first counter electrode; a second electrode system having a second working electrode and a second counter electrode; and a reagent portion arranged in a form that covers at least a part of the first electrode system, but does not cover the second working electrode. The method includes the following: a first step of detecting a first current value that flows through the first electrode system and calculating an apparent blood component amount in the blood based on the first current value, during a period in which a first voltage is applied to the first electrode system and a second voltage is applied to the second electrode system while the first voltage is being applied; followed by a second step of stopping the application of the first voltage to the first electrode system, applying a third voltage to the second electrode system, and detecting a second current value; and a step of calculating a true blood component amount using the apparent blood component amount and the second current value.

The present invention relates to a method for measuring a blood component amount (also referred to as a "second method for measuring a blood component amount" in the present description) that uses a biosensor to calculate a blood component amount in blood. The biosensor includes the following: a first electrode system having a first working electrode and a first counter electrode; a second electrode system having a second working electrode and a second counter electrode; and a reagent portion arranged in a form that covers at least a part of the first electrode system. The second counter electrode is located in a place that is independent of the first electrode system, and the reagent portion is also arranged in a form that covers at least a part of the second counter electrode. The method includes the following: a first step of detecting a first current value that flows through the first electrode system and calculating an apparent blood component amount in the blood based on the first current value, during a period in which a first voltage is applied to the first electrode system and a second voltage is applied to the second electrode system while the first voltage is being applied; followed by a second step of stopping the application of the first voltage to the first electrode system, applying a third voltage to the second electrode system, and detecting a second current value; and a step of calculating a true blood component amount using the apparent blood component amount and the second current value.

Effects of the Invention

As described above, the present invention is characterized by the method for measuring a blood component amount. The blood component amount is measured by (i) arranging the reagent portion in a form that covers at least a part of the first electrode system, but does not cover the working electrode of the second electrode system, (ii) applying a voltage to the first electrode system and the second electrode system simultaneously to determine an apparent blood component amount, (iii) applying a voltage only to the second electrode system to determine a current value, and (iv) calculating a true blood component amount by correcting the apparent blood component amount based on the current value (the first method for measuring a blood component amount). Alternatively, the blood component amount is measured by (i) using a biosensor in which the second counter electrode is located in a place that is independent of the first electrode system, and the reagent portion is also arranged in a form that covers at least a part of the second counter electrode, (ii) applying a voltage to the first electrode system and the second electrode system simultaneously to determine an apparent blood component amount, (iii) applying a voltage only to the second electrode system to determine a current value, and (iv) calculating a true blood component amount by correcting the apparent blood component amount based on the current value (the second method for measuring a blood component amount). In these measuring methods, the simultaneous application of a voltage to the first electrode system and the second electrode system reduces the effect of hematocrit on the current value that flows through the first electrode system, and thus improves the accuracy of the apparent blood component amount. Since such an apparent blood component amount is corrected to calculate a true blood component amount, the correction value is small. Therefore, the measuring methods of the present invention reduce the effect of Hct when the blood component amount is measured, and thus improve the accuracy of the measured blood component amount. In the present description, when a reference is made to the "method for measuring a blood component amount", it refers to both the "first method for measuring a blood component amount" and the "second method for measuring a blood component amount".

BRIEF DESCRIPTION OF DRAWINGS

FIG. 7(a) is a graph showing changes in a response current value (mV) over time with respect to an applied voltage (mV) in Comparative Example 1. FIG. 7(b) is a graph showing changes in a sensitivity difference (%) over time with respect to an applied voltage (mV) in Comparative Example 1.

FIG. 8(a) is a graph showing changes in a response current value (mV) over time with respect to an applied voltage (mV) in Example 2. FIG. 8(b) is a graph showing changes in a sensitivity difference (%) over time with respect to an applied voltage (mV) in Example 2.

FIG. 9(a) is a graph showing changes in a response current value (mV) over time with respect to an applied voltage (mV) in Example 3. FIG. 9(b) is a graph showing changes in a sensitivity difference (%) over time with respect to an applied voltage (mV) in Example 3.

FIG. 10(a) is a graph showing changes in a response current value (mV) over time with respect to an applied voltage (mV) in Comparative Example 1. FIG. 10(b) is a graph showing changes in a sensitivity difference (%) over time with respect to an applied voltage (mV) in Comparative Example 1.

FIG. 11(a) is a graph showing changes in a response current value (mV) over time with respect to an applied voltage (mV) in Example 2. FIG. 11(b) is a graph showing changes in a sensitivity difference (%) over time with respect to an applied voltage (mV) in Example 2.

FIG. 12(a) is a graph showing changes in a response current value (mV) over time with respect to an applied voltage (mV) in Example 3. FIG. 12(b) is a graph showing changes in a sensitivity difference (%) over time with respect to an applied voltage (mV) in Example 3.

FIG. 13(a) is a graph showing changes in a response current value (mV) over time with respect to an applied voltage (mV) in Comparative Example 1. FIG. 13(b) is a graph showing changes in a sensitivity difference (%) over time with respect to an applied voltage (mV) in Comparative Example 1.

FIG. 14(a) is a graph showing changes in a response current value (mV) over time with respect to an applied voltage (mV) in Example 2. FIG. 14(b) is a graph showing changes in a sensitivity difference (%) over time with respect to an applied voltage (mV) in Example 2.

FIG. 15(a) is a graph showing changes in a response current value (mV) over time with respect to an applied voltage (mV) in Example 3. FIG. 15(b) is a graph showing changes in a sensitivity difference (%) over time with respect to an applied voltage (mV) in Example 3.

FIG. 16(a) is a graph showing the relationship between an application time and an applied current. FIG. 16(b) is a graph showing changes in a blood component (glucose) concentration and a response current value (mV) over time when the application time is 5 seconds in Comparative Example 1. FIG. 16(c) is a graph showing a blood component (glucose) concentration and a sensitivity difference (%) when the application time is 5 seconds in Comparative Example 1.

FIG. 17(a) is a graph showing the relationship between an application time and an applied current. FIG. 17(b) is a graph showing changes in a blood component (glucose) concentration and a response current value (mV) over time when the application time is 5 seconds in Example 2. FIG. 17(c) is a graph showing a blood component (glucose) concentration and a sensitivity difference (%) when the application time is 5 seconds in Example 2.

FIG. 18(a) is a graph showing the relationship between an application time and an applied current. FIG. 18(b) is a graph showing changes in a blood component (glucose) concentration and a response current value (mV) over time when the application time is 5 seconds in Example 3. FIG. 18(c) is a graph showing a blood component (glucose) concentration and a sensitivity difference (%) when the application time is 5 seconds in Example 3.

FIG. 20(a) is a graph showing the relationship between an application time and an applied current. FIG. 20(b) is a graph showing changes in a response current value (mV) over time with respect to an applied voltage (mV) in Example 4. FIG. 20(c) is a graph showing changes in a sensitivity difference (%) over time with respect to an applied voltage (mV) in Example 4.

FIG. 21(a) is a graph showing the relationship between an application time and an applied current. FIG. 21(b) is a graph showing changes in a response current value (mV) over time with respect to an applied voltage (mV) in Example 4. FIG. 21(c) is a graph showing changes in a sensitivity difference (%) over time with respect to an applied voltage (mV) in Example 4.

FIG. 22(a) is a graph showing the relationship between an application time and an applied current. FIG. 22(b) is a graph showing changes in a response current value (mV) over time with respect to an applied voltage (mV) in Example 4. FIG. 22(c) is a graph showing changes in a sensitivity difference (%) over time with respect to an applied voltage (mV) in Example 4.

FIG. 23(a) is a graph showing the relationship between an application time and an applied current. FIG. 23(b) is a graph showing changes in a blood component (glucose) concentration and a response current value (mV) over time when the application time is 5 seconds in Example 4. FIG. 23(c) is a graph showing a blood component (glucose) concentration and a sensitivity difference (%) when the application time is 5 seconds in Example 4.

FIG. 25(a) is a graph showing the relationship between an application time and an applied current in Example 5. FIG. 25(b) is a graph showing changes in a response current value (mV) over time with respect to an applied voltage (mV) in Example 5. FIG. 25(c) is a graph showing changes in a sensitivity difference (%) over time with respect to an applied voltage (mV) in Example 5.

FIG. 26(a) is a graph showing the relationship between an application time and an applied current in Example 6. FIG. 26(b) is a graph showing changes in a response current value (mV) over time with respect to an applied voltage (mV) in Example 6. FIG. 26(c) is a graph showing changes in a sensitivity difference (%) over time with respect to an applied voltage (mV) in Example 6.

FIG. 27(a) is a graph showing the relationship between an application time and an applied current in Example 5. FIG. 27(b) is a graph showing changes in a response current value (mV) over time with respect to an applied voltage (mV) in Example 5. FIG. 27(c) is a graph showing changes in a sensitivity difference (%) over time with respect to an applied voltage (mV) in Example 5.

FIG. 28(a) is a graph showing the relationship between an application time and an applied current in Example 6. FIG. 28(b) is a graph showing changes in a response current value (mV) over time with respect to an applied voltage (mV) in Example 6. FIG. 28(c) is a graph showing changes in a sensitivity difference (%) over time with respect to an applied voltage (mV) in Example 6.

FIG. 29(a) is a graph showing the relationship between an application time and an applied current in Example 5. FIG. 29(b) is a graph showing changes in a response current value (mV) over time with respect to an applied voltage (mV) in Example 5. FIG. 29(c) is a graph showing changes in a sensitivity difference (%) over time with respect to an applied voltage (mV) in Example 5.

FIG. 30(a) is a graph showing the relationship between an application time and an applied current in Example 6. FIG. 30(b) is a graph showing changes in a response current value (mV) over time with respect to an applied voltage (mV) in Example 6. FIG. 30(c) is a graph showing changes in a sensitivity difference (%) over time with respect to an applied voltage (mV) in Example 6.

FIG. 31(a) is a graph showing the relationship between an application time and an applied current in Example 5. FIG. 31(b) is a graph showing changes in a response current value (mV) over time with respect to an applied voltage (mV) in Example 5. FIG. 31(c) is a graph showing changes in a sensitivity difference (%) over time with respect to an applied voltage (mV) in Example 5.

FIG. 32(a) is a graph showing the relationship between an application time and an applied current in Comparative Example 1. FIG. 32(b) is a graph showing changes in a response current value (mV) over time with respect to an applied voltage (mV) in Comparative Example 1. FIG. 32(c) is a graph showing changes in a sensitivity difference (%) over time with respect to an applied voltage (mV) in Comparative Example 1.

FIG. 33(a) is a graph showing the relationship between an application time and an applied current. FIG. 33(b) is a graph showing changes in a blood component (glucose) concentration and a response current value (mV) over time when the application time is 5 seconds in Example 5. FIG. 33(c) is a graph showing a blood component (glucose) concentration and a sensitivity difference (%) when the application time is 5 seconds in Example 5.

FIG. 34(a) is a graph showing the relationship between an application time and an applied current. FIG. 34(b) is a graph showing changes in a blood component (glucose) concentration and a response current value (mV)

over time when the application time is 5 seconds in Example 6. FIG. 34(c) is a graph showing a blood component (glucose) concentration and a sensitivity difference (%) when the application time is 5 seconds in Example 6.

FIG. 38(a) is a graph showing the relationship between an application time and an applied current in Comparative Example 2. FIG. 38(b) is a graph showing changes in a response current value (mV) over time with respect to an applied voltage (mV) in Comparative Example 2. FIG. 38(c) is a graph showing changes in a sensitivity difference (%) over time with respect to an applied voltage (mV) in Comparative Example 2.

FIG. 39(a) is a graph showing the relationship between an application time and an applied current in Example 8. FIG. 39(b) is a graph showing changes in a response current value (mV) over time with respect to an applied voltage (mV) in Example 8. FIG. 39(c) is a graph showing changes in a sensitivity difference (%) over time with respect to an applied voltage (mV) in Example 8.

FIG. 40(a) is a graph showing the relationship between an application time and an applied current in Example 9. FIG. 40(b) is a graph showing changes in a response current value (mV) over time with respect to an applied voltage (mV) in Example 9. FIG. 40(c) is a graph showing changes in a sensitivity difference (%) over time with respect to an applied voltage (mV) in Example 9.

FIG. 41(a) is a graph showing the relationship between an application time and an applied current. FIG. 41(b) is a graph showing changes in a blood component (glucose) concentration and a response current value (mV) over time when the application time is 5 seconds in Comparative Example 2. FIG. 41(c) is a graph showing a blood component (glucose) concentration and a sensitivity difference (%) when the application time is 5 seconds in Comparative Example 2.

FIG. 42(a) is a graph showing the relationship between an application time and an applied current. FIG. 42(b) is a graph showing changes in a blood component (glucose) concentration and a response current value (mV) over time when the application time is 5 seconds in Example 8. FIG. 42(c) is a graph showing a blood component (glucose) concentration and a sensitivity difference (%) when the application time is 5 seconds in Example 8.

FIG. 43(a) is a graph showing the relationship between an application time and an applied current. FIG. 43(b) is a graph showing changes in a blood component (glucose) concentration and a response current value (mV) over time when the application time is 5 seconds in Example 9. FIG. 43(c) is a graph showing a blood component (glucose) concentration and a sensitivity difference (%) when the application time is 5 seconds in Example 9.

DESCRIPTION OF THE INVENTION

Figure 1:
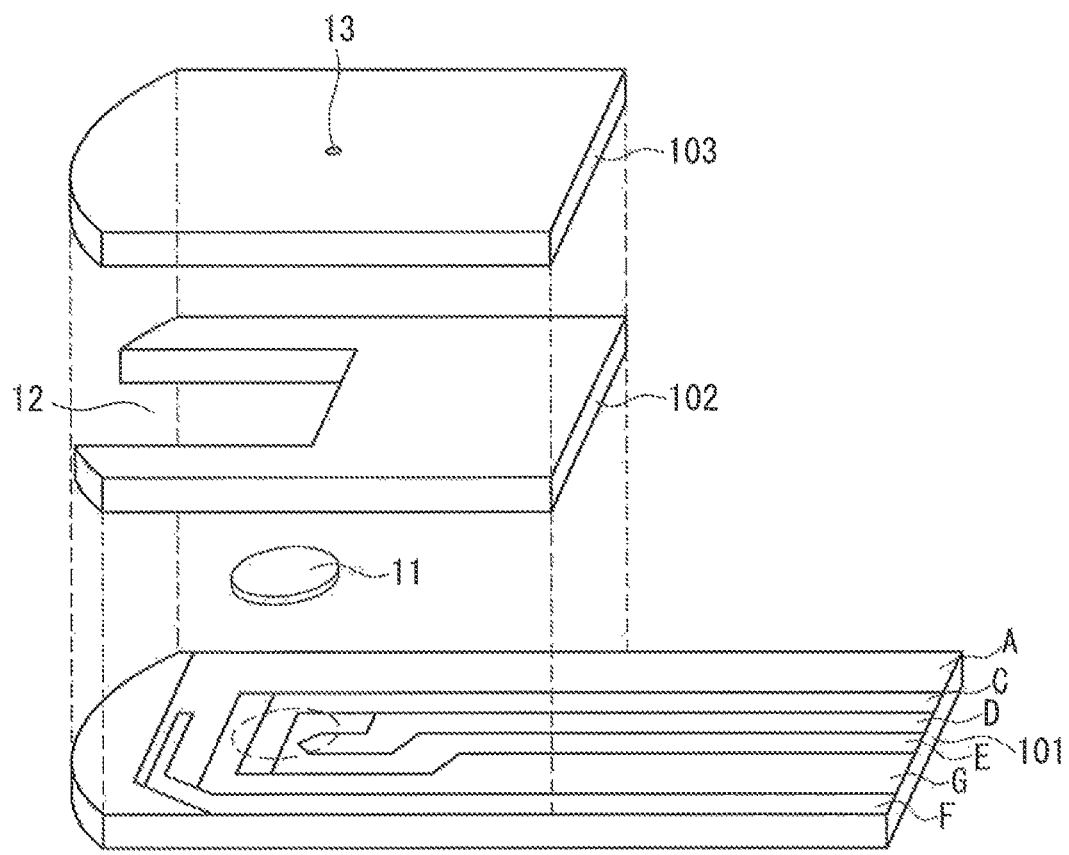
FIG. 1 is an exploded perspective view showing an example of a sensor of the present invention.

Next, the present invention will be described in detail.

The present invention relates to a method for measuring a blood component amount (a first method for measuring a blood component amount) that uses a biosensor to calculate a blood component amount in blood. The biosensor includes the following: a first electrode system having a first working electrode and a first counter electrode; a second electrode system having a second working electrode and a second counter electrode; and a reagent portion arranged in a form that covers at least a part of the first electrode system, but does not cover the second working electrode. The method includes the following: a first step of detecting a first current value that flows through the first electrode system and calculating an apparent blood component amount in the blood based on the first current value, during a period in which a first voltage is applied to the first electrode system and a second voltage is applied to the second electrode system while the first voltage is being applied; followed by a second step of stopping the application of the first voltage to the first electrode system, applying a third voltage to the second electrode system, and detecting a second current value; and a step of calculating a true blood component amount using the apparent blood component amount and the second current value.

The present invention relates to a method for measuring a blood component amount (a second method for measuring a blood component amount) that uses a biosensor to calculate a blood component amount in blood. The biosensor includes the following: a first electrode system having a first working electrode and a first counter electrode; a second electrode system having a second working electrode and a second counter electrode; and a reagent portion arranged in a form that covers at least a part of the first electrode system. The second counter electrode is located in a place that is independent of the first electrode system, and the reagent portion is also arranged in a form that covers at least a part of the second counter electrode. The method includes the following: a first step of detecting a first current value that flows through the first electrode system and calculating an apparent blood component amount in the blood based on the first current value, during a period in which a first voltage is applied to the first electrode system and a second voltage is applied to the second electrode system while the first voltage is being applied; followed by a second step of stopping the application of the first voltage to the first electrode system, applying a third voltage to the second electrode system, and detecting a second current value; and a step of calculating a true blood component amount using the apparent blood component amount and the second current value.

In the second method for measuring a blood component amount, the biosensor may further include a third electrode system having a third working electrode and a third counter electrode. The third working electrode may also be used as the second working electrode, and the third counter electrode may be located in a place that is independent of the first electrode system and the second electrode system.

In the first method for measuring a blood component amount and the second method for measuring a blood component amount, the second voltage and the third voltage may be either the same or different.

In the first method for measuring a blood component amount and the second method for measuring a blood component amount, the first current value that flows through the first electrode system may be detected during the period in which the first voltage is applied to the first electrode system and the second voltage is applied to the second electrode system while the first voltage is being applied. It is preferable that the first current value is detected at the end of the period in which the first voltage is applied to the first electrode system and the second voltage is applied to the second electrode system while the first voltage is being applied.

In the first method for measuring a blood component amount and the second method for measuring a blood component amount, it is preferable that the biosensor further includes a third electrode system having a third working electrode and a third counter electrode, that the reagent portion is arranged in a form that covers at least a part of the third counter electrode, but does not cover the third working electrode, and that the third voltage is applied to the third electrode system instead of applying the third voltage to the second electrode system in the second step.

In the first method for measuring a blood component amount and the second method for measuring a blood component amount, it is preferable that the reagent portion includes a mediator. It is more preferable that the reagent portion further includes an oxidoreductase.

In the first method for measuring a blood component amount and the second method for measuring a blood component amount, it is preferable that the first electrode system is independent of the counter electrode of the second electrode system.

In the first method for measuring a blood component amount and the second method for measuring a blood component amount, the first step and the second step may be performed continuously or with a time interval between them. The time interval may be, e.g., 0.01 to 10 seconds, preferably 0.1 to 5 seconds, and more preferably 0.5 to 2 seconds.

In the first method for measuring a blood component amount and the second method for measuring a blood component amount, the second voltage may be, e.g., 0.5 to 5 V, preferably 1 to 3 V, and more preferably 1.5 to 2.5 V.

In the first method for measuring a blood component amount and the second method for measuring a blood component amount, the third voltage may be, e.g., 0.1 to 10 V, preferably 0.1 to 6.5 V, and more preferably 0.5 to 2.5 V.

In the first method for measuring a blood component amount and the second method for measuring a blood component amount, it is preferable that the first voltage is 0.05 to 1 V and an application time of the first voltage is 0.05 to 30 seconds, and the second voltage is 0.5 to 5 V and an application time of the second voltage is 0.01 to 5 seconds.

The first method for measuring a blood component amount and the second method for measuring a blood component amount preferably include a previous step of applying the first voltage only to the first electrode system before the first step. It is more preferable that a third current value that flows through the first electrode system is detected in the previous step, and the third voltage is selected based on the third current value.

In the first method for measuring a blood component amount and the second method for measuring a blood component amount, it is preferable that the third voltage is selected based on the first current value.

In the first method for measuring a blood component amount and the second method for measuring a blood component amount, it is preferable that the first working electrode, the first counter electrode, the second working electrode, and the second counter electrode are made of gold, platinum, or palladium.

In the first method for measuring a blood component amount and the second method for measuring a blood component amount, it is preferable that the third working electrode and the third counter electrode are made of gold, platinum, or palladium.

In the biosensor used in the method for measuring a blood component amount of the present invention, it is preferable that the electrode on which the reagent portion is not provided is coated with a polymeric material in order to prevent adhesion of impurities, oxidation, or the like. Examples of the polymeric material include the following: carboxymethyl cellulose (CMC); hydroxyethyl cellulose; hydroxypropyl cellulose; methyl cellulose; ethyl cellulose; ethylhydroxyethyl cellulose; carboxyethyl cellulose; polyvinyl alcohol; polyvinyl pyrrolidone; polyamino acids such as polygine; polystyrene sulfonate; gelatin and its derivatives; polyacrylic acid and its salts; polymethacrylic acid and its salts; starch and its derivatives; maleic anhydride polymer and its salts; and agarose gel and its derivatives. These materials may be used individually or in combinations of two or more. In particular, CMC is preferred. The coating of the electrode with the polymeric material is not particularly limited. For example, a solution of the polymeric material may be prepared and applied to the surface of the electrode. After drying the solution, the solvent in the coating film may be removed. The ratio of the polymeric material to the whole reagent solution for forming the reagent portion may be, e.g., 0.001 to 10 wt %, preferably 0.005 to 5 wt %, and more preferably 0.01 to 2 wt %.

In the biosensor used in the method for measuring a blood component amount of the present invention, the closest distance between the working electrode and the counter electrode in each of the first electrode system and the second electrode system is preferably 0.05 mm or more. If the distance between the electrodes is 0.05 mm or more, the reliability of the measured value is improved. The distance between the electrodes is more preferably 0.1 mm or more, and further preferably 0.5 mm or more.

In the method for measuring a blood component amount of the present invention, it is preferable that a calibration curve and a calibration table of the Hct value and the blood component amount have been previously prepared, and the correction based on the second current value uses either the calibration curve or the calibration table.

In the method for measuring a blood component amount of the present invention, it is preferable that an environmental temperature is further measured, and the blood component amount is corrected with the environmental temperature. This is because the enzyme reaction is affected by the environmental temperature. In this case, it is preferable that the correction with the environmental temperature uses either a calibration curve or a calibration table, which have been previously prepared.

In the biosensor used in the method for measuring a blood component amount of the present invention, the blood components to be measured may include, e.g., glucose, lactic acid, uric acid, bilirubin, and cholesterol. In the biosensor used in the method for measuring a blood component amount of the present invention, it is preferable that the reagent portion further includes an oxidoreductase. The oxidoreductase may be appropriately selected in accordance with the blood components to be measured. Examples of the oxidoreductase include glucose oxidase, lactate oxidase, cholesterol oxidase, bilirubin oxidase, glucose dehydrogenase, and lactate dehydrogenase. The amount of the oxidoreductase may be, e.g., 0.01 to 100 U, preferably 0.05 to 10 U, and more preferably 0.1 to 5 U per one sensor or one measurement. In particular, glucose is preferred as a measuring object, and glucose oxidase and glucose dehydrogenase are preferred as oxidoreductases.

In the biosensor used in the method for measuring a blood component amount of the present invention, the first electrode system has the first working electrode and the first counter electrode, and the second electrode system has the second working electrode and the second counter electrode. Moreover, it is preferable that the first working electrode and the first counter electrode of the first electrode system are independent of the second counter electrode of the second electrode system. In the first electrode system and the second electrode system, the first working electrode and the first counter electrode of the first electrode system may also be used as the second working electrode of the second electrode system.

The biosensor used in the method for measuring a blood component amount of the present invention may further include an insulating substrate, on which a first electrode system, a second electrode system, and a flow path for the introduction of blood into each of the electrode systems are formed. One end of the flow path may be open to the outside of the biosensor and serve as a blood inlet. In this case, the flow path may have one blood inlet and branch into multiple paths in the middle. The end of each of the branched paths may communicate with each analytical portion. Other than this configuration, the second electrode system may be located in the middle of the flow path, and the first electrode system may be located downstream of the second electrode system.

The biosensor used in the method for measuring a blood component amount of the present invention may further include a spacer and a cover. The cover may be disposed on the insulating substrate via the spacer.

In the sensor for measuring blood components of the present invention, it is preferable that a polymeric material, an enzyme stabilizer, and a crystal homogenizing agent are further arranged on the first electrode system.

In the biosensor used in the method for measuring a blood component amount of the present invention, the reagent portion preferably includes a mediator, more preferably includes a mediator and an oxidoreductase, even more preferably includes a mediator and an enzyme stabilizer, and further preferably includes a mediator, an enzyme stabilizer, and a crystal homogenizing agent.

The mediator is not particularly limited and may be, e.g., ferricyanide, p-benzoquinone, p-benzoquinone derivatives, phenazine methosulfate, methylene blue, ferrocene, or ferrocene derivatives. In particular, ferricyanide is preferred, and potassium ferricyanide is more preferred. The amount of the mediator to be mixed is not particularly limited and may be, e.g., 0.1 to 1000 mM, preferably 1 to 500 mM, and more preferably 10 to 200 mM per one measurement or one sensor.

The enzyme stabilizer may be, e.g., sugar alcohols. Examples of the sugar alcohols include open-chain polyalcohols and cyclic sugar alcohols such as sorbitol, maltitol, xylitol, mannitol, lactitol, reduced palatinose, arabinitol, glycerol, ribitol, galactitol, sedoheptitol, perseitol, volemitol, styracitol, polygalitol, iditol, talitol, allitol, isylitol, hydrogenated starch hydrolysate, and isylitol. The enzyme stabilizer may also be stereoisomers, substitution products, or derivatives of these sugar alcohols. These sugar alcohols may be used individually or in combinations of two or more. In particular, maltitol is preferred. The amount of the enzyme stabilizer to be mixed may be, e.g., 0.1 to 500 mM, preferably 0.5 to 100 mM, and more preferably 1 to 50 mM per one measurement or one sensor.

The crystal homogenizing agent is used to homogenize the crystalline state of the reagent portion and may be, e.g., amino acids. Examples of the amino acids include the following: glycine; alanine; valine; leucine; isoleucine; serine; threonine; methionine; asparagine; glutamine; arginine; lysine; histidine; phenylalanine; tryptophan; proline; sarcosine; betaine; taurine; and salts, substitution products, and derivatives thereof. These amino acids may be used individually or in combinations of two or more. In particular, glycine, serine, proline, threonine, lysine, and taurine are preferred, and taurine is more preferred. The amount of the crystal homogenizing agent to be mixed may be, e.g., 0.1 to 1000 mM, preferably 10 to 500 mM, and more preferably 20 to 200 mM per one measurement or one sensor.

The biosensor used in the method for measuring a blood component amount of the present invention may further include an blood detecting electrode. It is preferable that the blood detecting electrode is located downstream of at least one of the electrode systems from the blood inlet, and can detect that blood has been reliably introduced into at least one of the electrode systems. It is more preferable that the blood detecting electrode is located most downstream of each of the electrode systems. The blood detecting electrode may also be used as at least one of the first counter electrode of the first electrode system and the second counter electrode of the second electrode system.

Next, the measuring device of the present invention may further include a correction means for correcting the apparent blood component amount based on the second current value. In the measuring device of the present invention, the third voltage applied to the second electrode system may be a voltage higher than the value at which the electrolysis of water occurs, and is preferably 0.1 to 10 V, more preferably 0.1 to 6.5 V, and further preferably 1.5 to 2.5 V.

Figure 44:
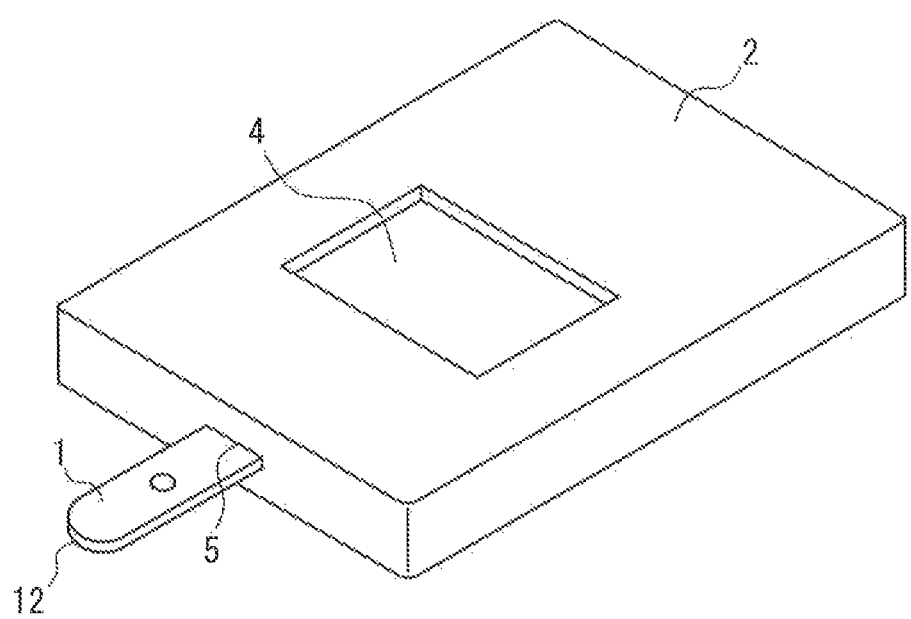
FIG. 44 is a perspective view showing an example of a measuring device of the present invention.

FIG. 44 is a perspective view showing an example of a measuring device of the present invention, where a biosensor used in the measuring method of the present invention is attached to the measuring device. As shown in FIG. 44, a measuring device 2 has an insertion port 5 for a sensor at one end, into which a sensor 1 is inserted and held. Reference numeral 12 denotes a sample inlet of the sensor 1. Moreover, a display unit 4 is provided substantially in the center of the measuring device 2 and displays the results of the measurement.

Figure 45:
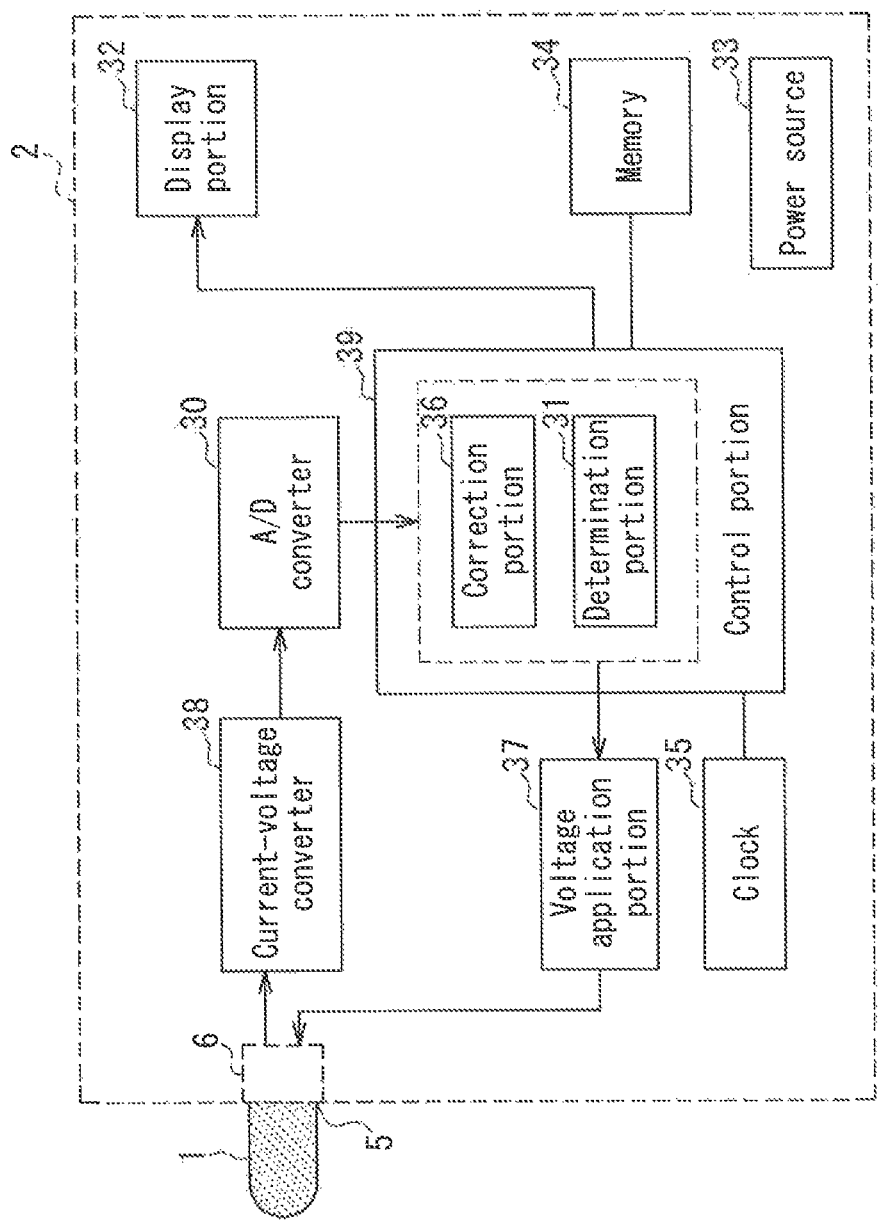
FIG. 45 is an electrical block diagram of a blood component amount measuring device to which a biosensor is attached in an embodiment of the present invention.

FIG. 45 shows an example of an electrical block diagram of a measuring device of the present invention, where a biosensor used in the measuring method of the present invention is attached to the measuring device. In the measuring device of an embodiment of the present invention, a voltage application portion 37 for applying a voltage and a current-voltage converter 38 are connected to an input terminal portion 6. A voltage is supplied from a control portion 39 to the voltage application portion 37, and this voltage is then applied via the input terminal portion 6 to a desired electrode among the first electrode system, the second electrode system, and the blood component introduction detecting electrode of the biosensor 1 for a predetermined time. The current flowing between the electrodes of the biosensor 1 as a result of this voltage application is converted to a voltage by the current-voltage converter 38, and subsequently the voltage is converted to a digital value by an A/D converter 30. Thereafter, a determination portion 31 compares the digitized voltage value with a threshold value.

A display portion 32 is connected to the control portion 39 and displays the glucose value detected by the biosensor 1 and the results of the determination made by the determination portion 31. In FIG. 45, reference numeral 33 denotes a power source that supplies power to each portion. Reference numeral 34 denotes a memory that stores a table containing hematocrit values and applied voltages, application times, etc. for measuring the glucose, or a calibration curve and a calibration table that have been previously prepared from the environmental temperature.

A clock 35 is connected to the control portion 39. The control portion 39 makes use of the hour and the time of the clock 35 to perform various control operations. The control portion 39 further includes a correction portion 36 that corrects the measured blood glucose level with the hematocrit value to improve the measurement accuracy of the blood glucose level.

Next, examples of the method for measuring a blood component amount of the present invention will be described with reference to the drawings.

EXAMPLE 1

Figure 2:
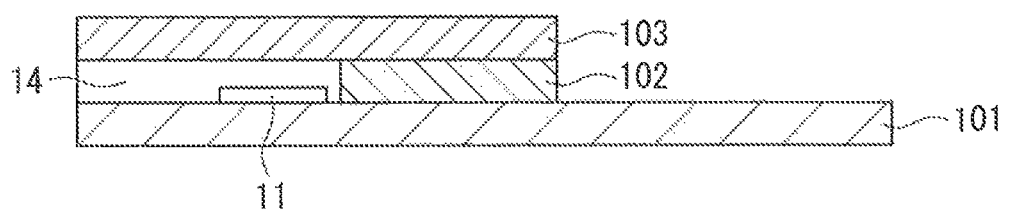
FIG. 2 is a cross-sectional view of the sensor in FIG. 1.
Figure 3:
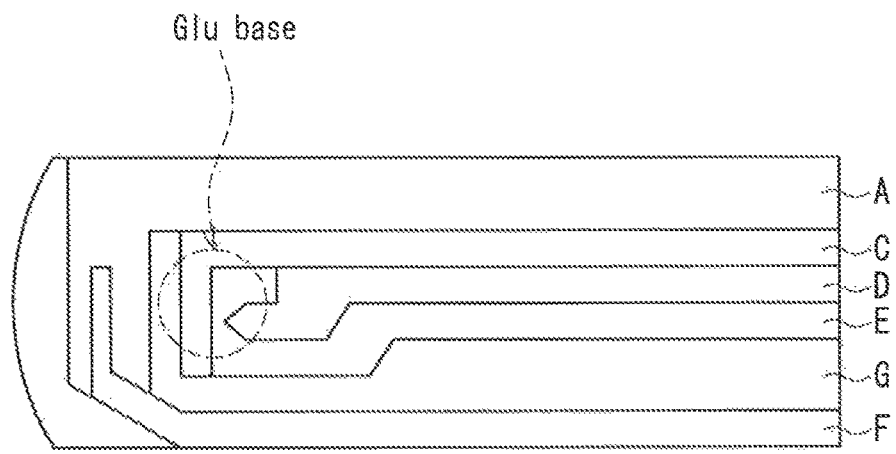
FIG. 3 is a plan view of the sensor in FIG. 1.

FIGS. 1, 2, and 3 show an example of a sensor for measuring blood components used in the measuring method of the present invention. FIG. 1 is an exploded perspective view of the sensor. FIG. 2 is a cross-sectional view of the sensor. FIG. 3 is a plan view of the sensor. In FIGS. 1, 2, and 3, the same portions are denoted by the same reference numerals. This sensor is used, e.g., to measure glucose as a blood component.

As shown in the drawings, the sensor includes an insulating substrate 101 and six electrodes A, C, D, E, G, and F formed on the insulating substrate 101. These electrodes can switch between the working electrode and the counter electrode. The surfaces of the electrodes A, C, D, E, F, and G are coated with a polymeric material such as CMC. A reagent layer 11 is arranged to cover a part of the electrodes C, D, E, and G. The reagent layer 11 includes an oxidoreductase such as glucose dehydrogenase and a mediator such as potassium ferricyanide, and may include, e.g., an enzyme stabilizer and a crystal homogenizing agent as optional components. A cover 103 is disposed on the insulating substrate 101 via a spacer 102, while leaving one end of the sensor (i.e., the right end in the drawings) uncovered. In the sensor, a flow path 14 is formed by the insulating substrate 101, the spacer 102, and the cover 103 to introduce blood into each of the electrodes (A, C, D, E, G, and F). The end of the flow path 14 extends to the other end of the sensor (i.e., the left end in the drawings) and is open to the outside, thereby serving as a blood inlet 12. Each of the six electrodes (A, C, D, E, G, and F) is connected to a lead, and the leads extend to the one end of the sensor (i.e., the right end in the drawings). The ends of the leads are exposed and not covered with the cover. The cover 103 has an air hole 13 in a portion corresponding to the right end of the flow path 14.

In the present invention, the material of the insulating substrate is not particularly limited and may be, e.g., polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylate resin (PMMA), ABS resin (ABS), or glass. In particular, polyethylene terephthalate (PET), polycarbonate (PC), and polyimide (PI) are preferred, and polyethylene terephthalate (PET) is more preferred. The size of the insulating substrate is not particularly limited. For example, the insulating substrate has a total length of 5 to 100 mm, a width of 2 to 50 mm, and a thickness of 0.05 to 2 mm, preferably has a total length of 7 to 50 mm, a width of 3 to 20 mm, and a thickness of 0.1 to 1 mm, and more preferably has a total length of 10 to 30 mm, a width of 3 to 10 mm, and a thickness of 0.1 to 0.6 mm. The material and size of the insulating substrate are the same as in Examples 2 to 6, as will be described later.

The electrodes and the leads on the insulating substrate can be provided, e.g., by forming a conductive layer by sputtering or evaporation with the use of a material such as gold, platinum, or palladium, and processing the conductive layer into a particular electrode pattern with a laser. The laser may be, e.g., a YAG laser, a $CO_2$ laser, or an excimer laser. This process also is the same as in Examples 2 to 6, as will be described later.

The reagent layer 11 is formed in the following manner. For example, an aqueous solution containing 0.1 to 5 U per sensor of glucose dehydrogenase, 10 to 200 mM of potassium ferricyanide, 1 to 50 mM of maltitol, and 20 to 200 mM of taurine is dropped onto a circular slit portion 20 (not shown) and dried. The presence of the slit portion 20 can suppress the spread of the dropped aqueous solution, so that the reagent layer 11 can be located in a more accurate position. Thus, the reagent layer 11 is formed to cover a part of the electrode portion composed of the electrodes C, D, and E. The drying process may be, e.g., natural drying or hot-air forced drying. However, if the temperature is too high, the enzyme can be inactivated. Therefore, the hot air of about 50° C. is preferably used.

In the present invention, the material of the spacer is not particularly limited and may be, e.g., the same as that of the insulating substrate. The size of the spacer is not particularly limited. For example, the spacer has a total length of 5 to 100 mm, a width of 2 to 50 mm, and a thickness of 0.01 to 1 mm, preferably has a total length of 7 to 50 mm, a width of 3 to 20 mm, and a thickness of 0.05 to 0.5 mm, and more preferably has a total length of 10 to 30 mm, a width of 3 to 10 mm, and a thickness of 0.05 to 0.25 mm. The spacer in this example has an I-shaped notch that serves as a flow path for the introduction of blood. For example, the I-shaped notch has a total length of 0.5 to 8 mm and a width of 0.1 to 5 mm, preferably has a total length of 1 to 10 mm and a width of 0.2 to 3 mm, and more preferably has a total length of 1 to 5 mm and a width of 0.5 to 2 mm. The notch may be formed, e.g., by punching through the spacer with a laser or drill, or by using a die that allows a notch to be provided during the formation of the spacer. The material, size, and notch of the spacer are the same as in Examples 2 to 6, as will be described later.

In the present invention, the material of the cover is not particularly limited and may be, e.g., the same as that of the insulating substrate. It is more preferable that a portion of the cover that forms the ceiling of the flow path for the introduction of blood is subjected to a hydrophilic treatment. The hydrophilic treatment may be, e.g., a method for applying a surface active agent or a method for introducing a hydrophilic functional group such as a hydroxyl group, a carbonyl group, or a carboxyl group into the surface of the cover by plasma processing. Alternatively, a layer of a surface active agent such as lecithin may be formed on the reagent layer. The size of the cover is not particularly limited. For example, the cover has a total length of 5 to 100 mm, a width of 3 to 50 mm, and a thickness of 0.01 to 0.5 mm, preferably has a total length of 10 to 50 mm, a width of 3 to 20 mm, and a thickness of 0.05 to 0.25 mm, and more preferably has a total length of 15 to 30 mm, a width of 5 to 10 mm, and a thickness of 0.05 to 0.1 mm. The cover preferably has an air hole, e.g., in the form of a circle, ellipse, or polygon. For example, the air hole has a maximum diameter of 0.01 to 10 mm, preferably has a maximum diameter of 0.05 to 5 mm, and more preferably has a maximum diameter of 0.1 to 2 mm. The air hole may be formed, e.g., by punching through the cover with a laser or drill, or by using a die that allows an air vent to be provided during the formation of the cover. The material, size, and air hole of the cover are the same as in Examples 2 to 6, as will be described later.

The insulating substrate, the spacer, and the cover are laminated in this order and integrated into one component, thereby producing the sensor. For the integration, the three members are joined together, e.g., using an adhesive or a heat seal. Examples of the adhesive include an epoxy adhesive, an acrylic adhesive, a polyurethane adhesive, a thermosetting adhesive (such as a hot-melt adhesive), and a UV curable adhesive. This process also is the same as in Examples 2 to 6, as will be described later.

A blood component amount, e.g., a blood glucose level is measured with the above sensor in the following manner. First, a special-purpose lancet is used to prick the finger tip or the like and draw a small amount of blood. On the other hand, the sensor is set in a special-purpose measuring device (meter). The blood is brought into contact with the blood inlet of the sensor set in the measuring device, and then is introduced into the sensor by capillary action. Analysis of the blood by the sensor is performed in the following steps.

In this measuring method, the electrode C is used as the working electrode of the first electrode system, the electrode D and the electrode E are used as the counter electrode of the first electrode system, the electrode F is used as the working electrode of the second electrode system, and the electrode G is used as the counter electrode of the second electrode system.

(Step 1: Detection of Sample (Blood))

A voltage is applied between the electrode D and the electrode E, and the introduction of the blood is detected by a change in a current value due to the blood introduced into the sensor. After confirming the introduction of the blood, the next step is started. In the step 1, the applied voltage is, e.g., 0.05 to 1 V, and glucose in the blood reacts with the glucose oxidoreductase for a certain period of time.

(Step 2: Measurement of Apparent Amount of Glucose)

After glucose in the blood reacts with the glucose oxidoreductase for a certain period of time, a first voltage is applied to both of the electrodes of the first electrode system (i.e., the working electrode including the electrode C and the counter electrode including the electrode D and the electrode E), and a second voltage is applied to both of the electrodes of the second electrode system (i.e., the working electrode including the electrode F and the counter electrode including the electrode G) (the first step). As described above, the reagent layer 11 is formed to cover a part of the electrode portion composed of the electrode C (the working electrode of the first electrode system), the electrode D (the counter electrode of the first electrode system), and the electrode E (the counter electrode of the first electrode system) of the biosensor. The reduced mediator that is generated on the electrode C of the first electrode system by the enzyme reaction is oxidized, and an oxidation current (a first current value) is detected. Based on the oxidation current (the first current value), an apparent amount of glucose (an apparent blood component amount) in the blood is calculated. The application time of the first voltage is the same as that of the second voltage. The reaction time between the glucose and the oxidoreductase may be, e.g., 0 to 60 seconds, preferably 0 to 30 seconds, and more preferably 0 to 10 seconds. The first voltage in the step 2 (the first step) may be, e.g., 0.05 to 1.0 V, preferably 0.1 to 0.8 V, and more preferably 0.2 to 0.6 V. The application time of the first voltage may be, e.g., 0.05 to 30 seconds, preferably 0.1 to 10 seconds, and more preferably 0.5 to 5 seconds. The second voltage in the step 2 (the first step) may be, e.g., 0.5 to 5 V, preferably 1 to 3 V, and more preferably 1.5 to 2.5 V. The application time of the second voltage may be, e.g., 0.01 to 5 seconds, preferably 0.01 to 2.5 seconds, and more preferably 0.1 to 1 second.

The combinations of the first voltage and the second voltage in the step 2 (the first step) may include the following. For example, the first voltage is 0.05 to 1 V and the application time of the first voltage is 0.05 to 30 seconds, and the second voltage is 0.5 to 5 V and the application time of the second voltage is 0.01 to 5 seconds. Preferably, the first voltage is 0.01 to 0.8 V and the application time of the first voltage is 0.1 to 10 seconds, and the second voltage is 1 to 3 V and the application time of the second voltage is 0.01 to 2.5 seconds. More preferably, the first voltage is 0.2 to 0.6 V and the application time of the first voltage is 0.5 to 5 seconds, and the second voltage is 1.5 to 2.5 V and the application time of the second voltage is 0.1 to 1 second.

The measuring method may include a previous step of applying the first voltage only to the first electrode system before the first voltage is applied to both of the electrodes of the first electrode system and the second voltage is applied to both of the electrodes of the second electrode system in the step 2 (the first step). The first voltage in the previous step may be, e.g., 0.05 to 1.0 V, preferably 0.1 to 0.8 V, and more preferably 0.2 to 0.6 V. The application time of the first voltage in the previous step may be, e.g., 0.05 to 30 seconds, preferably 0.1 to 10 seconds, and more preferably 0.5 to 5 seconds.

The second voltage and the application time of the second voltage may be selected based on the first current value obtained in the step 2. Specifically, when the first current value is 0.01 to 0.1 V, the second voltage may be 1.5 to 2.0 V and the application time of the second voltage may be 0.1 to 1 second. When the first current value is 0.1 to 1 V, the second voltage may be 2.0 to 2.5 V and the application time of the second voltage may be 0.1 to 1 second.

Before the first step, the first voltage may be applied only to the first electrode system to detect a third current value that flows through the first electrode system, and the second voltage and the application time of the second voltage may be selected based on the third current value. In this case, the first voltage may be, e.g., 0.05 to 1.0 V, preferably 0.1 to 0.8 V, and more preferably 0.2 to 0.6 V. The application time of the first voltage may be, e.g., 0.05 to 30 seconds, preferably 0.1 to 10 seconds, and more preferably 0.5 to 5 seconds. Specifically, when the third current value is 0.01 to 0.1 V, the second voltage may be 1.5 to 2.0 V and the application time of the second voltage may be 0.1 to 1 second. When the third current value is 0.1 to 1 V, the second voltage may be 2.0 to 2.5 V and the application time of the third voltage may be 0.1 to 1 second.

(Step 3: Measurement of Hct Value)

The application of the first voltage to the first electrode system is stopped, and a third voltage is applied to both of the electrodes of the second electrode system (i.e., the working electrode including the electrode F and the counter electrode including the electrode G), so that a current (a second current value) that depends on an Hct value based on the electrolytic oxidation reaction of glucose can be detected (the second step). The conversion from the detected current (the second current value) to an Hct value can be performed by previously determining the calibration curve or the calibration table. This correction may use the Hct value obtained from the calibration curve of the current and the Hct value, which has been previously prepared, or may use the detected current directly. The third voltage in the step 3 (the second step) may be, e.g., 0.1 to 10 V, preferably 0.1 to 6.5 V, and more preferably 0.5 to 2.5 V. The application time of the third voltage may be, e.g., 0.05 to 10 seconds, preferably 0.1 to 5 seconds, and more preferably 0.2 to 1 second. In the step 3, the mediator is not arranged on the electrode F (the working electrode). Moreover, there is a predetermined gap between the electrode G and the electrode F, and no reagent such as a mediator is arranged, but only blood is present in this gap. Therefore, an oxidation current that depends on the Hct value can be detected without being affected by the reagent. Even if the surface of the electrode F is not coated with a polymeric material or the like, the measurement can be performed. The step 3 (the second step) may be performed either immediately after the step 2 (the first step) or after a time interval from the step 2 (the first step). The time interval may be, e.g., 0 to 10 seconds, preferably 0.05 to 5 seconds, and more preferably 0.1 to 1 second. The third voltage in the step 3 may be either the same as or different from the second voltage in the step 2.

The third voltage and the application time of the third voltage may be selected based on the first current value obtained in the step 2. Specifically, when the first current value is 0.01 to 0.1 V, the third voltage may be 2 to 2.5 V and the application time of the third voltage may be 0.2 to 1 second. When the first current value is 0.1 to 1 V, the third voltage may be 2.5 to 3 V and the application time of the third voltage may be 0.2 to 1 second.

Before the first step, the first voltage may be applied to the first electrode system to detect a third current value that flows through the first electrode system, and the third voltage and the application time of the third voltage may be selected based on the third current value. In this case, the first voltage may be, e.g., 0.05 to 1.0 V, preferably 0.1 to 0.8 V, and more preferably 0.2 to 0.6 V. The application time of the first voltage may be, e.g., 0.05 to 30 seconds, preferably 0.1 to 10 seconds, and more preferably 0.5 to 5 seconds. Specifically, when the third current value is 0.01 to 0.1 V, the third voltage may be 2 to 2.5 V and the application time of the third voltage may be 0.2 to 1 second. When the third current value is 0.1 to 1 V, the third voltage may be 2.5 to 3 V and the application time of the third voltage may be 0.1 to 1 second.

(Step 4: Correction of Blood Component)

The amount of glucose obtained in the step 2 (the first step) is corrected with the Hct value detected in the step 3 (the second step). This correction is preferably performed based on the calibration curve (including the calibration table) that has been previously prepared. The corrected amount of glucose is displayed or stored in the measuring device. Instead of correcting the amount of glucose after the Hct value has been determined, as described above, the amount of glucose may be corrected by directly using the current value (the second current value) that depends on the Hct value detected in the step 3 (the second step).

EXAMPLE 2

Figure 5:
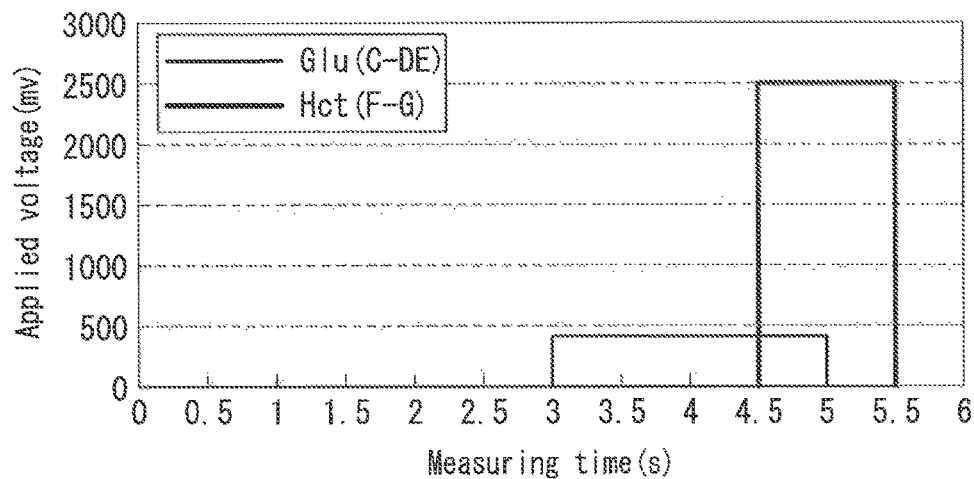
FIG. 5 is a graph showing the relationship between an application time and an applied current in Example 2.

In this example, a sensor shown in FIGS. 1 to 3 is produced in the same manner as Example 1. Using the sensor that includes the electrode C as the working electrode of the first electrode system, the electrode D and the electrode E as the counter electrode of the first electrode system, the electrode F as the working electrode of the second electrode system, and the electrode G as the counter electrode of the second electrode system, a response current and a sensitivity difference are determined by varying the blood component amount in blood. Moreover, as Comparative Example 1, using the same sensor that includes the electrode C as the working electrode of the first electrode system, the electrode D and the electrode E as the counter electrode of the first electrode system, the electrode F as the working electrode of the second electrode system, and the electrode G as the counter electrode of the second electrode system, a response current and a sensitivity difference are determined by varying the blood component amount in blood. The measurement of a sample (blood) and a blood component (glucose) and the correction of the blood component are performed in the same manner as Example 1. The reagent layer is formed in the following manner. A reagent solution is prepared by dissolving glucose dehydrogenase, potassium ferricyanide (60 mM), and taurine (80 mM) in a CMC aqueous solution (0.1 wt %). Then, the reagent solution is dropped onto the electrodes and dried. The distance between the working electrode and the counter electrode is 0.1 mm or more. Three types of blood samples, in which the Hct values are adjusted to 25%, 45%, and 65%, respectively, are prepared for each glucose concentration. For the three blood samples, the sensor is used to measure a current flowing through both of the electrodes of the sensor and to determine a response current value and a sensitivity difference in the measurement of the Hct value under the following conditions: the first voltage is 400 mV and the application time of the first voltage is from 3 to 5 seconds; the second voltage is 2500 mV and the application time of the second voltage is from 4.5 to 5 seconds; and the third voltage is 2500 mV and the application time of the third voltage is from 5 to 5.5 seconds (see FIG. 5). In FIG. 5, "Glu (C-DE)" represents the application of the voltage to the first electrode system, and "Hct (F-G)" represents the application of the voltage to the second electrode system. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds.

COMPARATIVE EXAMPLE 1

Figure 4:
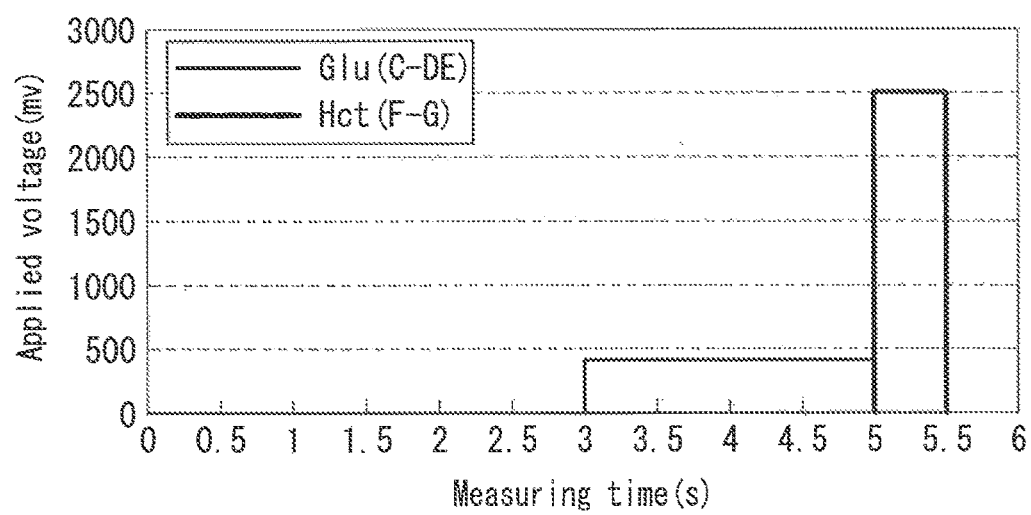
FIG. 4 is a graph showing the relationship between an application time and an applied current in Comparative Example 1.

In Comparative Example 1, for the three blood samples, the sensor is used to measure a current flowing through both of the electrodes of the sensor and to determine a response current value and a sensitivity difference in the measurement of the Hct value under the following conditions: the first voltage is 400 mV and the application time of the first voltage is 3 to 5 seconds; and the second voltage is 2500 mV and the application time of the second voltage is 5 to 5.5 seconds (see FIG. 4). In FIG. 4, "Glu (C-DE)" represents the application of the voltage to the first electrode system, and "Hct (F-G)" represents the application of the voltage to the second electrode system. As can be seen from FIG. 4, the voltage is applied to the first electrode system, and then the voltage is applied to the second electrode system. Unlike the step 2 of the present invention, the first voltage and the second voltage are not simultaneously applied to the first electrode system and the second electrode system, respectively.

EXAMPLE 3

Figure 6:
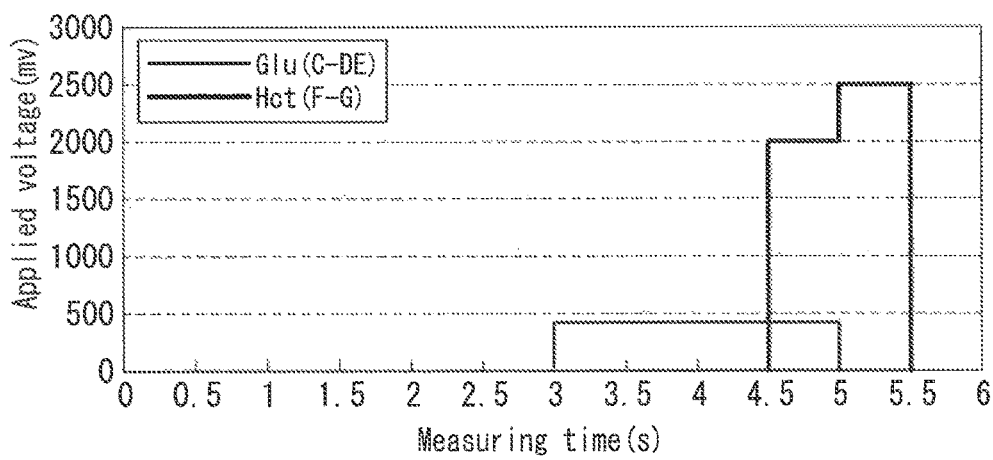
FIG. 6 is a graph showing the relationship between an application time and an applied current in Example 3.

In this example, a response current value and a sensitivity difference in the measurement of the Hct value are determined in the same manner as Example 2, except that a blood component (glucose) concentration of the blood samples is 75 mg/dl, and a current flowing through both of the electrodes of the sensor is measured under the following conditions: the first voltage is 400 mV and the application time of the first voltage is from 3 to 5 seconds; the second voltage is 2000 mV and the application time of the second voltage is from 4.5 to 5 seconds; and the third voltage is 2500 mV and the application time of the third voltage is from 5 to 5.5 seconds (see FIG. 6). In FIG. 6, "Glu (C-DE)" represents the application of the voltage to the first electrode system, and "Hct (F-G)" represents the application of the voltage to the second electrode system. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds.

Figure 7:
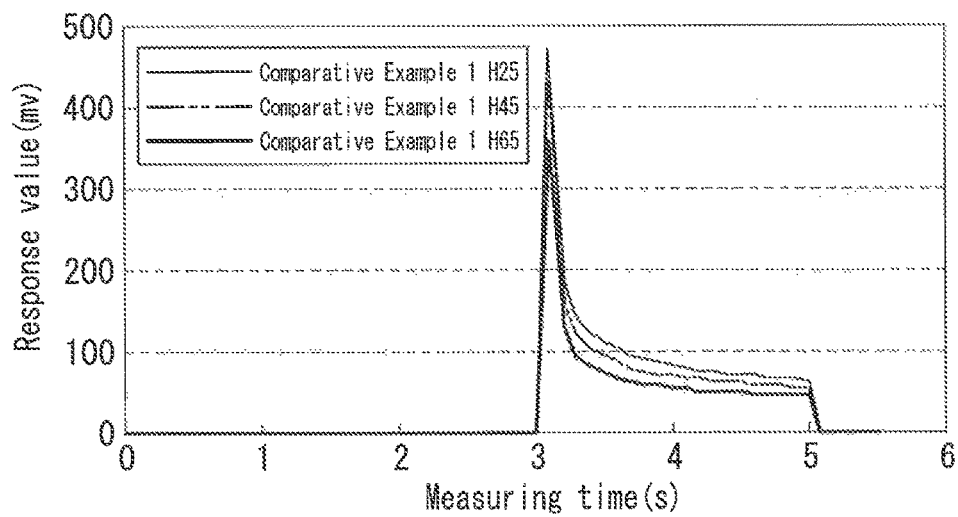
FIG. 7 shows the results of blood samples in which a blood component (glucose) concentration is 75 mg/dl.
Figure 7:
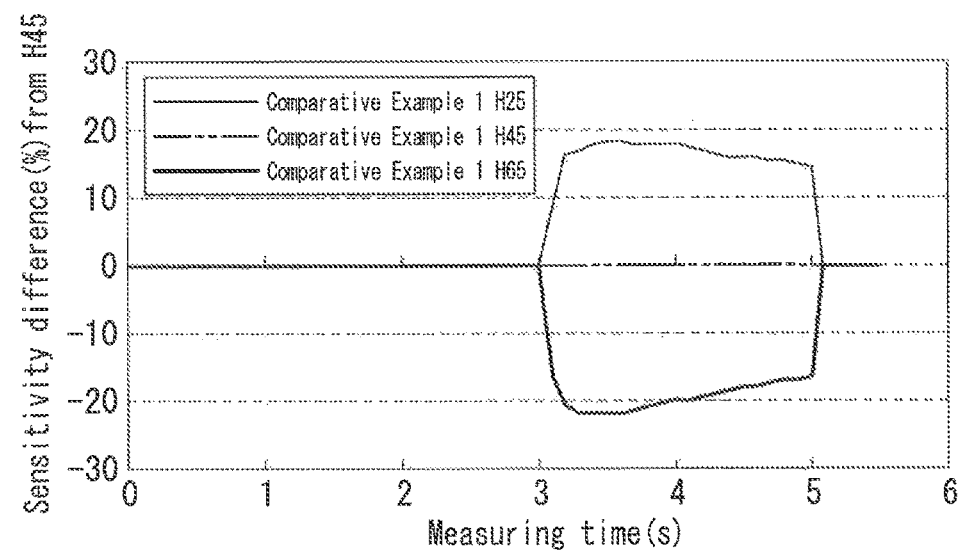

FIG. 7 shows the results of the blood samples in which the blood component (glucose) concentration is 75 mg/dl. FIG. 7(a) is a graph showing changes in the response current value (mV) over time with respect to the applied voltage (mV) in Comparative Example 1. FIG. 7(b) is a graph showing changes in the sensitivity difference (%) over time with respect to the applied voltage (mV) in Comparative Example 1. Specifically, using the blood sample with an Hct value of 45% as a reference, a calibration curve is obtained from the correspondence between the first current value and the blood component (glucose) concentration. FIG. 7(b) shows the sensitivity difference (%) from the true value when the calibration curve is applied to the blood sample with an Hct value of 25% and the blood sample with an Hct value of 65%.

Figure 8:
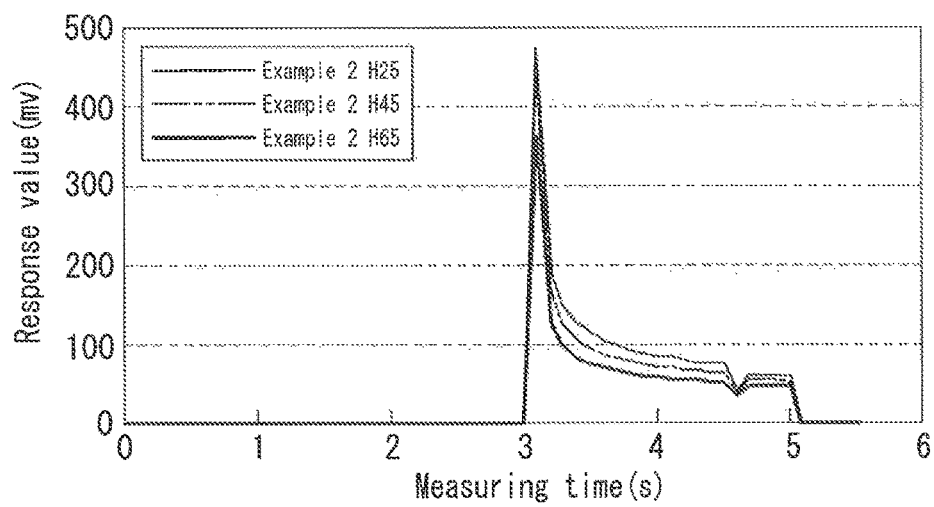
FIG. 8 shows the results of blood samples in which a blood component (glucose) concentration is 75 mg/dl.
Figure 8:
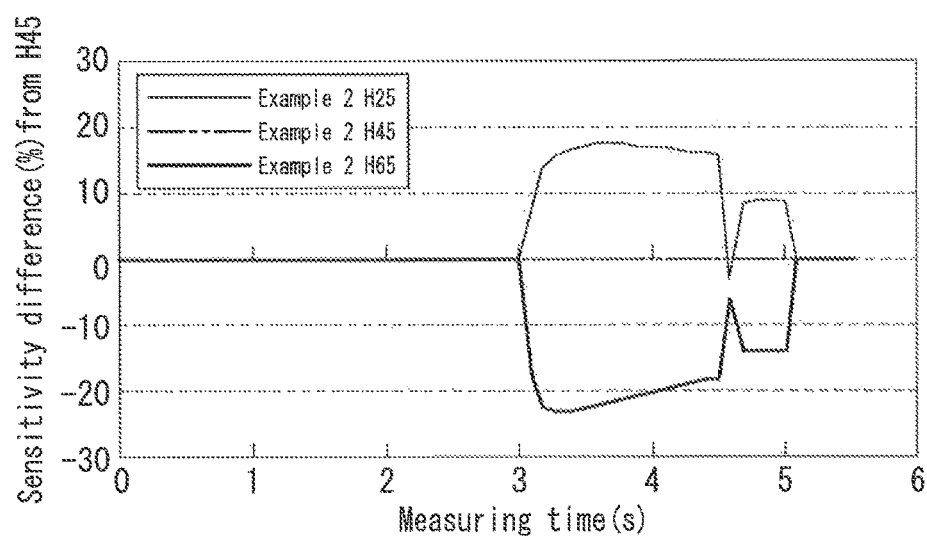

FIG. 8 shows the results of the blood samples in which the blood component (glucose) concentration is 75 mg/dl. FIG. 8(a) is a graph showing changes in the response current value (mV) over time with respect to the applied voltage (mV) in Example 2. FIG. 8(b) is a graph showing changes in the sensitivity difference (%) over time with respect to the applied voltage (mV) in Example 2. Specifically, using the blood sample with an Hct value of 45% as a reference, a calibration curve is obtained from the correspondence between the first current value and the blood component (glucose) concentration. FIG. 8(b) shows the sensitivity difference (%) from the true value when the calibration curve is applied to the blood sample with an Hct value of 25% and the blood sample with an Hct value of 65%.

Figure 9:
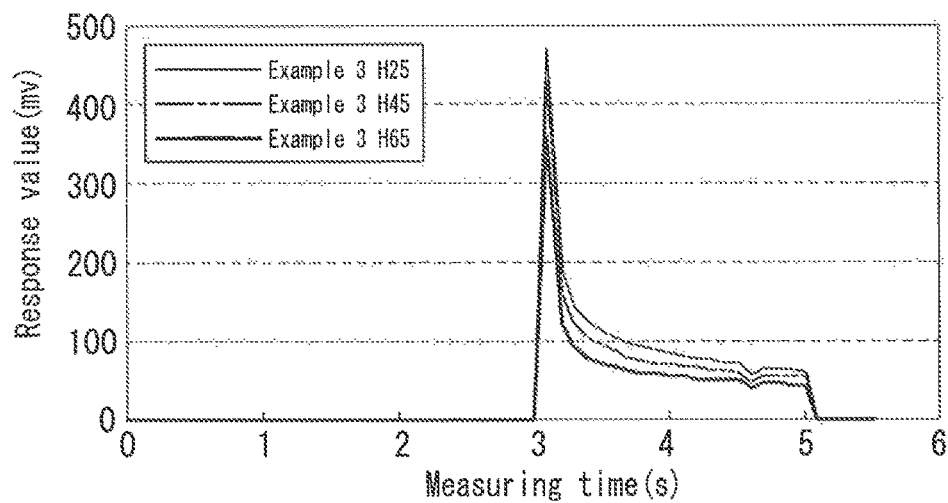
FIG. 9 shows the results of blood samples in which a blood component (glucose) concentration is 75 mg/dl.
Figure 9:
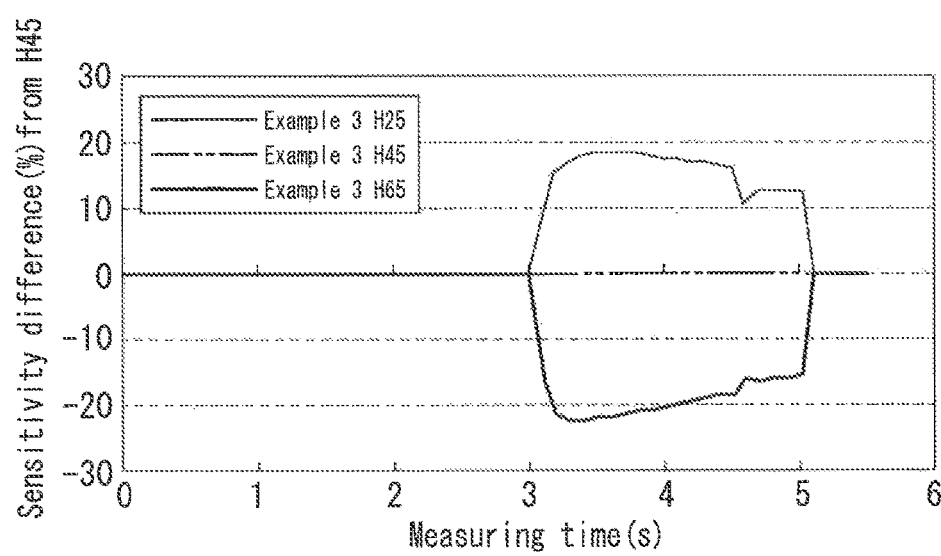

FIG. 9 shows the results of the blood samples in which the blood component (glucose) concentration is 75 mg/dl. FIG. 9(a) is a graph showing changes in the response current value (mV) over time with respect to the applied voltage (mV) in Example 3. FIG. 9(b) is a graph showing changes in the sensitivity difference (%) over time with respect to the applied voltage (mV) in Example 3. Specifically, using the blood sample with an Hct value of 45% as a reference, a calibration curve is obtained from the correspondence between the first current value and the blood component (glucose) concentration. FIG. 9(b) shows the sensitivity difference (%) from the true value when the calibration curve is applied to the blood sample with an Hct value of 25% and the blood sample with an Hct value of 65%. In FIGS. 7 to 9, "H25" represents the use of the blood sample with an Hct value of 25%, "H45" represents the use of the blood sample with an Hct value of 45%, and "H65" represents the use of the blood sample with an Hct value of 65%.

Compared to FIG. 7(a) and FIG. 7(b), in the measuring method of the present invention, as shown in FIG. 8(a) and FIG. 8(b), the sensitivity difference (%) after a measuring time of 4.5 seconds in FIG. 8(b) is smaller than the sensitivity difference (%) in FIG. 7(b). This can confirm that the effect of the Hct is reduced when the blood component amount is measured for each of the blood samples with different Hct values, and thus the accuracy of the measured blood component amount is improved. Moreover, compared to FIG. 7(a) and FIG. 7(b), in the measuring method of the present invention, as shown in FIG. 9(a) and FIG. 9(b), the sensitivity difference (%) after a measuring time of 4.5 seconds in FIG. 9(b) is smaller than the sensitivity difference (%) in FIG. 7(b). This can confirm that the effect of the Hct is reduced when the blood component amount is measured, and thus the accuracy of the measured blood component amount is improved.

Figure 10:
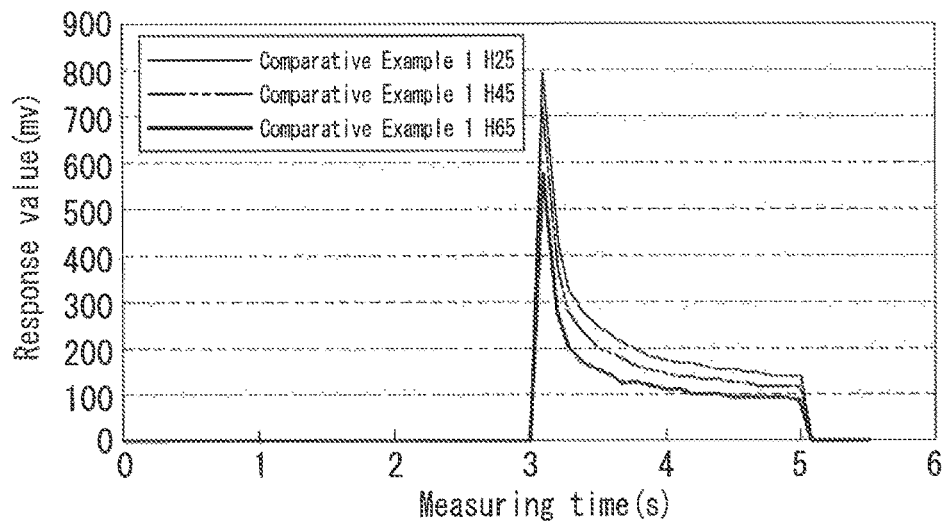
FIG. 10 shows the results of blood samples in which a blood component (glucose) concentration is 150 mg/dl.
Figure 10:
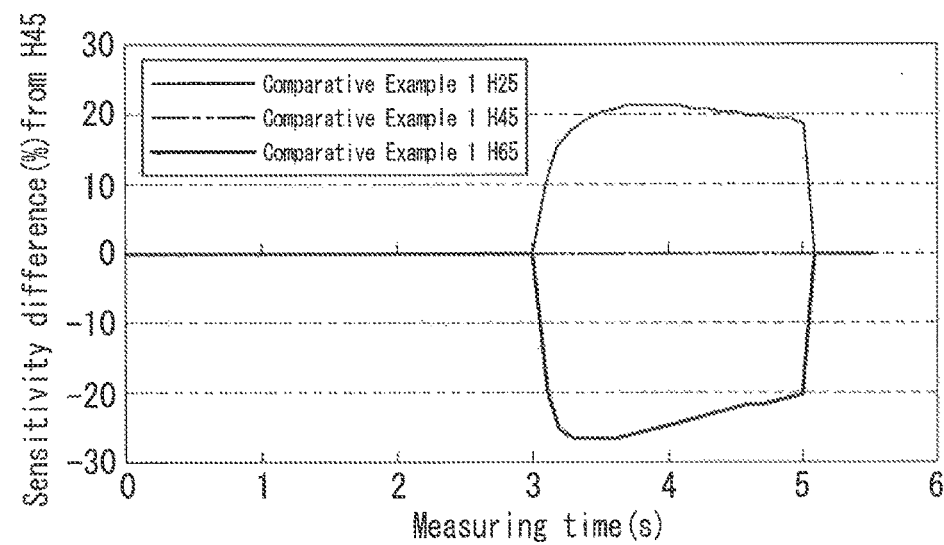

FIG. 10 shows the results of the blood samples in which the blood component (glucose) concentration is 150 mg/dl. FIG. 10(a) is a graph showing changes in the response current value (mV) over time with respect to the applied voltage (mV) in Comparative Example 1. FIG. 10(b) is a graph showing changes in the sensitivity difference (%) over time with respect to the applied voltage (mV) in Comparative Example 1. Specifically, using the blood sample with an Hct value of 45% as a reference, a calibration curve is obtained from the correspondence between the first current value and the blood component (glucose) concentration. FIG. 10(b) shows the sensitivity difference (%) from the true value when the calibration curve is applied to the blood sample with an Hct value of 25% and the blood sample with an Hct value of 65%.

Figure 11:
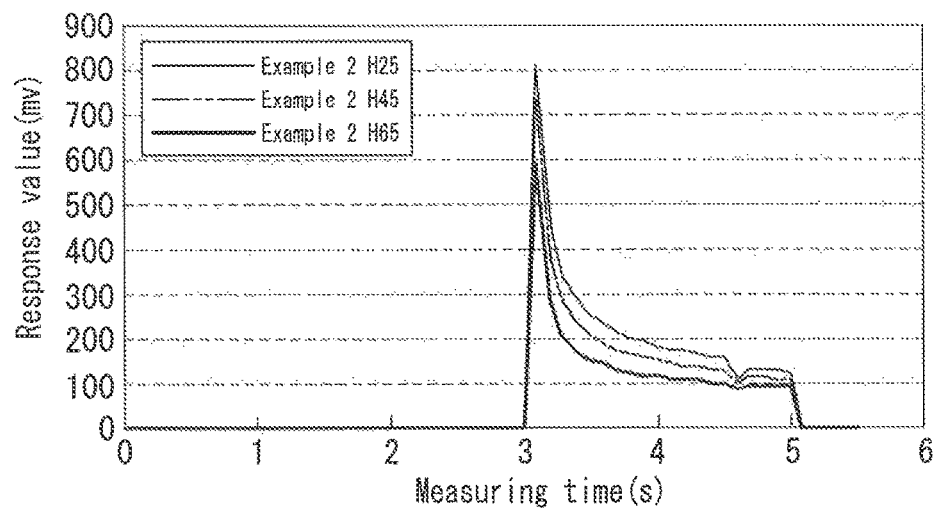
FIG. 11 shows the results of blood samples in which a blood component (glucose) concentration is 150 mg/dl.
Figure 11:
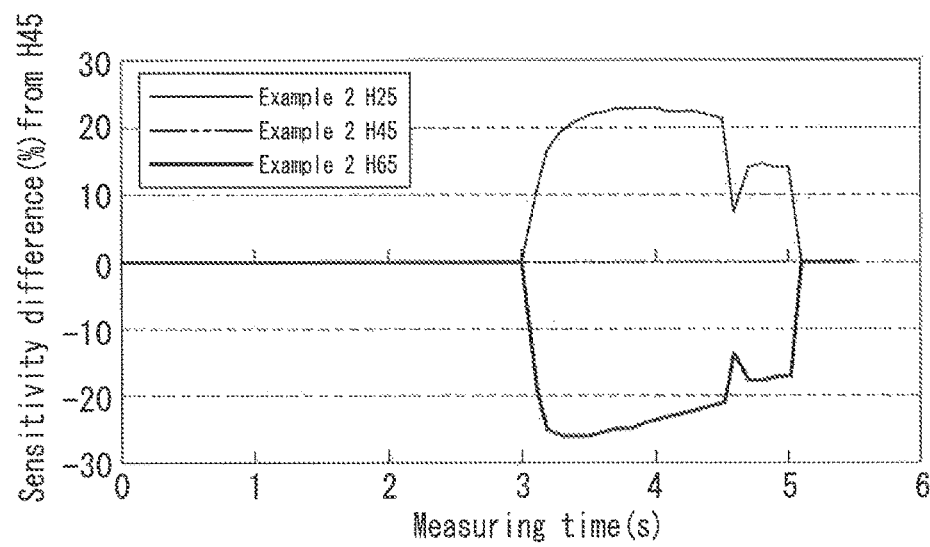

FIG. 11 shows the results of the blood samples in which the blood component (glucose) concentration is 150 mg/dl. FIG. 11(a) is a graph showing changes in the response current value (mV) over time with respect to the applied voltage (mV) in Example 2. FIG. 11(b) is a graph showing changes in the sensitivity difference (%) over time with respect to the applied voltage (mV) in Example 2. Specifically, using the blood sample with an Hct value of 45% as a reference, a calibration curve is obtained from the correspondence between the first current value and the blood component (glucose) concentration. FIG. 11(b) shows the sensitivity difference (%) from the true value when the calibration curve is applied to the blood sample with an Hct value of 25% and the blood sample with an Hct value of 65%.

Figure 12:
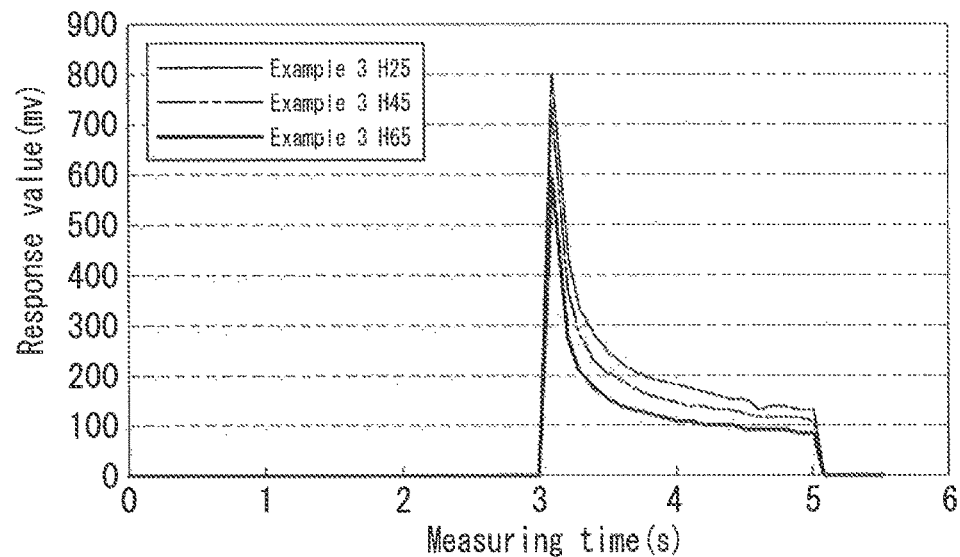
FIG. 12 shows the results of blood samples in which a blood component (glucose) concentration is 150 mg/dl.
Figure 12:
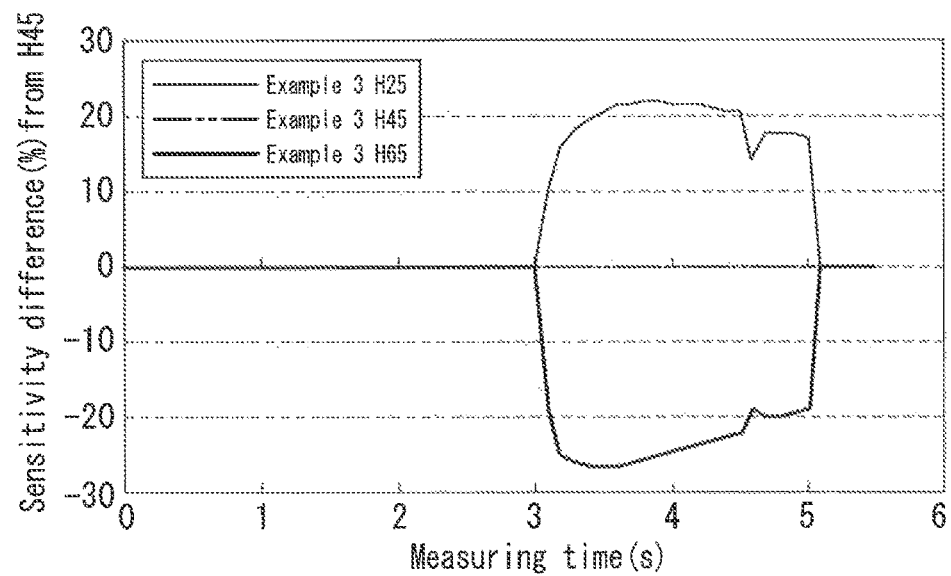

FIG. 12 shows the results of the blood samples in which the blood component (glucose) concentration is 150 mg/dl. FIG. 12(a) is a graph showing changes in the response current value (mV) over time with respect to the applied voltage (mV) in Example 3. FIG. 12(b) is a graph showing changes in the sensitivity difference (%) over time with respect to the applied voltage (mV) in Example 3. Specifically, using the blood sample with an Hct value of 45% as a reference, a calibration curve is obtained from the correspondence between the first current value and the blood component (glucose) concentration. FIG. 12(b) shows the sensitivity difference (%) from the true value when the calibration curve is applied to the blood sample with an Hct value of 25% and the blood sample with an Hct value of 65%. In FIGS. 10 to 12, "H25" represents the use of the blood sample with an Hct value of 25%, "H45" represents the use of the blood sample with an Hct value of 45%, and "H65" represents the use of the blood sample with an Hct value of 65%.

Compared to FIG. 10(a) and FIG. 10(b), in the measuring method of the present invention, as shown in FIG. 11(a) and FIG. 11(b), the sensitivity difference (%) after a measuring time of 4.5 seconds in FIG. 11(b) is smaller than the sensitivity difference (%) in FIG. 10(b). This can confirm that the effect of the Hct is reduced when the blood component amount is measured for each of the blood samples with different Hct values, and thus the accuracy of the measured blood component amount is improved. Moreover, compared to FIG. 10(a) and FIG. 10(b), in the measuring method of the present invention, as shown in FIG. 12(a) and FIG. 12(b), the sensitivity difference (%) after a measuring time of 4.5 seconds in FIG. 12(b) is smaller than the sensitivity difference (%) in FIG. 10(b). This can confirm that the effect of the Hct is reduced when the blood component amount is measured for each of the blood samples with different Hct values, and thus the accuracy of the measured blood component amount is improved.

Figure 13:
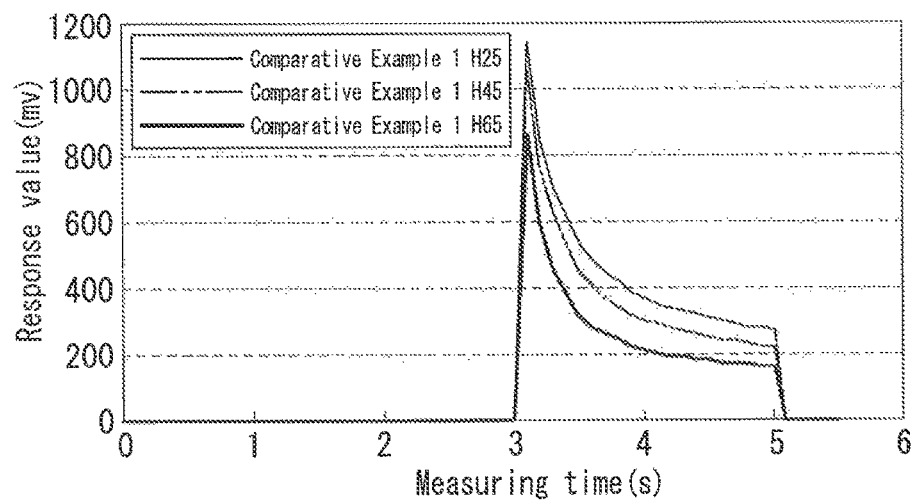
FIG. 13 shows the results of blood samples in which a blood component (glucose) concentration is 300 mg/dl.
Figure 13:
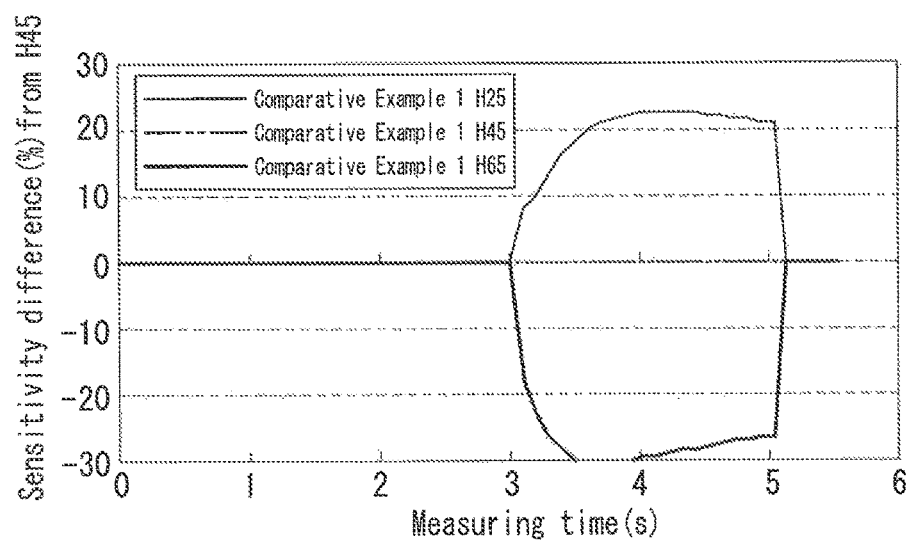

FIG. 13 shows the results of the blood samples in which the blood component (glucose) concentration is 300 mg/dl. FIG. 13(a) is a graph showing changes in the response current value (mV) over time with respect to the applied voltage (mV) in Comparative Example 1. FIG. 13(b) is a graph showing changes in the sensitivity difference (%) over time with respect to the applied voltage (mV) in Comparative Example 1. Specifically, using the blood sample with an Hct value of 45% as a reference, a calibration curve is obtained from the correspondence between the first current value and the blood component (glucose) concentration. FIG. 13(b) shows the sensitivity difference (%) from the true value when the calibration curve is applied to the blood sample with an Hct value of 25% and the blood sample with an Hct value of 65%.

Figure 14:
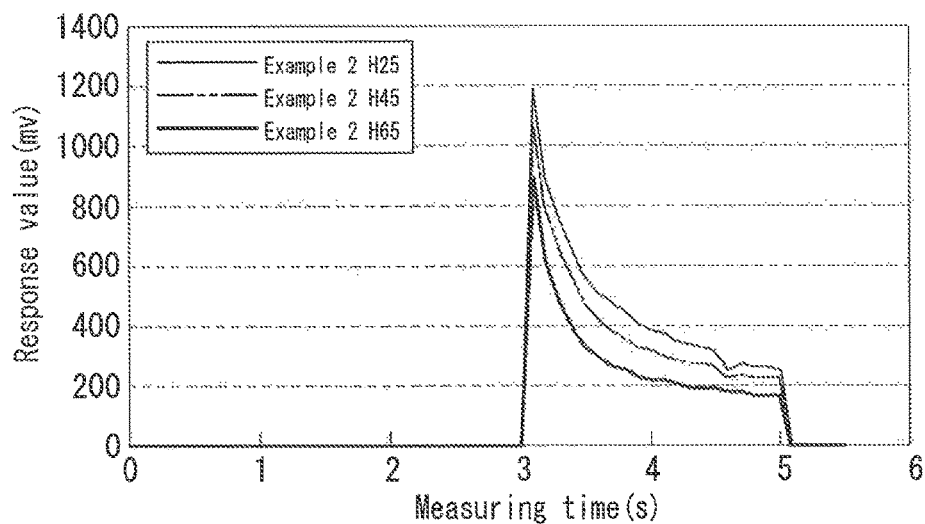
FIG. 14 shows the results of blood samples in which a blood component (glucose) concentration is 300 mg/dl.
Figure 14:
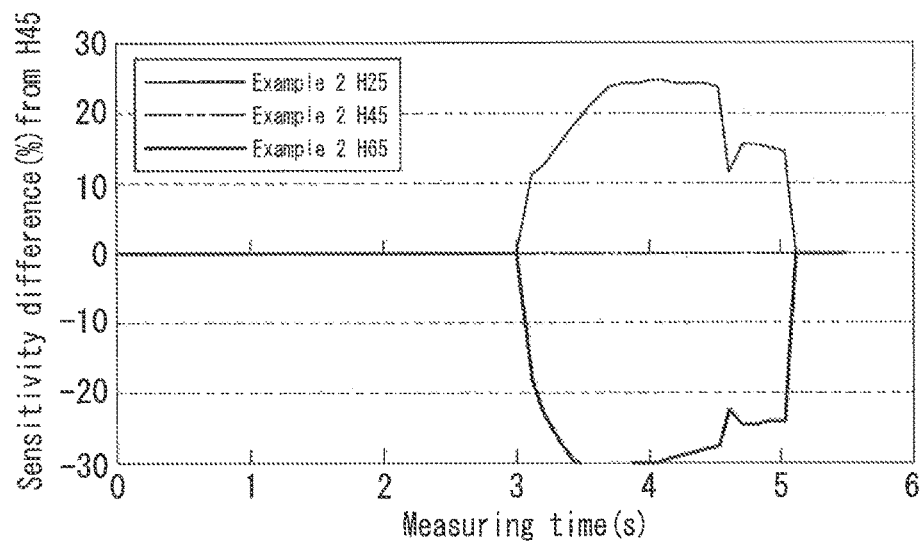

FIG. 14 shows the results of the blood samples in which the blood component (glucose) concentration is 300 mg/dl. FIG. 14(a) is a graph showing changes in the response current value (mV) over time with respect to the applied voltage (mV) in Example 2. FIG. 14(b) is a graph showing changes in the sensitivity difference (%) over time with respect to the applied voltage (mV) in Example 2. Specifically, using the blood sample with an Hct value of 45% as a reference, a calibration curve is obtained from the correspondence between the first current value and the blood component (glucose) concentration. FIG. 14(b) shows the sensitivity difference (%) from the true value when the calibration curve is applied to the blood sample with an Hct value of 25% and the blood sample with an Hct value of 65%.

Figure 15:
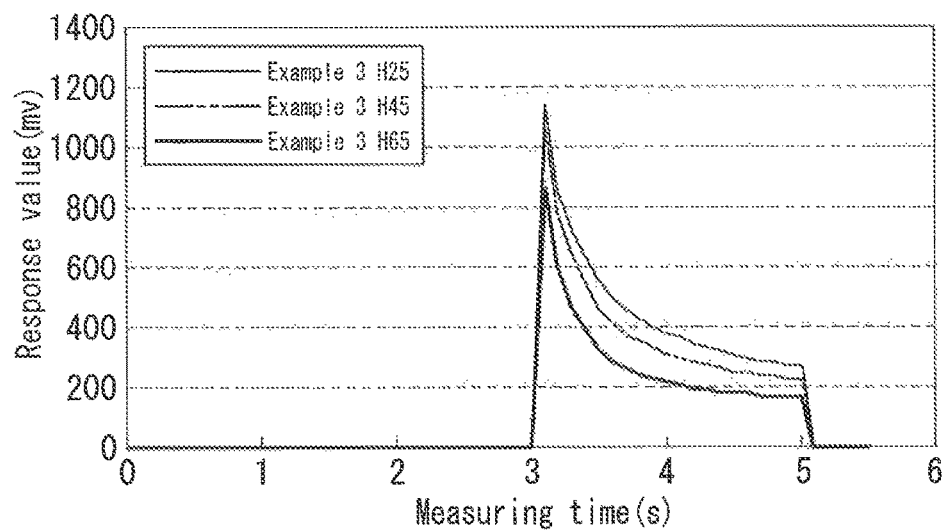
FIG. 15 shows the results of blood samples in which a blood component (glucose) concentration is 300 mg/dl.
Figure 15:
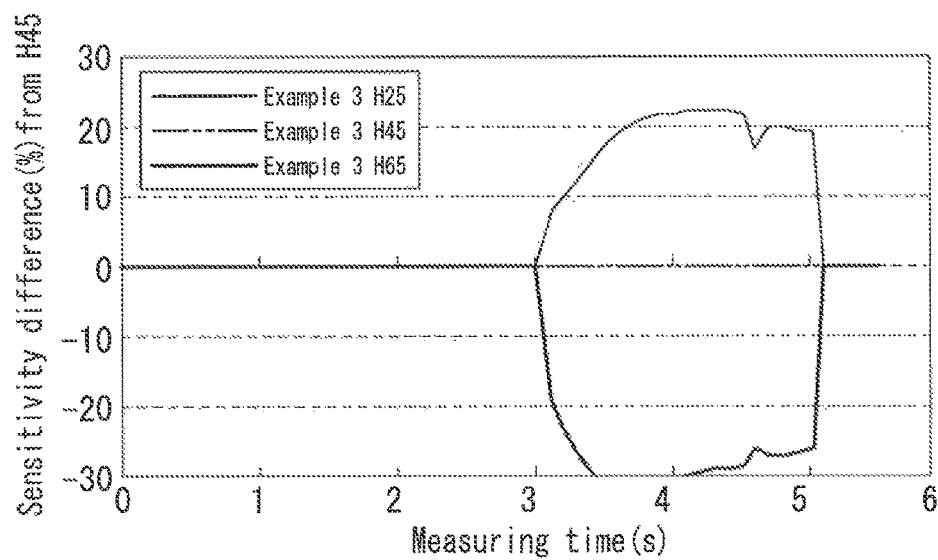

FIG. 15 shows the results of the blood samples in which the blood component (glucose) concentration is 300 mg/dl. FIG. 15(a) is a graph showing changes in the response current value (mV) over time with respect to the applied voltage (mV) in Example 3. FIG. 15(b) is a graph showing changes in the sensitivity difference (%) over time with respect to the applied voltage (mV) in Example 3. Specifically, using the blood sample with an Hct value of 45% as a reference, a calibration curve is obtained from the correspondence between the first current value and the blood component (glucose) concentration. FIG. 15(b) shows the sensitivity difference (%) from the true value when the calibration curve is applied to the blood sample with an Hct value of 25% and the blood sample with an Hct value of 65%. In FIGS. 13 to 15, "H25" represents the use of the blood sample with an Hct value of 25%, "H45" represents the use of the blood sample with an Hct value of 45%, and "H65" represents the use of the blood sample with an Hct value of 65%.

Compared to FIG. 13(a) and FIG. 13(b), in the measuring method of the present invention, as shown in FIG. 14(a) and FIG. 14(b), the sensitivity difference (%) after a measuring time of 4.5 seconds in FIG. 14(b) is smaller than the sensitivity difference (%) in FIG. 13(b). This can confirm that the effect of the Hct is reduced when the blood component amount is measured for each of the blood samples with different Hct values, and thus the accuracy of the measured blood component amount is improved. Moreover, compared to FIG. 13(a) and FIG. 13(b), in the measuring method of the present invention, as shown in FIG. 15(a) and FIG. 15(b), the sensitivity difference (%) after a measuring time of 4.5 seconds in FIG. 15(b) is smaller than the sensitivity difference (%) in FIG. 13(b). This can confirm that the effect of the Hct is reduced when the blood component amount is measured for each of the blood samples with different Hct values, and thus the accuracy of the measured blood component amount is improved.

Figure 16:
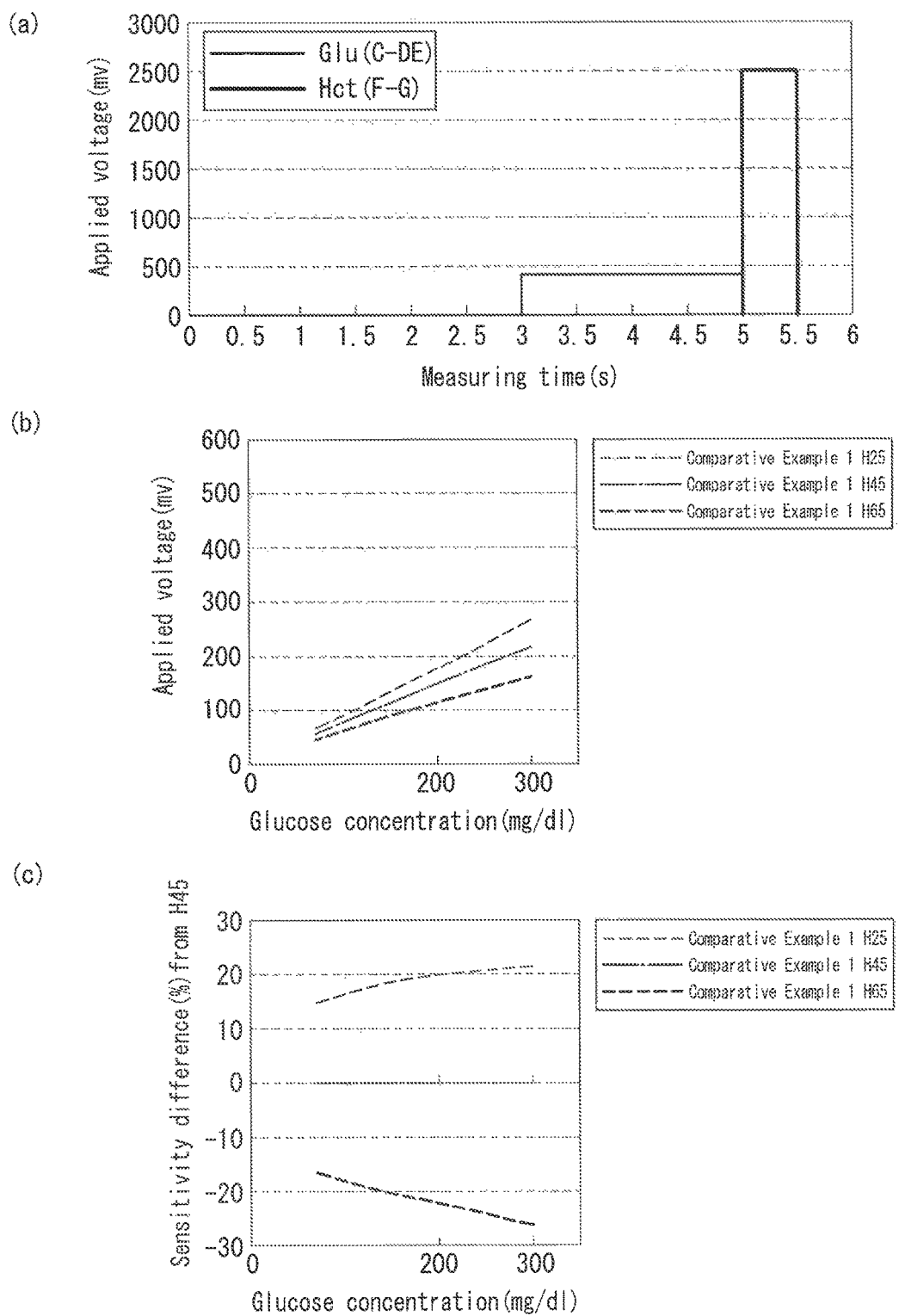
FIG. 16 is a summary of the results shown in FIGS. 7, 10, and 13.

FIG. 16 is a summary of the results shown in FIGS. 7, 10, and 13. FIG. 16(a) is a graph showing the relationship between the application time and the applied current. FIG. 16(b) is a graph showing changes in the blood component (glucose) concentration and the response current value (mV) over time when the application time is 5 seconds in Comparative Example 1. FIG. 16(c) is a graph showing the blood component (glucose) concentration and the sensitivity difference (%) when the application time is 5 seconds in Comparative Example 1.

Figure 17:
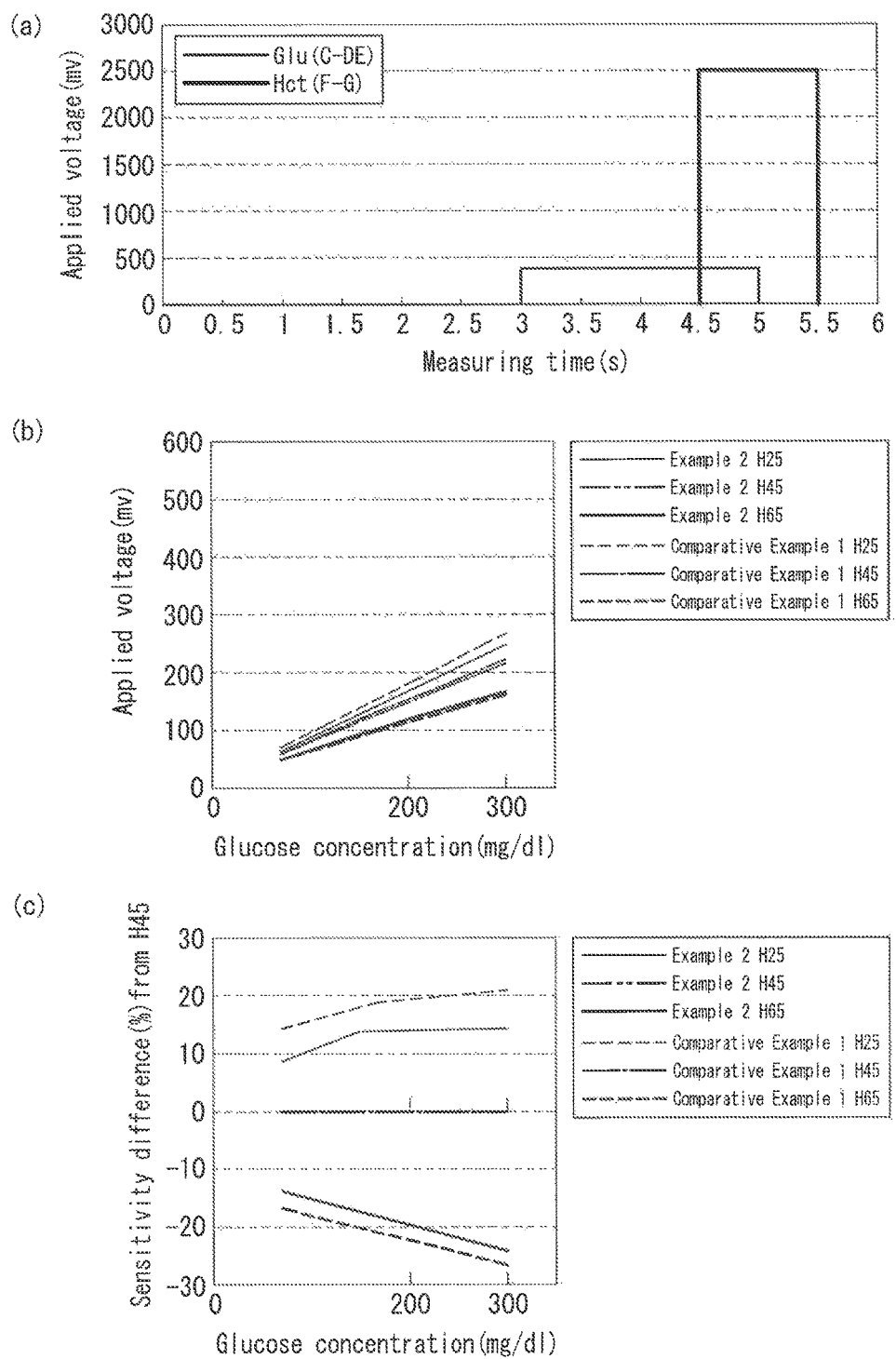
FIG. 17 is a summary of the results shown in FIGS. 8, 11, and 14.

FIG. 17 is a summary of the results shown in FIGS. 8, 11, and 14. FIG. 17(a) is a graph showing the relationship between the application time and the applied current. FIG. 17(b) is a graph showing changes in the blood component (glucose) concentration and the response current value (mV) over time when the application time is 5 seconds in Example 2. FIG. 17(c) is a graph showing the blood component (glucose) concentration and the sensitivity difference (%) when the application time is 5 seconds in Example 2.

Figure 18:
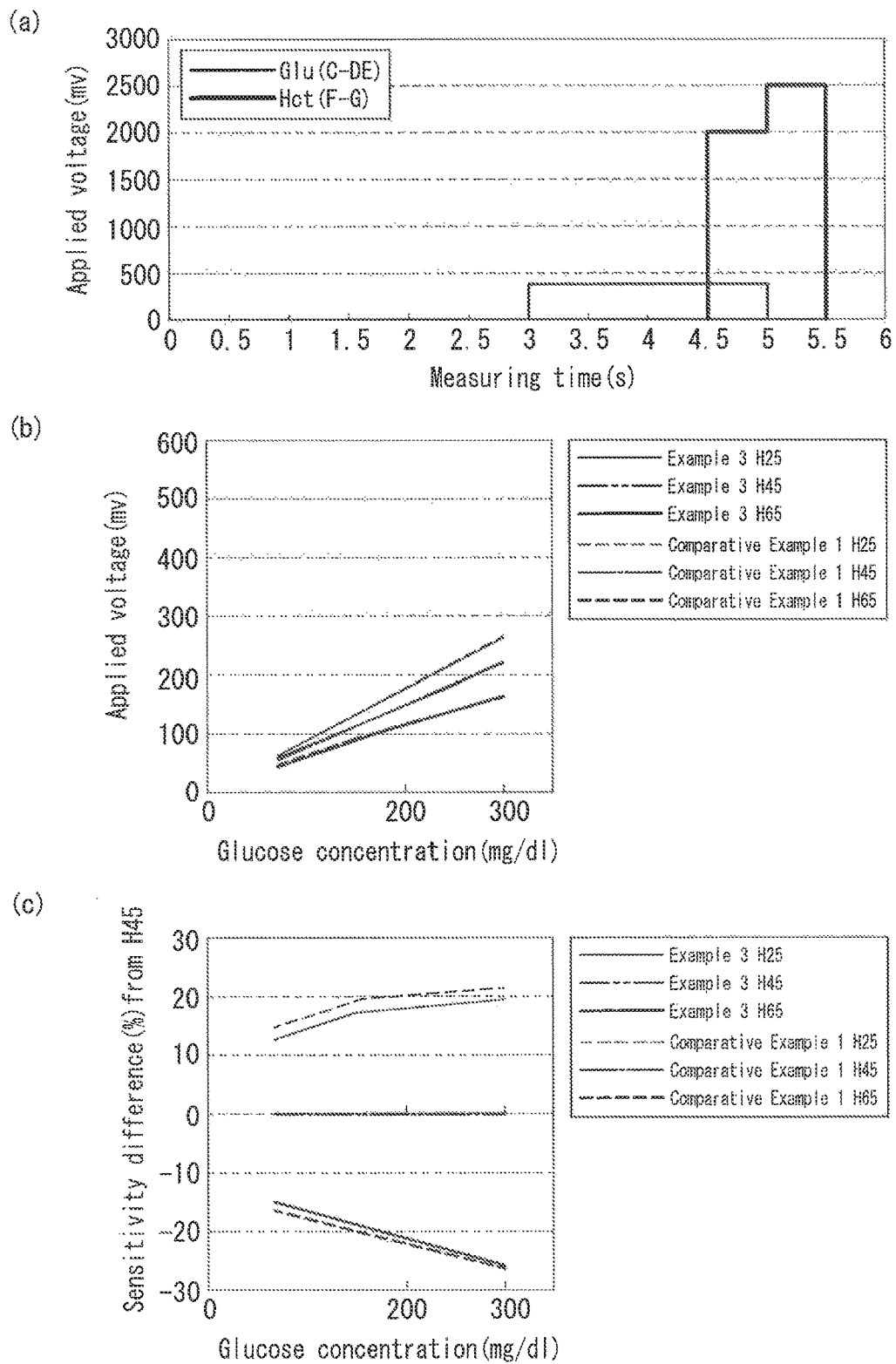
FIG. 18 is a summary of the results shown in FIGS. 9, 12, and 15.

FIG. 18 is a summary of the results shown in FIGS. 9, 12, and 15. FIG. 18(a) is a graph showing the relationship between the application time and the applied current. FIG. 18(b) is a graph showing changes in the blood component (glucose) concentration and the response current value (mV) over time when the application time is 5 seconds in Example 3. FIG. 18(c) is a graph showing the blood component (glucose) concentration and the sensitivity difference (%) when the application time is 5 seconds in Example 3.

As shown in FIGS. 16(a) to 16(c), FIGS. 17(a) to 17(c), and FIGS. 18(a) to 18(c), in the measuring method of the present invention, the absolute value of the sensitivity difference (%) in Examples is small compared to the sensitivity difference (%) in Comparative Example in FIGS. 16(c), 17(c), and 18(c). This can confirm that the effect of the Hct is reduced when the blood component amount is measured for each of the blood samples with different Hct values, and thus the accuracy of the measured blood component amount is improved.

Figure 19:
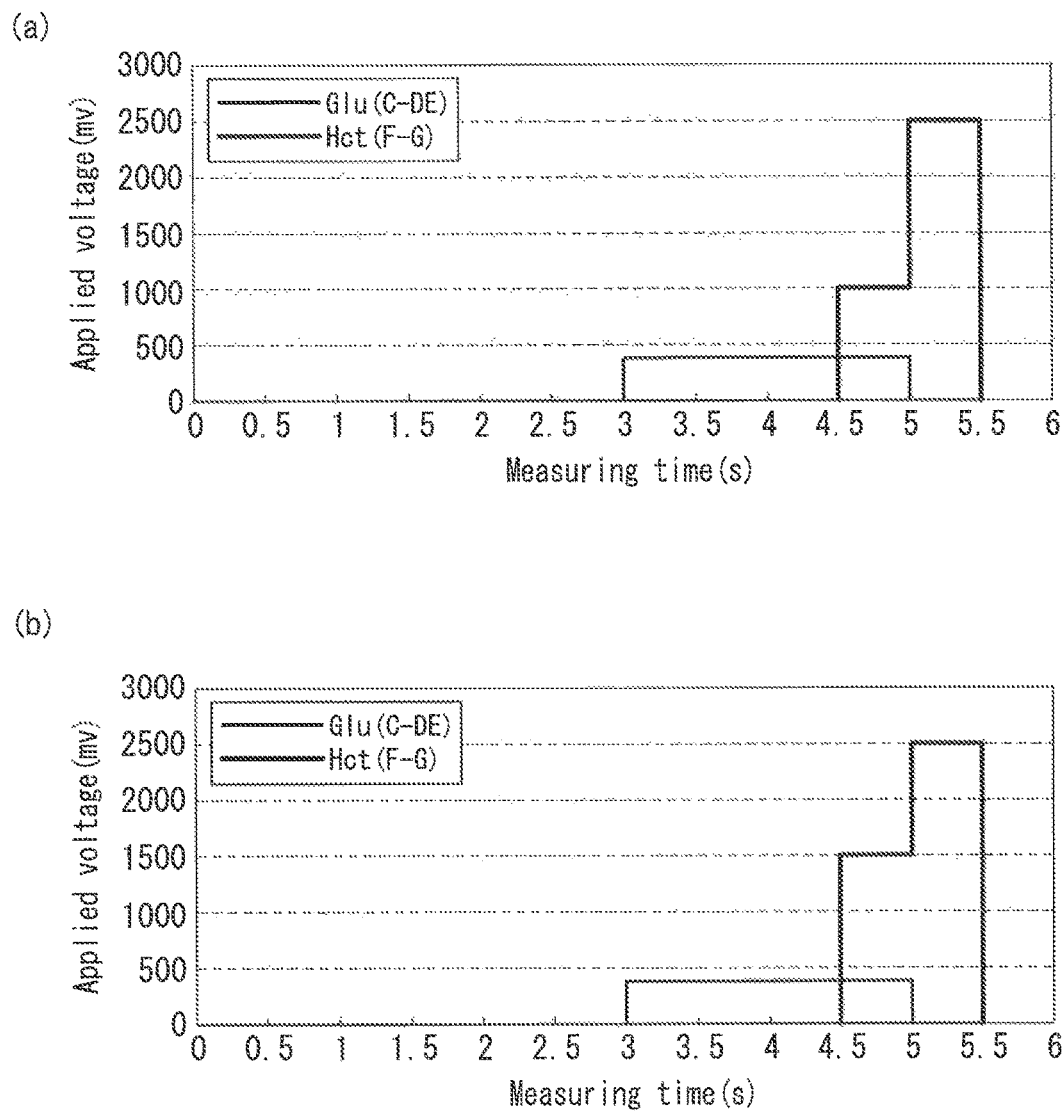
FIG. 19(a) and FIG. 19(b) are graphs showing the relationship between an application time and an applied current in another aspect of the present invention.

FIG. 19(a) and FIG. 19(b) are graphs showing the relationship between the application time and the applied current in another aspect of the present invention. In FIG. 19(a), a current flows through both of the electrodes of the sensor under the following conditions: the first voltage is 400 mV and the application time of the first voltage is from 3 to 5 seconds; the second voltage is 1000 mV and the application time of the second voltage is from 4.5 to 5 seconds; and the third voltage is 2500 mV and the application time of the third voltage is from 5 to 5.5 seconds. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds.

In FIG. 19(b), a current flows through both of the electrodes of the sensor under the following conditions: the first voltage is 400 mV and the application time of the first voltage is from 3 to 5 seconds; the second voltage is 1500 mV and the application time of the second voltage is from 4.5 to 5 seconds; and the third voltage is 2500 mV and the application time of the third voltage is from 5 to 5.5 seconds. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds.

EXAMPLE 4

In this example, a response current value and a sensitivity difference in the measurement of the Hct value are determined in the same manner as Example 2, except that using a sensor that includes the electrode C as the working electrode of the first electrode system, the electrode D and the electrode E as the counter electrode of the first electrode system, the electrode F as the working electrode of the second electrode system, the electrode A as the counter electrode of the second electrode system, the electrode F as the working electrode of a third electrode system, and the electrode G as the counter electrode of the third electrode system, a current flowing through both of the electrodes of the sensor is measured under the following conditions: the first voltage is 400 mV and the application time of the first voltage is from 3 to 5 seconds; the second voltage is 2000 mV and the application time of the second voltage is from 4.5 to 5 seconds; and the third voltage is 2500 mV and the application time of the third voltage is from 5 to 5.5 seconds (see FIG. 20(a)). In FIG. 20(a), "Glu (C-DE)" represents the application of the voltage to the first electrode system, "Hct (F-A)" represents the application of the voltage to the second electrode system, and "Hct (F-G)" represents the application of the voltage to the third electrode system. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds. The reagent layer 11 is arranged to cover a part of the electrodes C, D, E, and G. In this example, the third voltage is applied to the third electrode system instead of applying the third voltage to the second electrode system in the second step.

Figure 20:
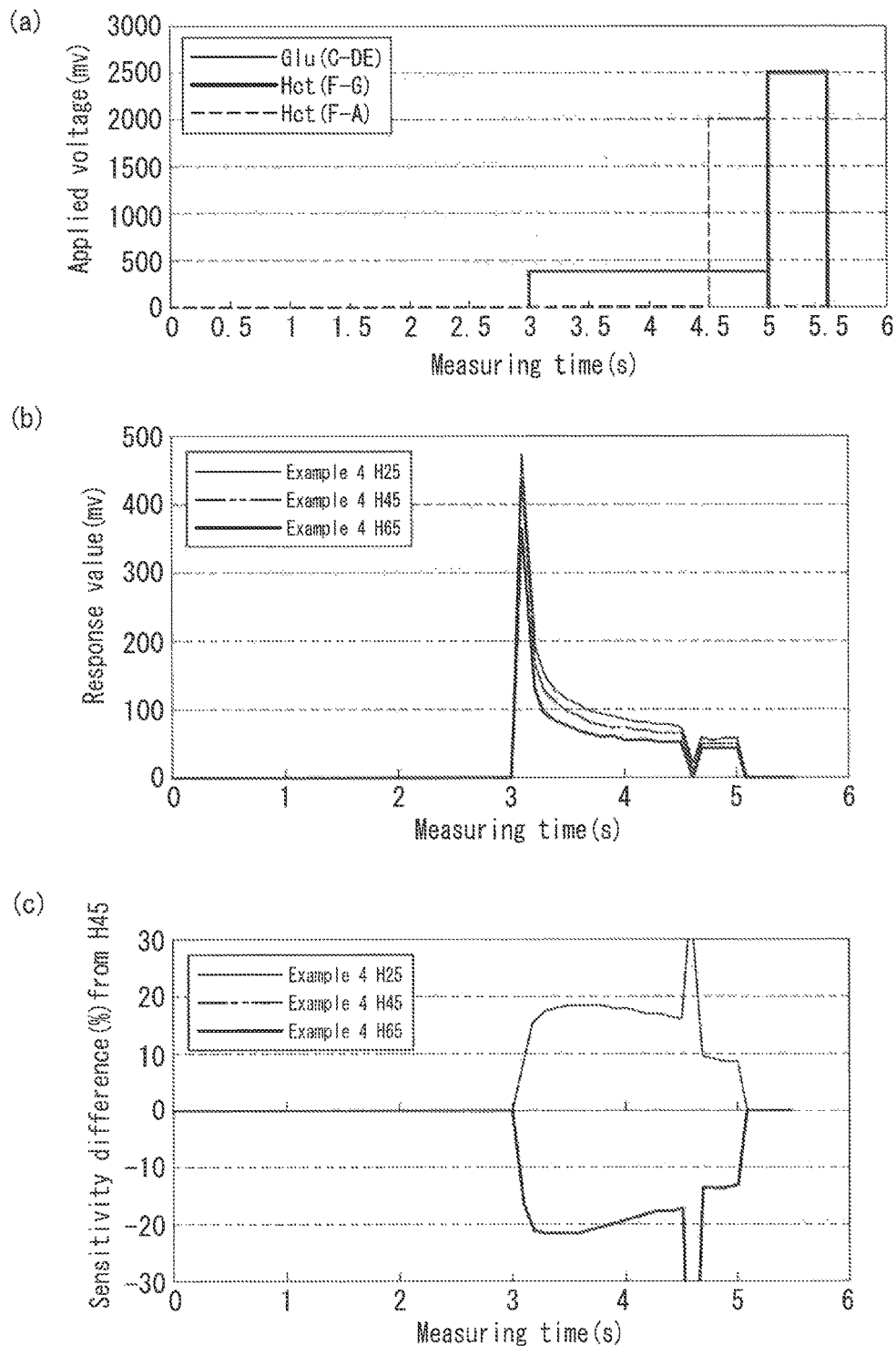
FIG. 20 shows the results of blood samples in which a blood component (glucose) concentration is 75 mg/dl.

FIG. 20 shows the results of the blood samples in which the blood component (glucose) concentration is 75 mg/dl. FIG. 20(a) is a graph showing the relationship between the application time and the applied current. FIG. 20(b) is a graph showing changes in the response current value (mV) over time with respect to the applied voltage (mV) in Example 4. FIG. 20(c) is a graph showing changes in the sensitivity difference (%) over time with respect to the applied voltage (mV) in Example 4. Specifically, using the blood sample with an Hct value of 45% as a reference, a calibration curve is obtained from the correspondence between the first current value and the blood component (glucose) concentration. FIG. 20(c) shows the sensitivity difference (%) from the true value when the calibration curve is applied to the blood sample with an Hct value of 25% and the blood sample with an Hct value of 65%.

Compared to FIG. 7(a) and FIG. 7(b), in the measuring method of the present invention, as shown in FIG. 20(b) and FIG. 20(c), the sensitivity difference (%) after a measuring time of 4.5 seconds in FIG. 20(b) is smaller than the sensitivity difference (%) in FIG. 7(b). This can confirm that the effect of the Hct is reduced when the blood component amount is measured for each of the blood samples with different Hct values, and thus the accuracy of the measured blood component amount is improved.

Figure 21:
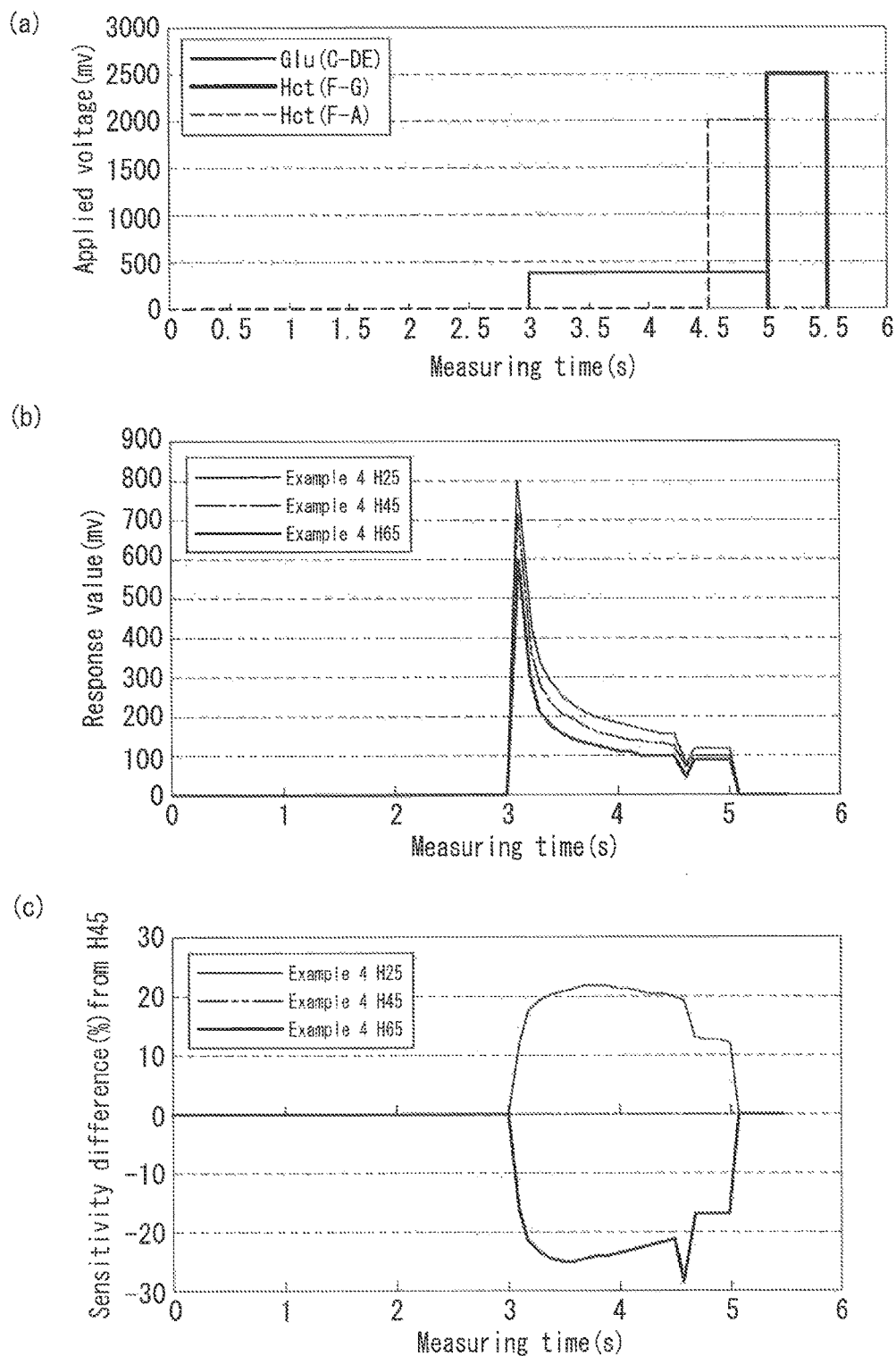
FIG. 21 shows the results of blood samples in which a blood component (glucose) concentration is 150 mg/dl.

FIG. 21 shows the results of the blood samples in which the blood component (glucose) concentration is 150 mg/dl. FIG. 21(a) is a graph showing the relationship between the application time and the applied current. FIG. 21(b) is a graph showing changes in the response current value (mV) over time with respect to the applied voltage (mV) in Example 4. FIG. 21(c) is a graph showing changes in the sensitivity difference (%) over time with respect to the applied voltage (mV) in Example 4. Specifically, using the blood sample with an Hct value of 45% as a reference, a calibration curve is obtained from the correspondence between the first current value and the blood component (glucose) concentration. FIG. 21(c) shows the sensitivity difference (%) from the true value when the calibration curve is applied to the blood sample with an Hct value of 25% and the blood sample with an Hct value of 65%.

Compared to FIG. 10(a) and FIG. 10(b), in the measuring method of the present invention, as shown in FIG. 21(b) and FIG. 21(c), the sensitivity difference (%) after a measuring time of 4.5 seconds in FIG. 21(b) is smaller than the sensitivity difference (%) in FIG. 10(b). This can confirm that the effect of the Hct is reduced when the blood component amount is measured for each of the blood samples with different Hct values, and thus the accuracy of the measured blood component amount is improved.

Figure 22:
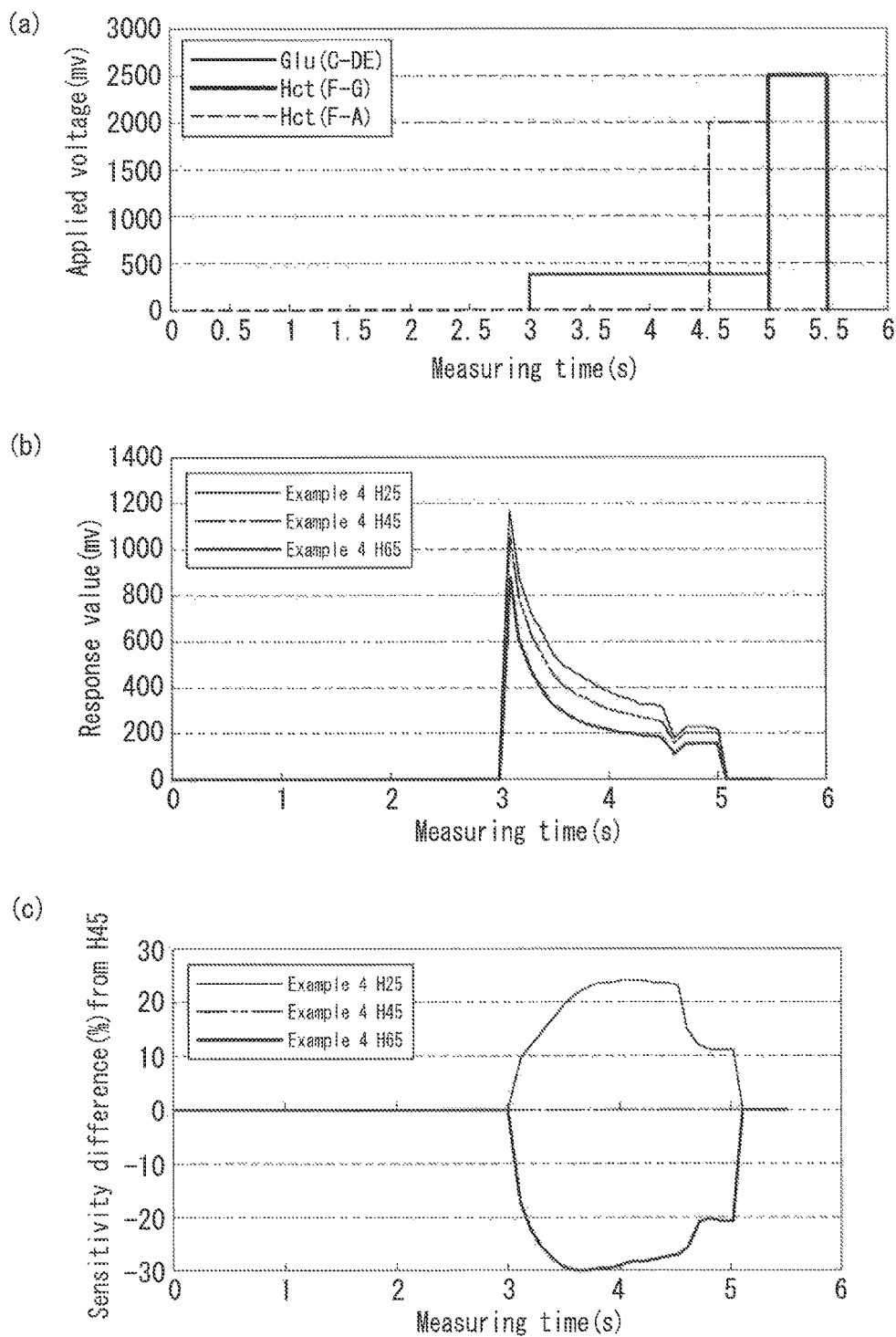
FIG. 22 shows the results of blood samples in which a blood component (glucose) concentration is 300 mg/dl.

FIG. 22 shows the results of the blood samples in which the blood component (glucose) concentration is 300 mg/dl. FIG. 22(a) is a graph showing the relationship between the application time and the applied current. FIG. 22(b) is a graph showing changes in the response current value (mV) over time with respect to the applied voltage (mV) in Example 4. FIG. 22(c) is a graph showing changes in the sensitivity difference (%) over time with respect to the applied voltage (mV) in Example 4. Specifically, using the blood sample with an Hct value of 45% as a reference, a calibration curve is obtained from the correspondence between the first current value and the blood component (glucose) concentration. FIG. 22(c) shows the sensitivity difference (%) from the true value when the calibration curve is applied to the blood sample with an Hct value of 25% and the blood sample with an Hct value of 65%.

Compared to FIG. 13(a) and FIG. 13(b), in the measuring method of the present invention, as shown in FIG. 22(b) and FIG. 22(c), the sensitivity difference (%) after a measuring time of 4.5 seconds in FIG. 22(b) is smaller than the sensitivity difference (%) in FIG. 13(b). This can confirm that the effect of the Hct is reduced when the blood component amount is measured for each of the blood samples with different Hct values, and thus the accuracy of the measured blood component amount is improved.

Figure 23:
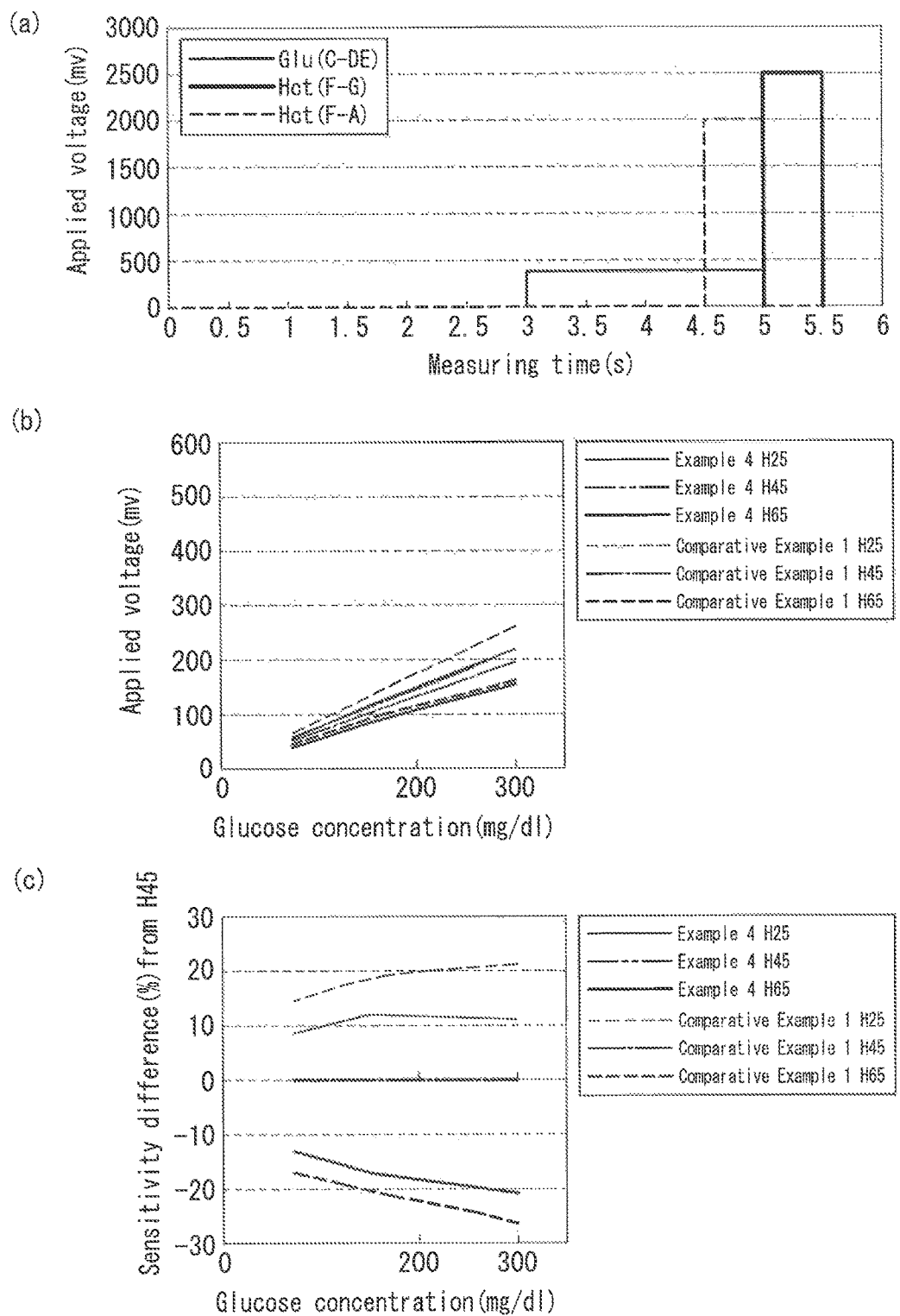
FIG. 23 is a summary of the results shown in FIGS. 20, 21, and 22.

FIG. 23 is a summary of the results shown in FIGS. 20, 21, and 22. FIG. 23(a) is a graph showing the relationship between the application time and the applied current. FIG. 23(b) is a graph showing changes in the blood component (glucose) concentration and the response current value (mV) over time when the application time is 5 seconds in Example 4. FIG. 23(c) is a graph showing the blood component (glucose) concentration and the sensitivity difference (%) when the application time is 5 seconds in Example 4.

As shown in FIGS. 23(a) to 23(c), in the measuring method of the present invention, the absolute value of the sensitivity difference (%) in Example 4 is small compared to the sensitivity difference (%) in Comparative Example in FIG. 23(c). This can confirm that the effect of the Hct is reduced when the blood component amount is measured for each of the blood samples with different Hct values, and thus the accuracy of the measured blood component amount is improved.

Figure 24:
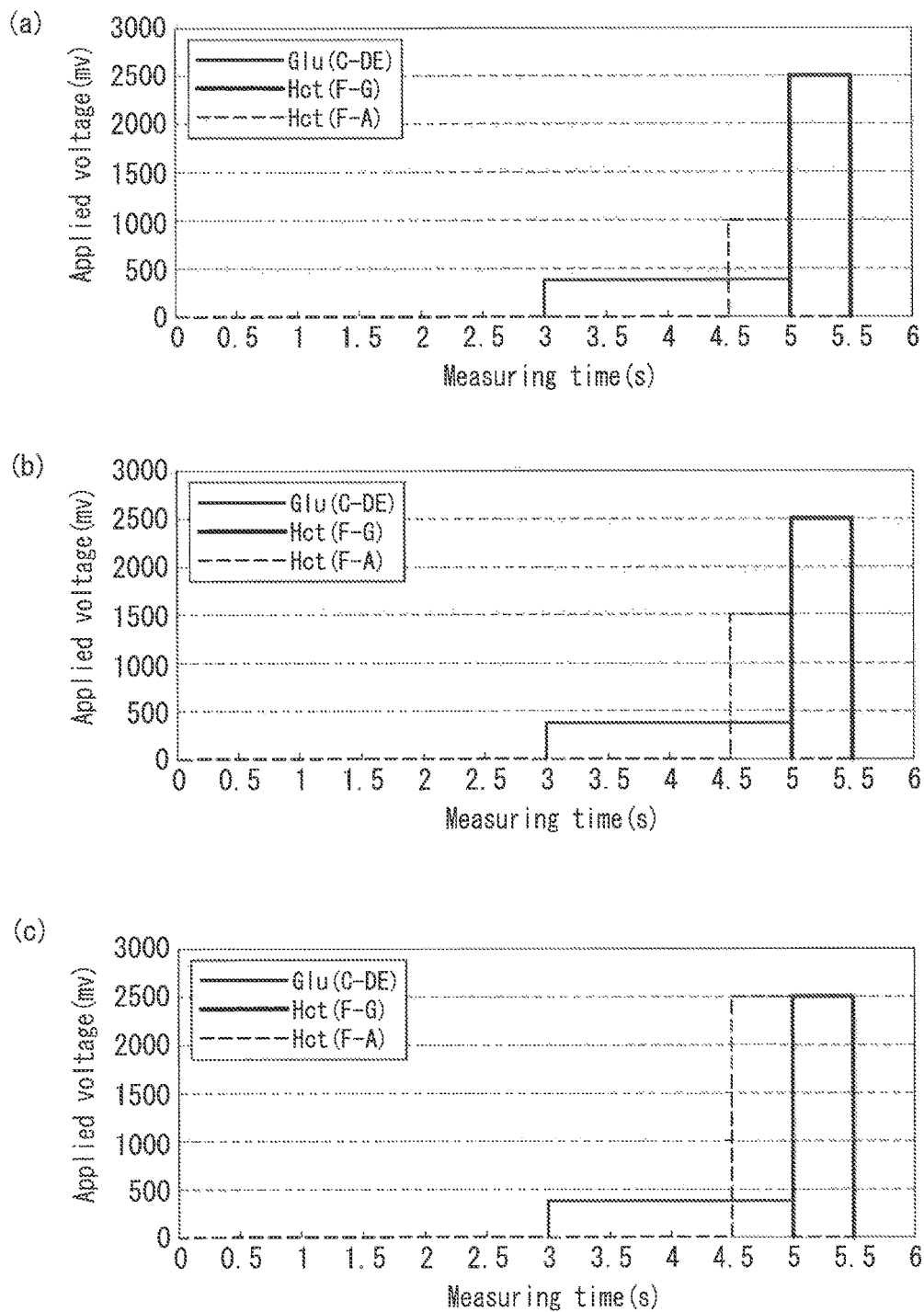
FIGS. 24(a), 24(b), and 24(c) are graphs showing the relationship between an application time and an applied current in another aspect of the present invention.

FIG. 24(a), FIG. 24(b), and FIG. 24(c) are graphs showing the relationship between the application time and the applied current in another aspect of the present invention. In FIG. 24(a), a current flows through both of the electrodes of the sensor under the following conditions: the first voltage is 400 mV and the application time of the first voltage is from 3 to 5 seconds; the second voltage is 1000 mV and the application time of the second voltage is from 4.5 to 5 seconds; and the third voltage is 2500 mV and the application time of the third voltage is from 5 to 5.5 seconds. In this case, the step 2 corresponds to a measuring time from 4.5 to 5 seconds, and the step 3 corresponds to a measuring time from 5 to 5.5 seconds. In FIG. 24, "Glu (C-DE)" represents the application of the voltage to the first electrode system, "Hct (F-G)" represents the application of the voltage to the second electrode system, and "Hct (F-A)" represents the application of the voltage to the third electrode system. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds.

In FIG. 24(b), a current flows through both of the electrodes of the sensor under the following conditions: the first voltage is 400 mV and the application time of the first voltage is from 3 to 5 seconds; the second voltage is 1500 mV and the application time of the second voltage is from 4.5 to 5 seconds; and the third voltage is 2500 mV and the application time of the third voltage is from 5 to 5.5 seconds. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds.

In FIG. 24(c), a current flows through both of the electrodes of the sensor under the following conditions: the first voltage is 400 mV and the application time of the first voltage is from 3 to 5 seconds; the second voltage is 2500 mV and the application time of the second voltage is from 4.5 to 5 seconds; and the third voltage is 2500 mV and the application time of the third voltage is from 5 to 5.5 seconds. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds.

EXAMPLE 5

In this example, a response current value and a sensitivity difference in the measurement of the Hct value are determined in the same manner as Example 2, except that using a sensor that includes the electrode C as the working electrode of the first electrode system, the electrode D, the electrode E, and the electrode G as the counter electrode of the first electrode system, the electrode F as the working electrode of the second electrode system, and the electrode D, the electrode E, and the electrode G as the counter electrode of the second electrode system, a current flowing through both of the electrodes of the sensor is measured under the following conditions: the first voltage is 400 mV and the application time of the first voltage is from 3 to 5 seconds; the second voltage is 1000 mV and the application time of the second voltage is from 4.5 to 5 seconds; and the third voltage is 2500 mV and the application time of the third voltage is from 5 to 5.5 seconds (see FIG. 25(a)). In FIG. 25(a), "Glu (C-DEG)" represents the application of the voltage to the first electrode system, and "Hct (F-DEG)" represents the application of the voltage to the second electrode system. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds. The reagent layer 11 is arranged to cover a part of the electrodes C, D, E, and G.

EXAMPLE 6

In this example, a response current value and a sensitivity difference in the measurement of the Hct value are determined in the same manner as Example 2, except that using a sensor that includes the electrode C as the working electrode of the first electrode system, the electrode D, the electrode E, and the electrode G as the counter electrode of the first electrode system, the electrode F as the working electrode of the second electrode system, and the electrode D, the electrode E, and the electrode G as the counter electrode of the second electrode system, a current flowing through both of the electrodes of the sensor is measured under the following conditions: the first voltage is 400 mV and the application time of the first voltage is from 3 to 5 seconds; the second voltage is 2000 mV and the application time of the second voltage is from 4.5 to 5 seconds; and the third voltage is 2500 mV and the application time of the third voltage is from 5 to 5.5 seconds (see FIG. 26(a)). In FIG. 26(a), "Glu (C-DEG)" represents the application of the voltage to the first electrode system, and "Hct (F-DEG)" represents the application of the voltage to the second electrode system. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds. The reagent layer 11 is arranged to cover a part of the electrodes C, D, E, and G.

Figure 25:
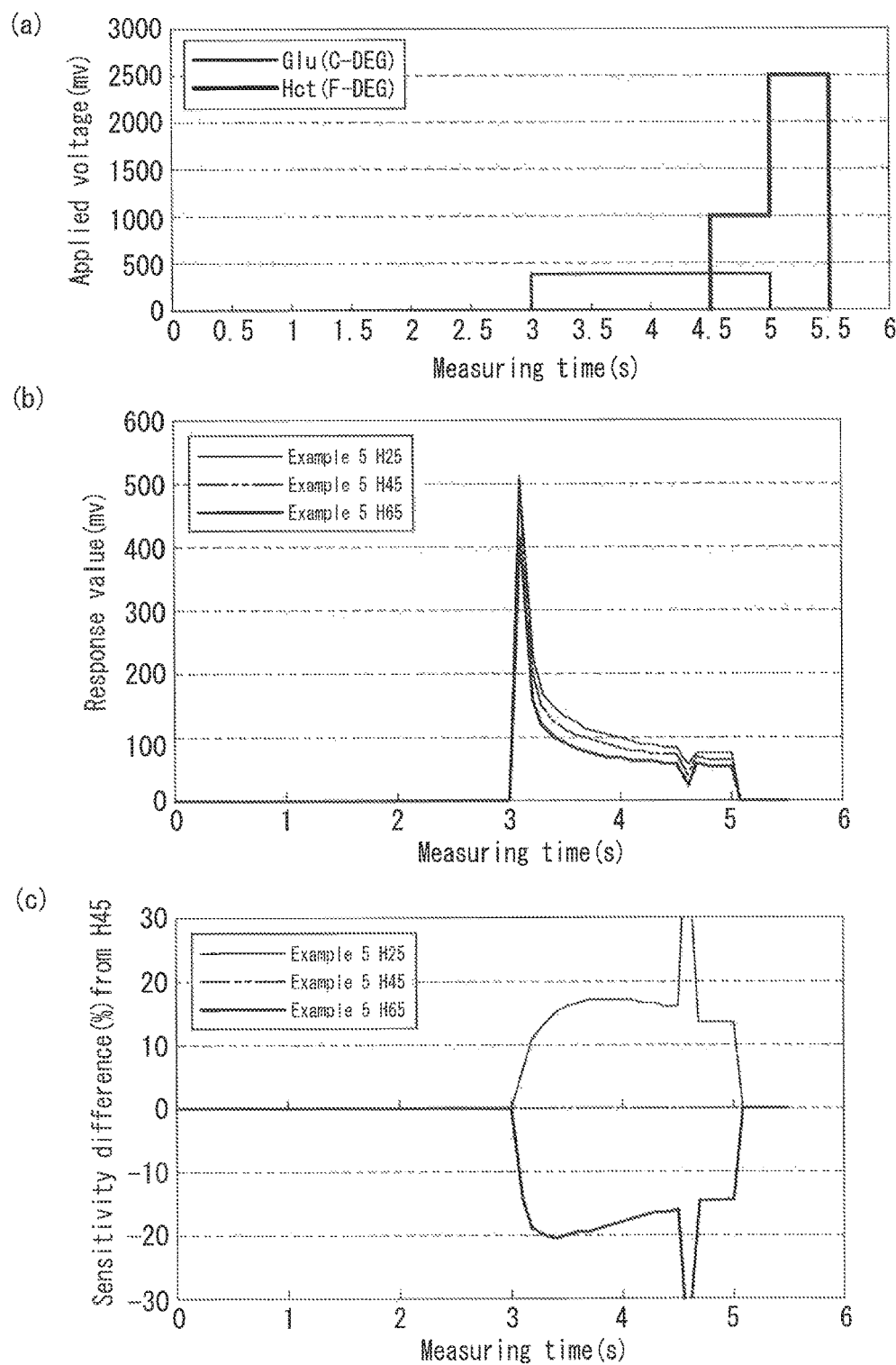
FIG. 25 shows the results of blood samples in which a blood component (glucose) concentration is 75 mg/dl.

FIG. 25 shows the results of the blood samples in which the blood component (glucose) concentration is 75 mg/dl. FIG. 25(a) is a graph showing the relationship between the application time and the applied current. FIG. 25(b) is a graph showing changes in the response current value (mV) over time with respect to the applied voltage (mV) in Example 5. FIG. 25(c) is a graph showing changes in the sensitivity difference (%) over time with respect to the applied voltage (mV) in Example 5. Specifically, using the blood sample with an Hct value of 45% as a reference, a calibration curve is obtained from the correspondence between the first current value and the blood component (glucose) concentration. FIG. 25(c) shows the sensitivity difference (%) from the true value when the calibration curve is applied to the blood sample with an Hct value of 25% and the blood sample with an Hct value of 65%.

Figure 26:
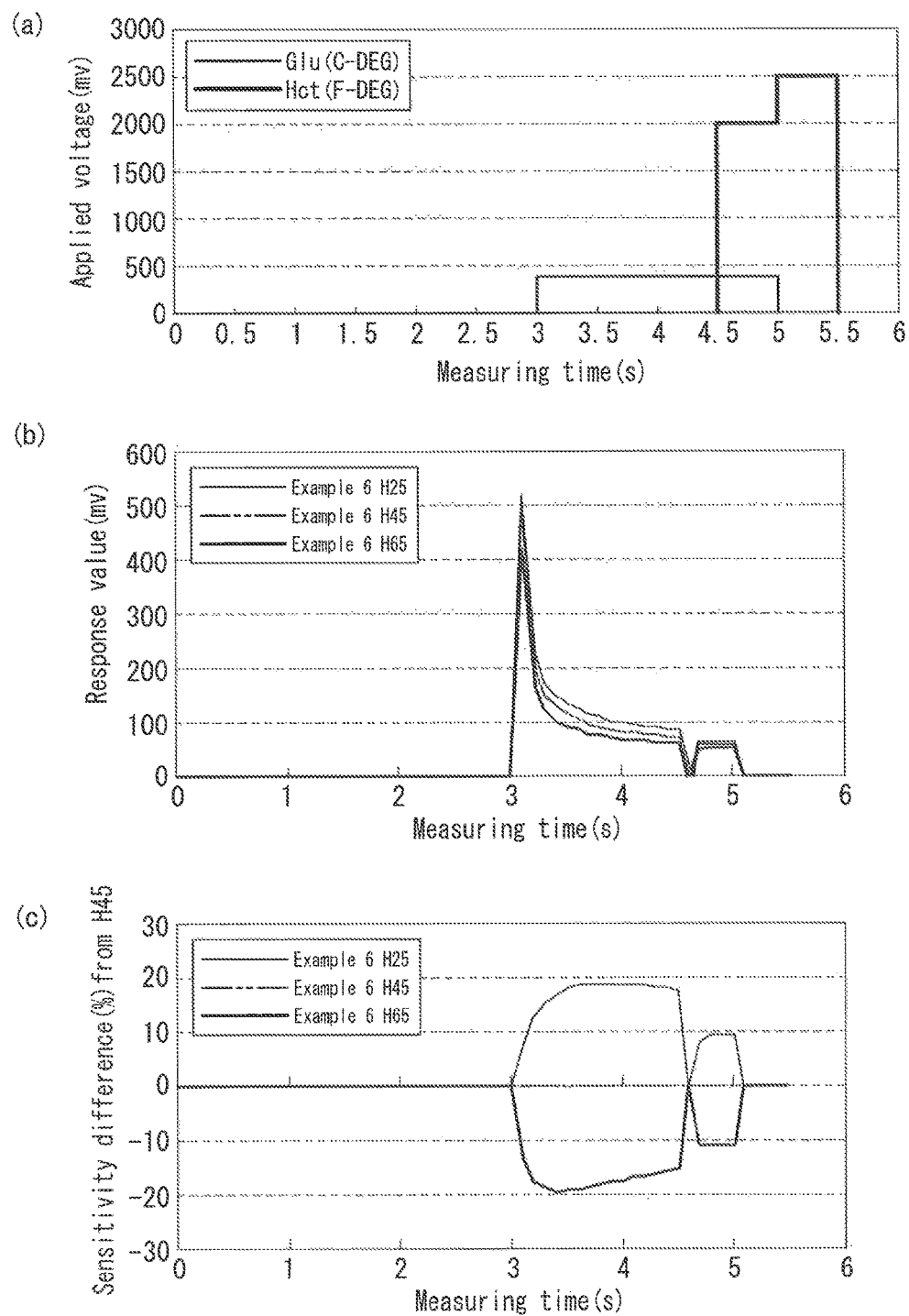
FIG. 26 shows the results of blood samples in which a blood component (glucose) concentration is 75 mg/dl.

FIG. 26 shows the results of the blood samples in which the blood component (glucose) concentration is 75 mg/dl.

FIG. 26(a) is a graph showing the relationship between the application time and the applied current. FIG. 26(b) is a graph showing changes in the response current value (mV) over time with respect to the applied voltage (mV) in Example 6. FIG. 26(c) is a graph showing changes in the sensitivity difference (%) over time with respect to the applied voltage (mV) in Example 6. Specifically, using the blood sample with an Hct value of 45% as a reference, a calibration curve is obtained from the correspondence between the first current value and the blood component (glucose) concentration. FIG. 26(c) shows the sensitivity difference (%) from the true value when the calibration curve is applied to the blood sample with an Hct value of 25% and the blood sample with an Hct value of 65%.

Compared to FIG. 7(a) and FIG. 7(b), in the measuring method of the present invention, as shown in FIG. 25(b) and FIG. 25(c), the sensitivity difference (%) after a measuring time of 4.5 seconds in FIG. 25(b) is smaller than the sensitivity difference (%) in FIG. 7(b). This can confirm that the effect of the Hct is reduced when the blood component amount is measured for each of the blood samples with different Hct values, and thus the accuracy of the measured blood component amount is improved. Moreover, compared to FIG. 7(a) and FIG. 7(b), in the measuring method of the present invention, as shown in FIG. 26(b) and FIG. 26(c), the sensitivity difference (%) after a measuring time of 4.5 seconds in FIG. 26(b) is smaller than the sensitivity difference (%) in FIG. 7(b). This can confirm that the effect of the Hct is reduced when the blood component amount is measured for each of the blood samples with different Hct values, and thus the accuracy of the measured blood component amount is improved.

Figure 27:
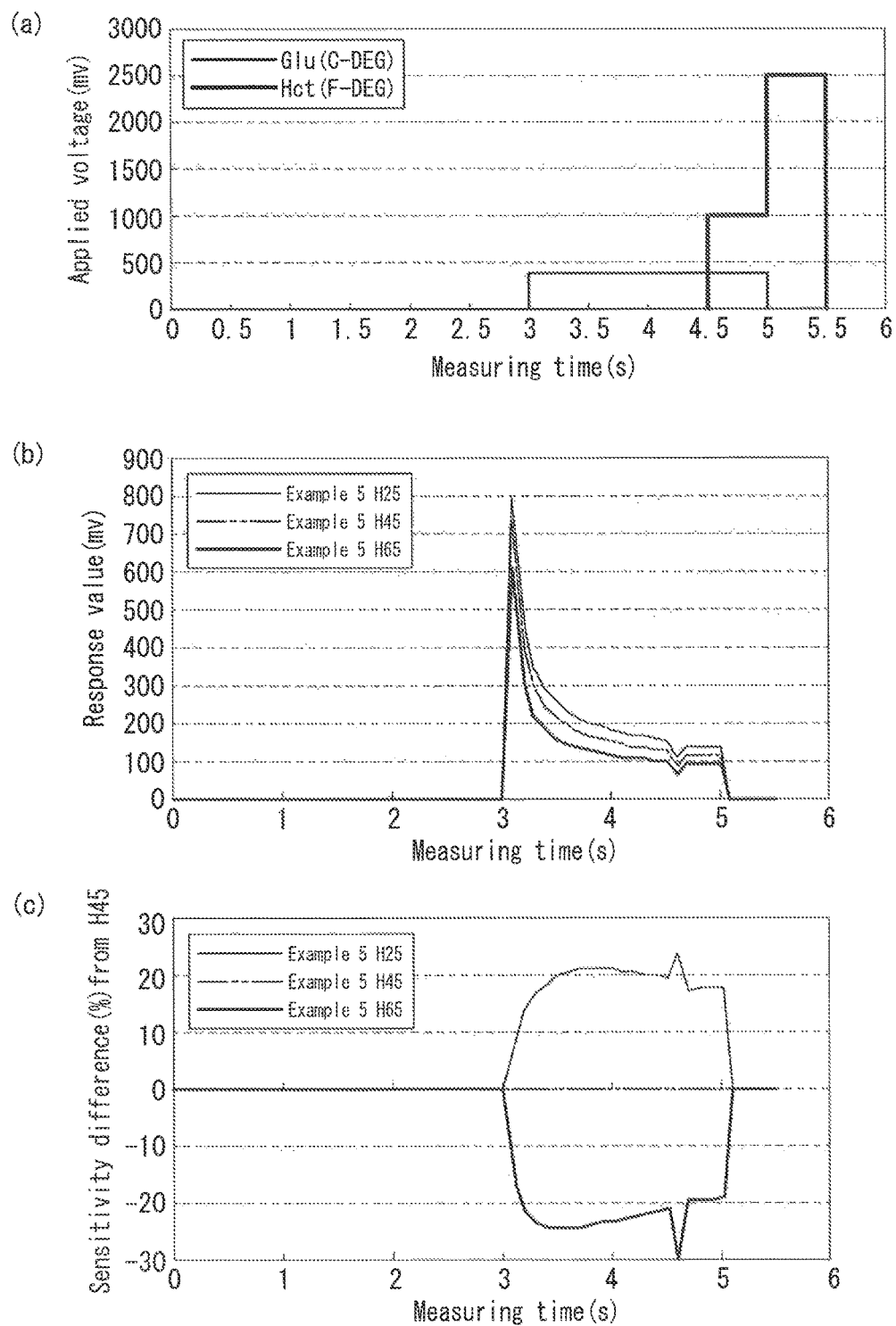
FIG. 27 shows the results of blood samples in which a blood component (glucose) concentration is 150 mg/dl.

FIG. 27 shows the results of the blood samples in which the blood component (glucose) concentration is 150 mg/dl. FIG. 27(a) is a graph showing the relationship between the application time and the applied current. FIG. 27(b) is a graph showing changes in the response current value (mV) over time with respect to the applied voltage (mV) in Example 5. FIG. 27(c) is a graph showing changes in the sensitivity difference (%) over time with respect to the applied voltage (mV) in Example 5. Specifically, using the blood sample with an Hct value of 45% as a reference, a calibration curve is obtained from the correspondence between the first current value and the blood component (glucose) concentration. FIG. 27(c) shows the sensitivity difference (%) from the true value when the calibration curve is applied to the blood sample with an Hct value of 25% and the blood sample with an Hct value of 65%.

Figure 28:
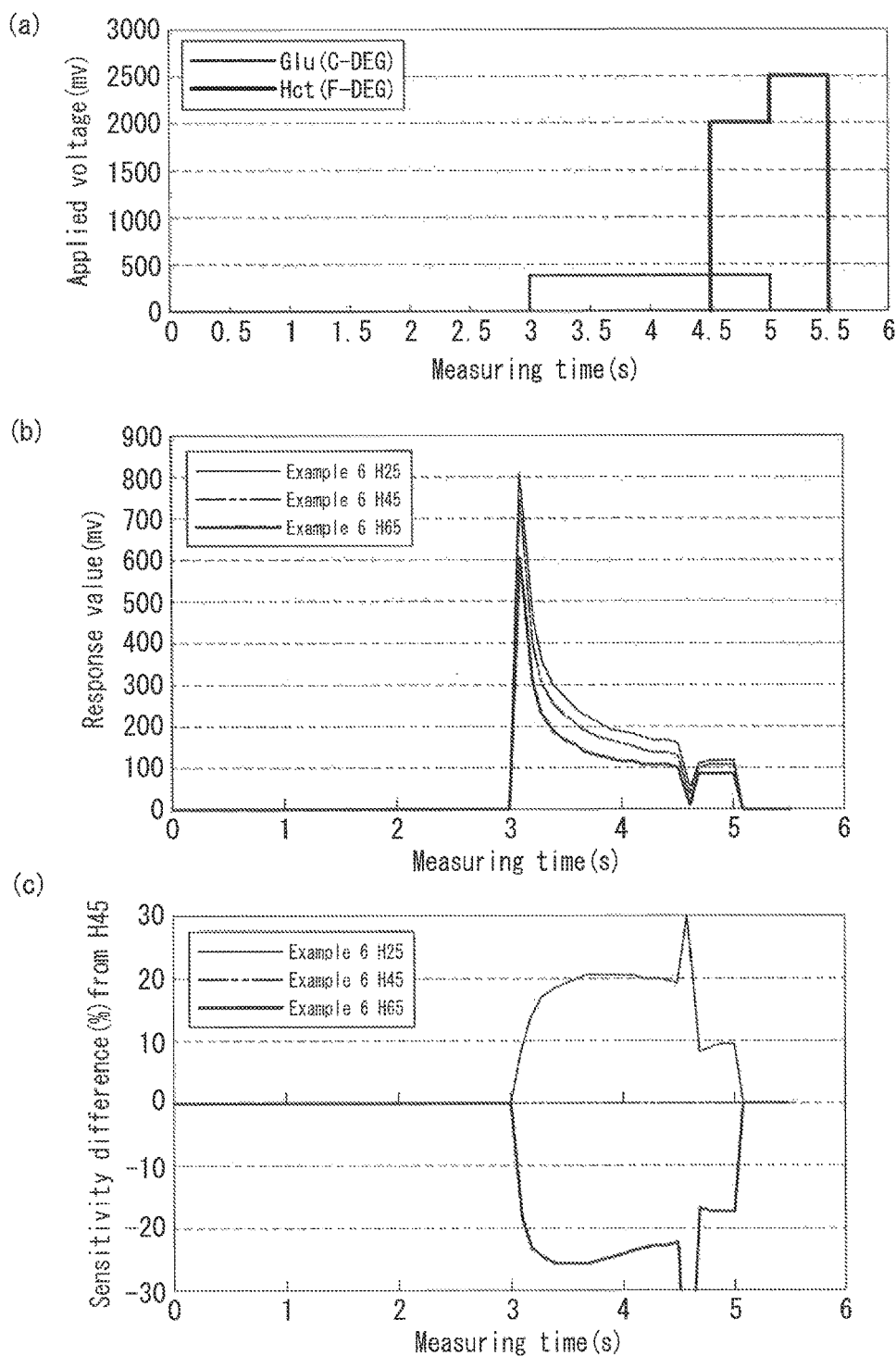
FIG. 28 shows the results of blood samples in which a blood component (glucose) concentration is 150 mg/dl.

FIG. 28 shows the results of the blood samples in which the blood component (glucose) concentration is 150 mg/dl. FIG. 28(a) is a graph showing the relationship between the application time and the applied current. FIG. 28(b) is a graph showing changes in the response current value (mV) over time with respect to the applied voltage (mV) in Example 6. FIG. 28(c) is a graph showing changes in the sensitivity difference (%) over time with respect to the applied voltage (mV) in Example 6. Specifically, using the blood sample with an Hct value of 45% as a reference, a calibration curve is obtained from the correspondence between the first current value and the blood component (glucose) concentration. FIG. 28(c) shows the sensitivity difference (%) from the true value when the calibration curve is applied to the blood sample with an Hct value of 25% and the blood sample with an Hct value of 65%.

Compared to FIG. 10(a) and FIG. 10(b), in the measuring method of the present invention, as shown in FIG. 27(b) and FIG. 27(c), the sensitivity difference (%) after a measuring time of 4.5 seconds in FIG. 27(b) is smaller than the sensitivity difference (%) in FIG. 10(b). This can confirm that the effect of the Hct is reduced when the blood component amount is measured for each of the blood samples with different Hct values, and thus the accuracy of the measured blood component amount is improved. Moreover, compared to FIG. 10(a) and FIG. 10(b), in the measuring method of the present invention, as shown in FIG. 28(b) and FIG. 28(c), the sensitivity difference (%) after a measuring time of 4.5 seconds in FIG. 28(b) is smaller than the sensitivity difference (%) in FIG. 10(b). This can confirm that the effect of the Hct is reduced when the blood component amount is measured for each of the blood samples with different Hct values, and thus the accuracy of the measured blood component amount is improved.

Figure 29:
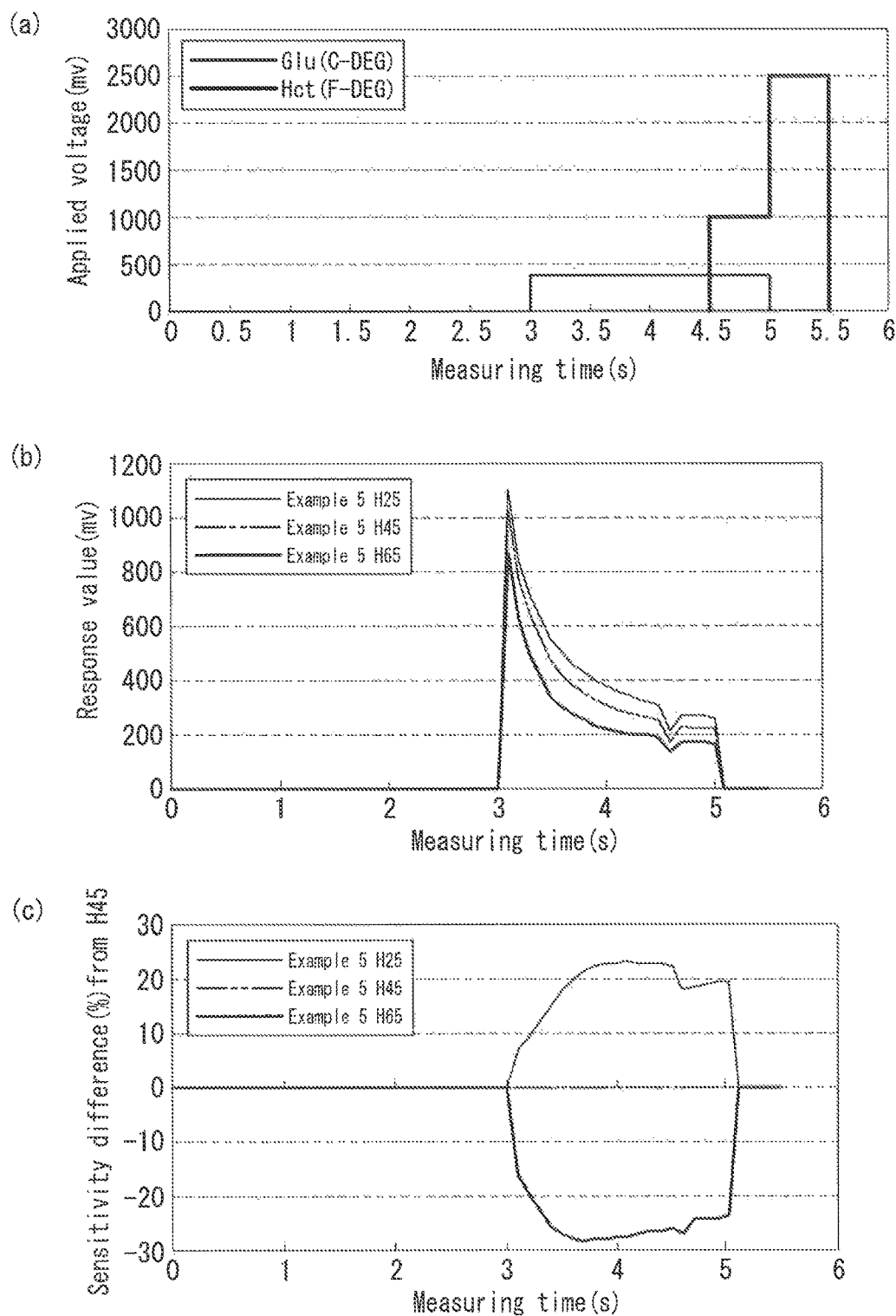
FIG. 29 shows the results of blood samples in which a blood component (glucose) concentration is 300 mg/dl.

FIG. 29 shows the results of the blood samples in which the blood component (glucose) concentration is 300 mg/dl. FIG. 29(a) is a graph showing the relationship between the application time and the applied current. FIG. 29(b) is a graph showing changes in the response current value (mV) over time with respect to the applied voltage (mV) in Example 5. FIG. 29(c) is a graph showing changes in the sensitivity difference (%) over time with respect to the applied voltage (mV) in Example 5. Specifically, using the blood sample with an Hct value of 45% as a reference, a calibration curve is obtained from the correspondence between the first current value and the blood component (glucose) concentration. FIG. 29(c) shows the sensitivity difference (%) from the true value when the calibration curve is applied to the blood sample with an Hct value of 25% and the blood sample with an Hct value of 65%.

Figure 30:
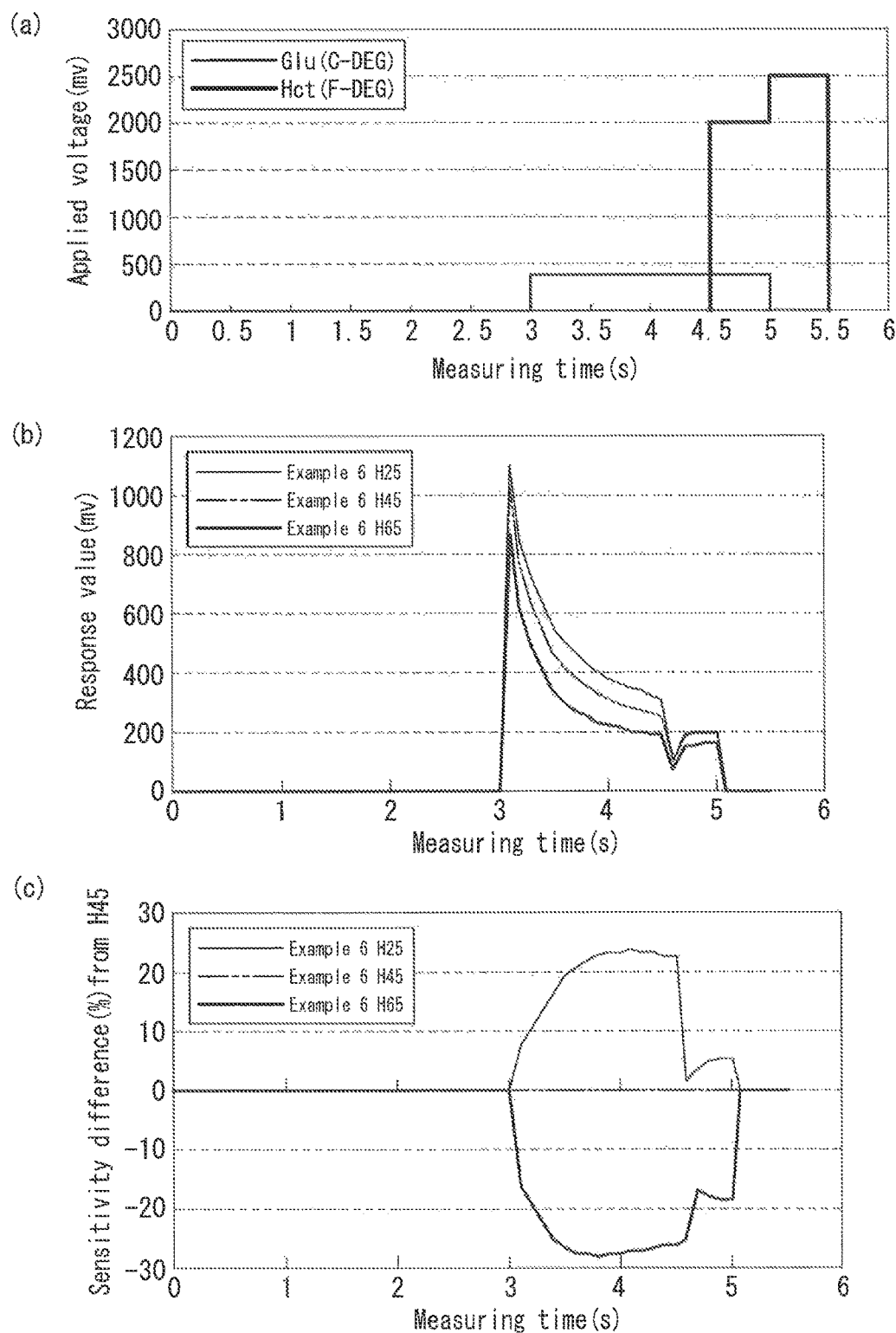
FIG. 30 shows the results of blood samples in which a blood component (glucose) concentration is 300 mg/dl.

FIG. 30 shows the results of the blood samples in which the blood component (glucose) concentration is 300 mg/dl. FIG. 30(a) is a graph showing the relationship between the application time and the applied current. FIG. 30(b) is a graph showing changes in the response current value (mV) over time with respect to the applied voltage (mV) in Example 6. FIG. 30(c) is a graph showing changes in the sensitivity difference (%) over time with respect to the applied voltage (mV) in Example 6. Specifically, using the blood sample with an Hct value of 45% as a reference, a calibration curve is obtained from the correspondence between the first current value and the blood component (glucose) concentration. FIG. 30(c) shows the sensitivity difference (%) from the true value when the calibration curve is applied to the blood sample with an Hct value of 25% and the blood sample with an Hct value of 65%.

Compared to FIG. 13(a) and FIG. 13(b), in the measuring method of the present invention, as shown in FIG. 29(b) and FIG. 29(c), the sensitivity difference (%) after a measuring time of 4.5 seconds in FIG. 29(b) is smaller than the sensitivity difference (%) in FIG. 13(b). This can confirm that the effect of the Hct is reduced when the blood component amount is measured for each of the blood samples with different Hct values, and thus the accuracy of the measured blood component amount is improved. Moreover, compared to FIG. 13(a) and FIG. 13(b), in the measuring method of the present invention, as shown in FIG. 30(b) and FIG. 30(c), the sensitivity difference (%) after a measuring time of 4.5 seconds in FIG. 30(b) is smaller than the sensitivity difference (%) in FIG. 13(b). This can confirm that the effect of the Hct is reduced when the blood component amount is measured for each of the blood samples with different Hct values, and thus the accuracy of the measured blood component amount is improved.

Figure 31:
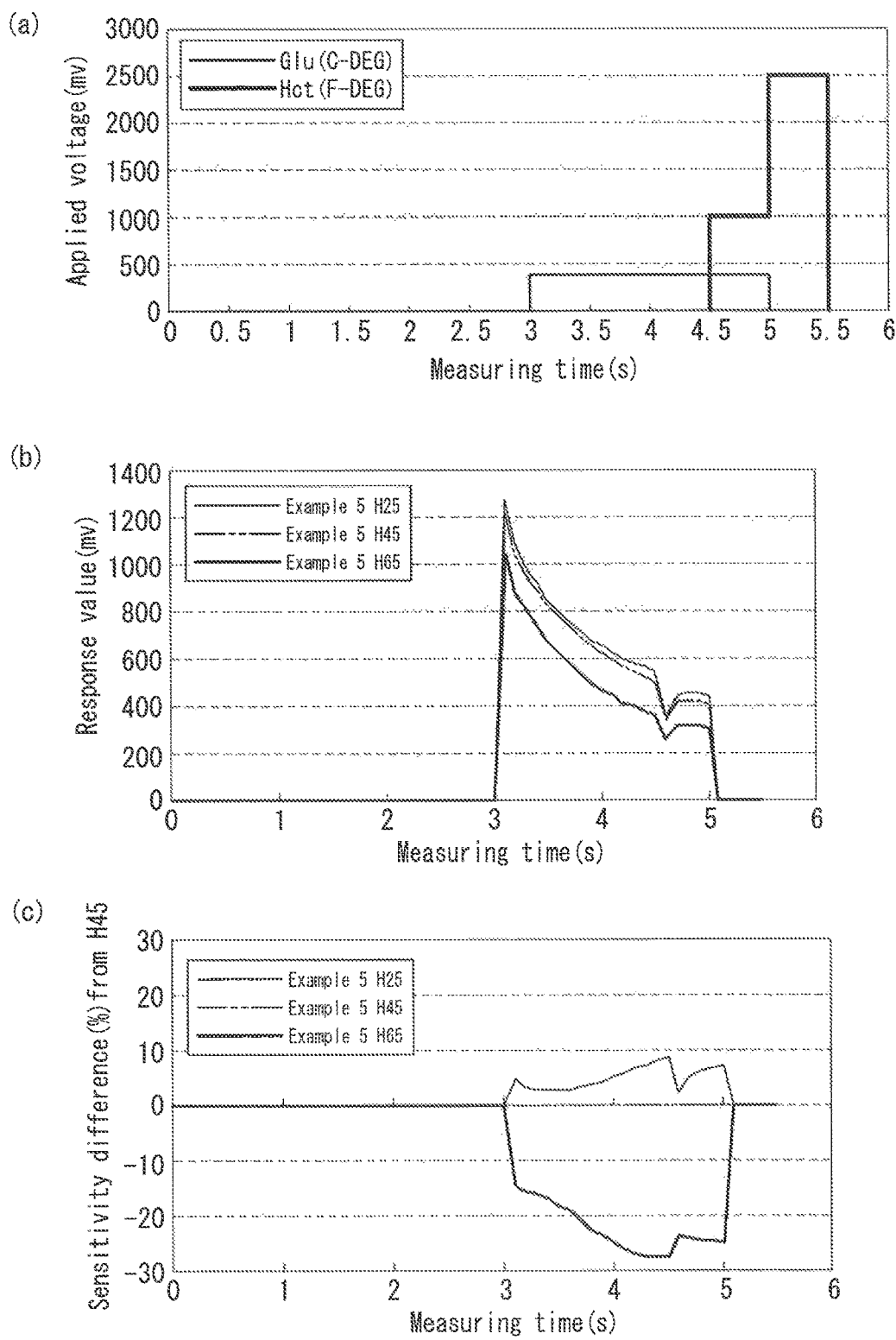
FIG. 31 shows the results of blood samples in which a blood component (glucose) concentration is 600 mg/dl.

FIG. 31 shows the results of the blood samples in which the blood component (glucose) concentration is 600 mg/dl.

FIG. 31(*a*) is a graph showing the relationship between the application time and the applied current. FIG. 31(*b*) is a graph showing changes in the response current value (mV) over time with respect to the applied voltage (mV) in Example 5. FIG. 31(*c*) is a graph showing changes in the sensitivity difference (%) over time with respect to the applied voltage (mV) in Example 5. Specifically, using the blood sample with an Hct value of 45% as a reference, a calibration curve is obtained from the correspondence between the first current value and the blood component (glucose) concentration. FIG. 31(*c*) shows the sensitivity difference (%) from the true value when the calibration curve is applied to the blood sample with an Hct value of 25% and the blood sample with an Hct value of 65%.

Figure 32:
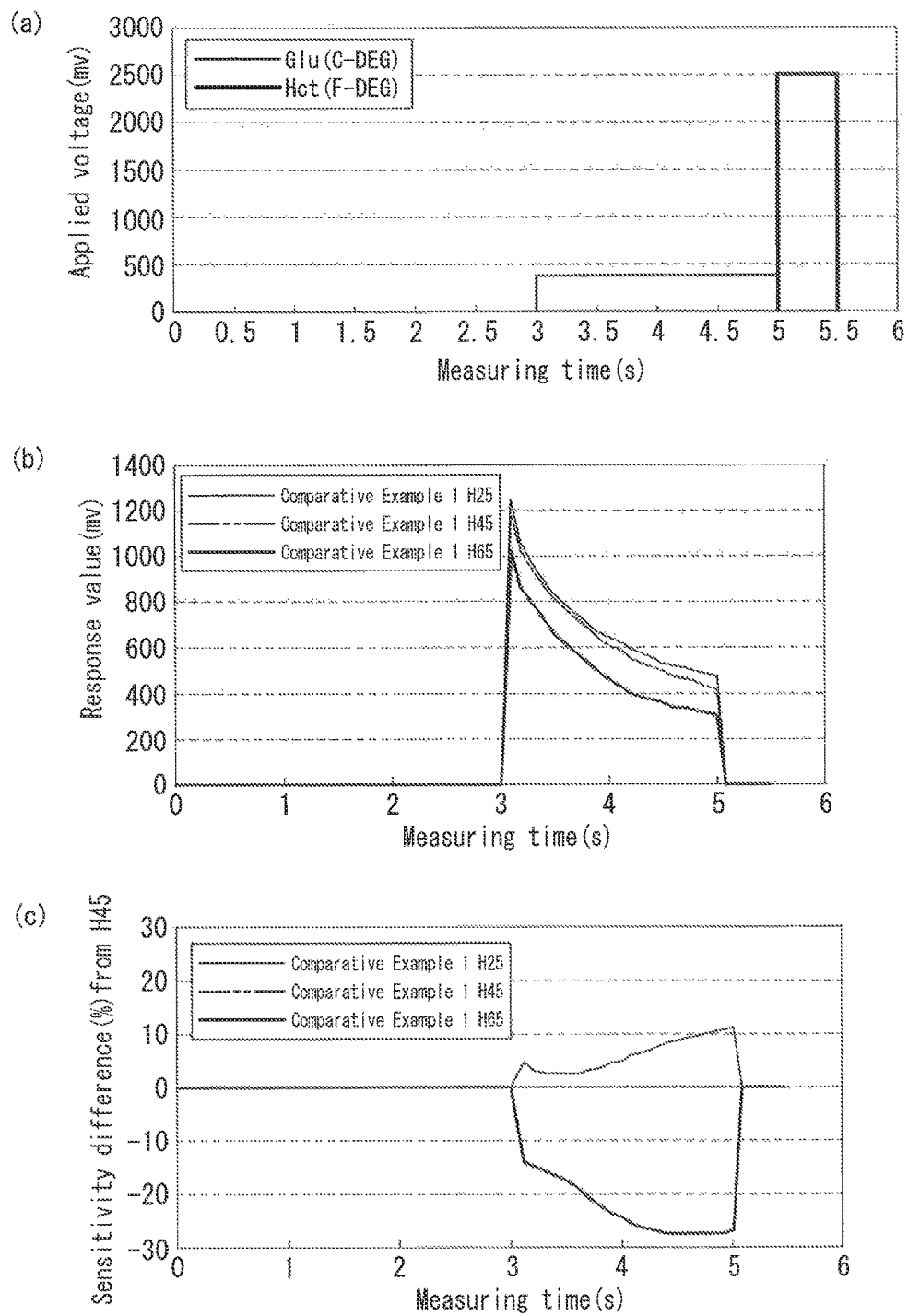
FIG. 32 shows the results of blood samples in which a blood component (glucose) concentration is 600 mg/dl.

FIG. 32 shows the results of the blood samples in which the blood component (glucose) concentration is 600 mg/dl. FIG. 32(*a*) is a graph showing the relationship between the application time and the applied current in Comparative Example 1. FIG. 32(*b*) is a graph showing changes in the response current value (mV) over time with respect to the applied voltage (mV) in Comparative Example 1. FIG. 32(*c*) is a graph showing changes in the sensitivity difference (%) over time with respect to the applied voltage (mV) in Comparative Example 1. Specifically, using the blood sample with an Hct value of 45% as a reference, a calibration curve is obtained from the correspondence between the first current value and the blood component (glucose) concentration. FIG. 32(*c*) shows the sensitivity difference (%) from the true value when the calibration curve is applied to the blood sample with an Hct value of 25% and the blood sample with an Hct value of 65%.

Compared to FIG. 32(*b*) and FIG. 32(*c*), in the measuring method of the present invention, as shown in FIG. 31(*b*) and FIG. 31(*c*), the sensitivity difference (%) after a measuring time of 4.5 seconds in FIG. 31(*b*) is smaller than the sensitivity difference (%) in FIG. 32(*b*). This can confirm that the effect of the Hct is reduced when the blood component amount is measured for each of the blood samples with different Hct values, and thus the accuracy of the measured blood component amount is improved.

In FIGS. 25 to 32, "H25" represents the use of the blood sample with an Hct value of 25%, "H45" represents the use of the blood sample with an Hct value of 45%, and "H65" represents the use of the blood sample with an Hct value of 65%.

Figure 33:
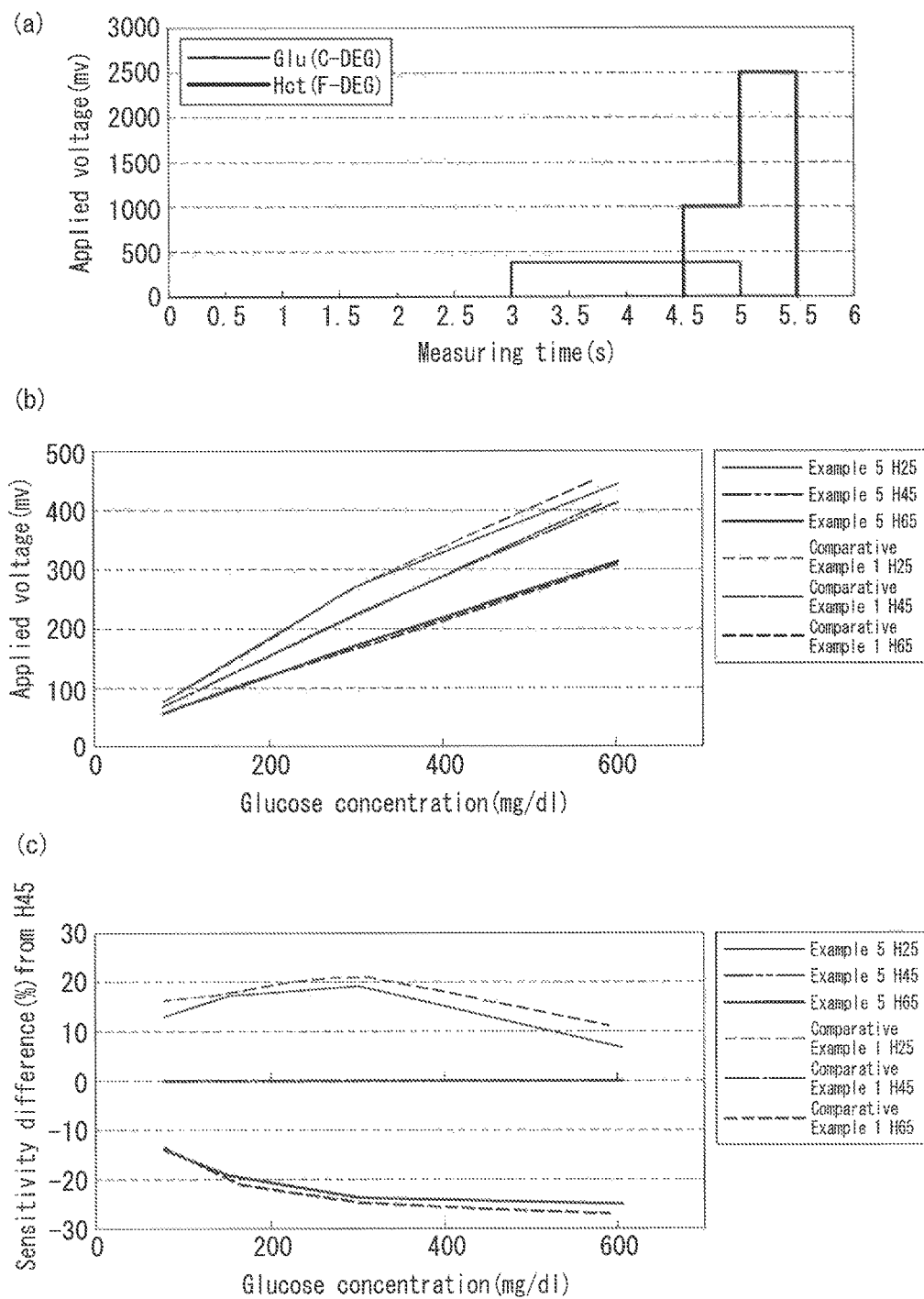
FIG. 33 is a summary of the results shown in FIGS. 25, 27, 29, and 31.

FIG. 33 is a summary of the results shown in FIGS. 25, 27, 29, and 31. FIG. 33(*a*) is a graph showing the relationship between the application time and the applied current. FIG. 33(*b*) is a graph showing changes in the blood component (glucose) concentration and the response current value (mV) over time when the application time is 5 seconds in Example 5. FIG. 33(*c*) is a graph showing the blood component (glucose) concentration and the sensitivity difference (%) when the application time is 5 seconds in Example 5.

As shown in FIGS. 33(*a*) to 33(*c*), in the measuring method of the present invention, the absolute value of the sensitivity difference (%) in Example 5 is small compared to the sensitivity difference (%) in Comparative Example in FIG. 33(*c*). This can confirm that the effect of the Hct is reduced when the blood component amount is measured for each of the blood samples with different Hct values, and thus the accuracy of the measured blood component amount is improved.

Figure 34:
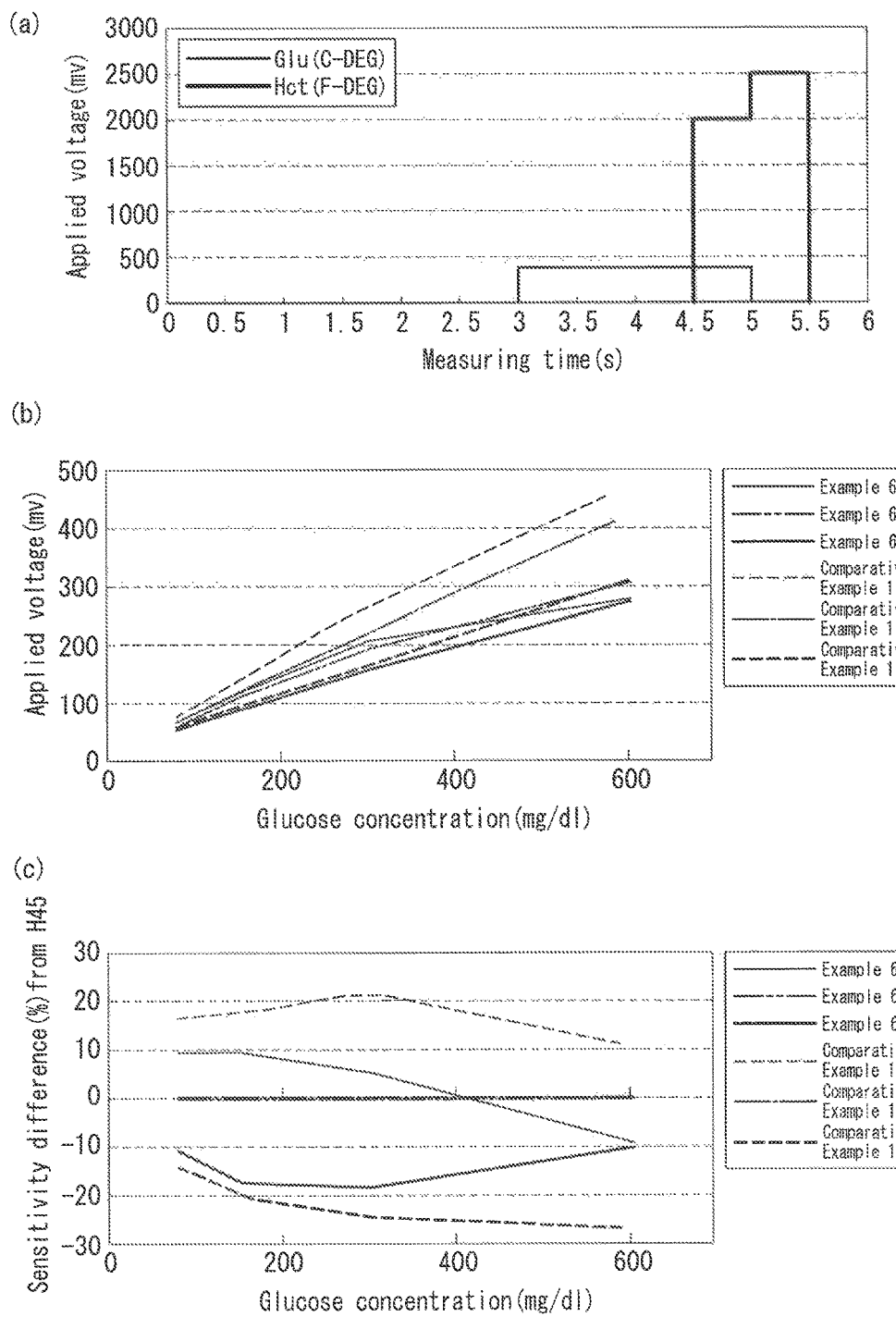
FIG. 34 is a summary of the results shown in FIGS. 26, 28, and 30.

FIG. 34 is a summary of the results shown in FIGS. 26, 28, and 30. FIG. 34(*a*) is a graph showing the relationship between the application time and the applied current. FIG. 34(*b*) is a graph showing changes in the blood component (glucose) concentration and the response current value (mV) over time when the application time is 5 seconds in Example 6. FIG. 34(*c*) is a graph showing the blood component (glucose) concentration and the sensitivity difference (%) when the application time is 5 seconds in Example 6.

As shown in FIGS. 34(*a*) to 34(*c*), in the measuring method of the present invention, the absolute value of the sensitivity difference (%) in Example 6 is small compared to the sensitivity difference (%) in Comparative Example in FIG. 34(*c*). This can confirm that the effect of the Hct is reduced when the blood component amount is measured for each of the blood samples with different Hct values, and thus the accuracy of the measured blood component amount is improved.

EXAMPLE 7

Figure 35:
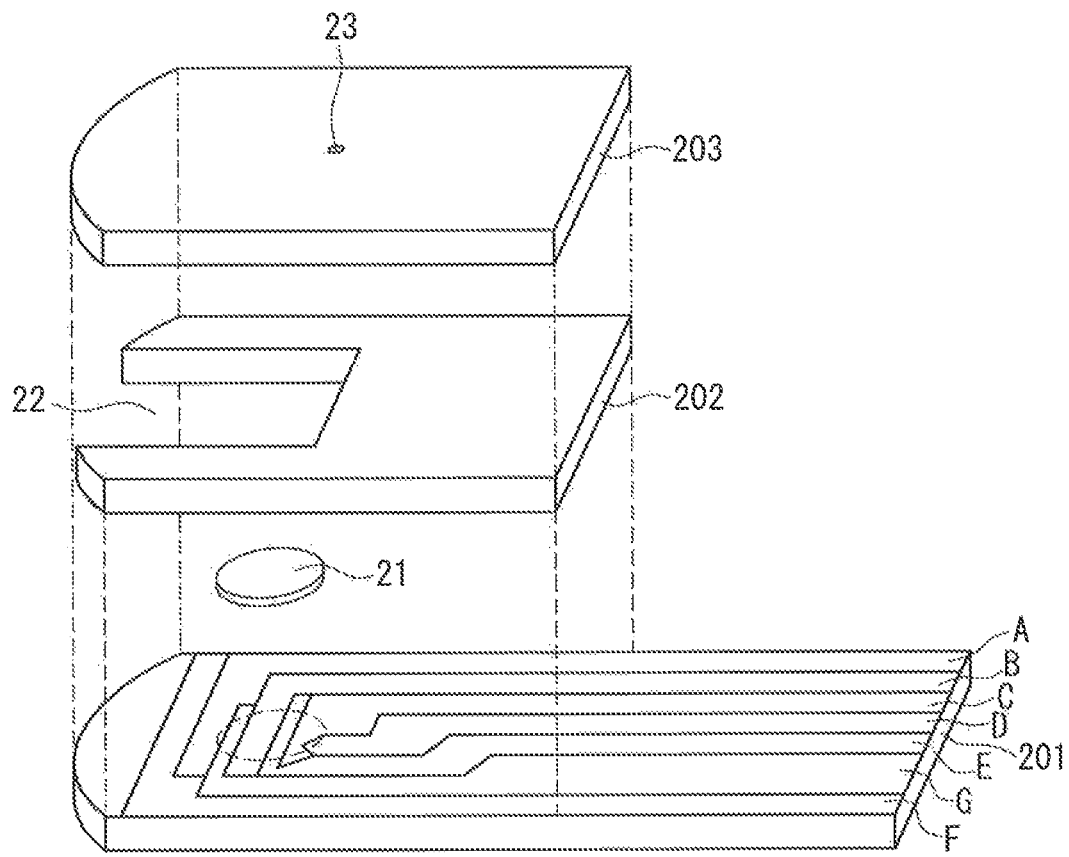
FIG. 35 is an exploded perspective view showing another example of a sensor of the present invention.
Figure 36:
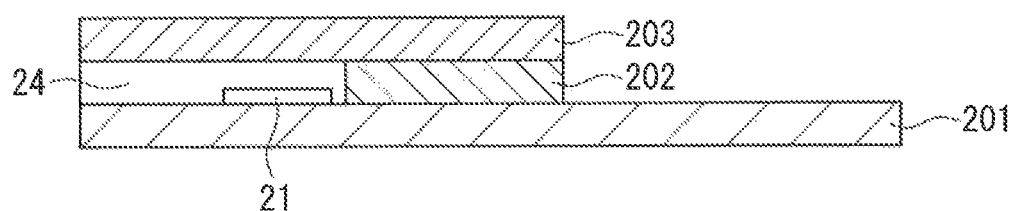
FIG. 36 is a cross-sectional view of the sensor in FIG. 35.
Figure 37:
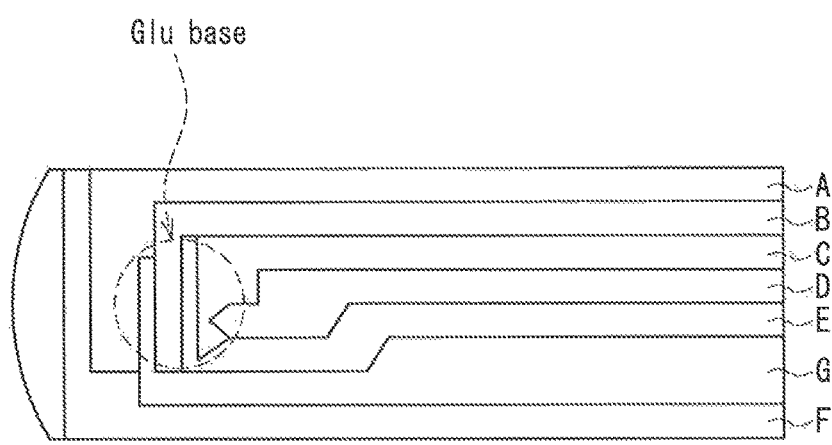
FIG. 37 is a plan view of the sensor in FIG. 35.

FIGS. 35, 36, and 37 show an example of a sensor for measuring blood components used in the measuring method of the present invention. FIG. 35 is an exploded perspective view of the sensor. FIG. 36 is a cross-sectional view of the sensor. FIG. 37 is a plan view of the sensor. In FIGS. 35, 36, and 37, the same portions are denoted by the same reference numerals.

As shown in the drawings, the sensor includes an insulating substrate 201 and seven electrodes A, B, C, D, E, G, and F formed on the insulating substrate 201. These electrodes can switch between the working electrode and the counter electrode. The surfaces of the electrodes A, B, C, D, E, F, and G are coated with a polymeric material such as CMC. A reagent layer 21 is arranged to cover a part of the electrodes A, B, C, D, E, and G. The reagent layer 21 includes an oxidoreductase such as glucose dehydrogenase and a mediator such as potassium ferricyanide, and may include, e.g., an enzyme stabilizer and a crystal homogenizing agent as optional components. A cover 203 is disposed on the insulating substrate 201 via a spacer 202, while leaving one end of the sensor (i.e., the right end in the drawings) uncovered. In the sensor, a flow path 24 is formed by the insulating substrate 201, the spacer 202, and the cover 203 to introduce blood into each of the electrodes (A, B, C, D, E, F, and G). The end of the flow path 24 extends to the other end of the sensor (i.e., the left end in the drawings) and is open to the outside, thereby serving as a blood inlet 22. Each of the seven electrodes (A, B, C, D, E, F, and G) is connected to a lead, and the leads extend to the one end of the sensor (i.e., the right end in the drawings). The ends of the leads are exposed and not covered with the cover. The cover 203 has an air hole 23 in a portion corresponding to the right end of the flow path 24.

In the present invention, the material of the insulating substrate is not particularly limited and may be, e.g., polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylate resin (PMMA), ABS resin (ABS), or glass. In particular, polyethylene terephthalate (PET), polycarbonate (PC), and polyimide (PI) are preferred, and polyethylene terephthalate (PET) is more preferred. The size of the insulating substrate is not particularly limited. For example, the insulating substrate has a total length of 5 to 100 mm, a width of 2 to 50 mm, and a thickness of 0.05 to 2 mm, preferably has a total length of 7 to 50 mm, a width of 3 to 20 mm, and a thickness of 0.1 to 1 mm, and more preferably has a total length of 10 to 30 mm, a width of 3 to 10 mm, and a thickness of 0.1 to 0.6 mm. The material and size of the insulating substrate are the same as in Examples 8 to 9, as will be described later.

The electrodes and the leads on the insulating substrate can be provided, e.g., by forming a conductive layer by sputtering or evaporation with the use of a material such as gold, platinum, or palladium, and processing the conductive layer into a particular electrode pattern with a laser. The laser may be, e.g., a YAG laser, a $CO_2$ laser, or an excimer laser. This process also is the same as in Examples 8 to 9, as will be described later.

The reagent layer 21 is formed in the following manner. For example, an aqueous solution containing 0.1 to 5 U per sensor of glucose dehydrogenase, 10 to 200 mM of potassium ferricyanide, 1 to 50 mM of maltitol, and 20 to 200 mM of taurine is dropped onto a circular slit portion 30 (not shown) and dried. The presence of the slit portion 30 can suppress the spread of the dropped aqueous solution, so that the reagent layer 21 can be located in a more accurate position. Thus, the reagent layer 21 is formed to cover a part of the electrodes A, B, C, D, E, and G. The drying process may be, e.g., natural drying or hot-air forced drying. However, if the temperature is too high, the enzyme can be inactivated. Therefore, the hot air of about 50° C. is preferably used.

In the present invention, the material of the spacer is not particularly limited and may be, e.g., the same as that of the insulating substrate. The size of the spacer is not particularly limited. For example, the spacer has a total length of 5 to 100 mm, a width of 2 to 50 mm, and a thickness of 0.01 to 1 mm, preferably has a total length of 7 to 50 mm, a width of 3 to 20 mm, and a thickness of 0.05 to 0.5 mm, and more preferably has a total length of 10 to 30 mm, a width of 3 to 10 mm, and a thickness of 0.05 to 0.25 mm. The spacer in this example has an I-shaped notch that serves as a flow path for the introduction of blood. For example, the I-shaped notch has a total length of 0.5 to 8 mm and a width of 0.1 to 5 mm, preferably has a total length of 1 to 10 mm and a width of 0.2 to 3 mm, and more preferably has a total length of 1 to 5 mm and a width of 0.5 to 2 mm. The notch may be formed, e.g., by punching through the spacer with a laser or drill, or by using a die that allows a notch to be provided during the formation of the spacer. The material, size, and notch of the spacer are the same as in Examples 8 to 9, as will be described later.

In the present invention, the material of the cover is not particularly limited and may be, e.g., the same as that of the insulating substrate. It is more preferable that a portion of the cover that forms the ceiling of the flow path for the introduction of blood is subjected to a hydrophilic treatment. The hydrophilic treatment may be, e.g., a method for applying a surface active agent or a method for introducing a hydrophilic functional group such as a hydroxyl group, a carbonyl group, or a carboxyl group into the surface of the cover by plasma processing. Alternatively, a layer of a surface active agent such as lecithin may be formed on the reagent layer. The size of the cover is not particularly limited. For example, the cover has a total length of 5 to 100 mm, a width of 3 to 50 mm, and a thickness of 0.01 to 0.5 mm, preferably has a total length of 10 to 50 mm, a width of 3 to 20 mm, and a thickness of 0.05 to 0.25 mm, and more preferably has a total length of 15 to 30 mm, a width of 5 to 10 mm, and a thickness of 0.05 to 0.1 mm. The cover preferably has an air hole, e.g., in the form of a circle, ellipse, or polygon. For example, the air hole has a maximum diameter of 0.01 to 10 mm, preferably has a maximum diameter of 0.05 to 5 mm, and more preferably has a maximum diameter of 0.1 to 2 mm. The air hole may be formed, e.g., by punching through the cover with a laser or drill, or by using a die that allows an air vent to be provided during the formation of the cover. The material, size, and air hole of the cover are the same as in Examples 8 to 9, as will be described later.

The insulating substrate, the spacer, and the cover are laminated in this order and integrated into one component, thereby producing the sensor. For the integration, the three members are joined together, e.g., using an adhesive or a heat seal. Examples of the adhesive include an epoxy adhesive, an acrylic adhesive, a polyurethane adhesive, a thermosetting adhesive (such as a hot-melt adhesive), and a UV curable adhesive. This process also is the same as in Examples 8 to 9, as will be described later.

A blood component amount, e.g., a blood glucose level is measured with the above sensor in the following manner. First, a special-purpose lancet is used to prick the finger tip or the like and draw a small amount of blood. On the other hand, the sensor is set in a special-purpose measuring device (meter). The blood is brought into contact with the blood inlet of the sensor set in the measuring device, and then is introduced into the sensor by capillary action. Analysis of the blood by the sensor is performed in the following steps.

In this measuring method, the electrode B is used as the working electrode of the first electrode system, the electrode E and the electrode G are used as the counter electrode of the first electrode system, the electrode F is used as the working electrode of the second electrode system, and the electrode A, the electrode C, and the electrode D are used as the counter electrode of the second electrode system.

(Step 1: Detection of Sample (Blood))

A voltage is applied between the electrode D and the electrode E, and the introduction of the blood is detected by a change in a current value due to the blood introduced into the sensor. After confirming the introduction of the blood, the next step is started. In the step 1, the applied voltage is, e.g., 0.05 to 1 V, and glucose in the blood reacts with the glucose oxidoreductase for a certain period of time.

(Step 2: Measurement of Apparent Amount of Glucose)

After glucose in the blood reacts with the glucose oxidoreductase for a certain period of time, a first voltage is applied to both of the electrodes of the first electrode system (i.e., the working electrode including the electrode B and the counter electrode including the electrode E and the electrode G), and a second voltage is applied to both of the electrodes of the second electrode system (i.e., the working electrode including the electrode F and the counter electrode including the electrode A, the electrode C, and the electrode D) (the first step). As described above, the reagent layer 21 is formed to cover a part of the electrode portion composed of the electrode A (the counter electrode of the second electrode system), the electrode B (the working electrode of the first electrode system), the electrode C (the counter electrode of the second electrode system), the electrode D (the counter electrode of the second electrode system), the electrode E (the counter electrode of the first electrode system), and the electrode G (the counter electrode of the first electrode system) of the biosensor. The reduced mediator that is generated on the electrode C of the first electrode system by the enzyme reaction is oxidized, and an oxidation current (a first current value) is detected. Based on the oxidation current (the first current value), an apparent amount of glucose (an apparent blood component amount) in the blood is calculated. The application time of the first voltage is the same as that of the second voltage. The reaction time between the glucose and the oxidoreductase may be, e.g., 0 to 60 seconds, preferably 0 to 30 seconds, and more preferably 0 to 10 seconds. The first voltage in the step 2 (the first step) may be, e.g., 0.05 to 1.0 V, preferably 0.1 to 0.8 V, and more preferably 0.2 to 0.6 V. The application time of the first voltage may be, e.g., 0.05 to 30 seconds, preferably 0.1 to 10 seconds, and more preferably 0.5 to 5 seconds. The second voltage in the step 2 (the first step) may be, e.g., 0.5 to 5 V, preferably 1 to 3 V, and more preferably 1.5 to 2.5 V. The application time of the second voltage may be, e.g., 0.01 to 5 seconds, preferably 0.01 to 2.5 seconds, and more preferably 0.1 to 1 second.

The combinations of the first voltage and the second voltage in the step 2 (the first step) may include the following. For example, the first voltage is 0.05 to 1 V and the application time of the first voltage is 0.05 to 30 seconds, and the second voltage is 0.5 to 5 V and the application time of the second voltage is 0.01 to 5 seconds. Preferably, the first voltage is 0.01 to 0.8 V and the application time of the first voltage is 0.1 to 10 seconds, and the second voltage is 1 to 3 V and the application time of the second voltage is 0.01 to 2.5 seconds. More preferably, the first voltage is 0.2 to 0.6 V and the application time of the first voltage is 0.5 to 5 seconds, and the second voltage is 1.5 to 2.5 V and the application time of the second voltage is 0.1 to 1 second.

The measuring method may include a previous step of applying the first voltage only to the first electrode system before the first voltage is applied to both of the electrodes of the first electrode system and the second voltage is applied to both of the electrodes of the second electrode system in the step 2 (the first step). The first voltage in the previous step may be, e.g., 0.05 to 1.0 V, preferably 0.1 to 0.8 V, and more preferably 0.2 to 0.6 V. The application time of the first voltage in the previous step may be, e.g., 0.05 to 30 seconds, preferably 0.1 to 10 seconds, and more preferably 0.5 to 5 seconds.

The second voltage and the application time of the second voltage may be selected based on the first current value obtained in the step 2 (the first step). Specifically, when the first current value is 0.01 to 0.1 V, the second voltage may be 1.5 to 2.0 V and the application time of the second voltage may be 0.1 to 1 second. When the first current value is 0.1 to 1 V, the second voltage may be 2.0 to 2.5 V and the application time of the second voltage may be 0.1 to 1 second.

Before the first step, the first voltage may be applied only to the first electrode system to detect a third current value that flows through the first electrode system, and the second voltage and the application time of the second voltage may be selected by the first current value obtained in the step 2, based on the third current value. In this case, the first voltage may be, e.g., 0.05 to 1.0 V, preferably 0.1 to 0.8 V, and more preferably 0.2 to 0.6 V. The application time of the first voltage may be, e.g., 0.05 to 30 seconds, preferably 0.1 to 10 seconds, and more preferably 0.5 to 5 seconds. Specifically, when the third current value is 0.01 to 0.1 V, the second voltage may be 1.5 to 2 V and the application time of the second voltage may be 0.1 to 1 second. When the third current value is 0.1 to 1 V, the second voltage may be 2.0 to 2.5 V and the application time of the third voltage may be 0.1 to 1 second.

(Step 3: Measurement of Hct Value)

The application of the first voltage to the first electrode system is stopped, and a third voltage is applied to both of the electrodes of the second electrode system (i.e., the working electrode including the electrode F and the counter electrode including the electrode A, the electrode C, and the electrode D), so that a current (a second current value) that depends on an Hct value based on the electrolytic oxidation reaction of glucose can be detected (the second step). The conversion from the detected current (the second current value) to an Hct value can be performed by previously determining the calibration curve or the calibration table. This correction may use the Hct value obtained from the calibration curve of the current and the Hct value, which has been previously prepared, or may use the detected current directly. The third voltage in the step 3 (the second step) may be, e.g., 0.1 to 10 V, preferably 0.1 to 6.5 V, and more preferably 0.5 to 2.5 V. The application time of the third voltage may be, e.g., 0.05 to 10 seconds, preferably 0.1 to 5 seconds, and more preferably 0.2 to 1 second. In the step 3, the mediator is not arranged on the electrode F (the working electrode). Moreover, there is a predetermined gap between the electrodes C, D and the electrode F, and no reagent such as a mediator is arranged, but only blood is present in this gap. Therefore, an oxidation current that depends on the Hct value can be detected without being affected by the reagent. Even if the surface of the electrode F is not coated with a polymeric material or the like, the measurement can be performed. The step 3 (the second step) may be performed either immediately after the step 2 (the first step) or after a time interval from the step 2 (the first step). The time interval may be, e.g., 0 to 10 seconds, preferably 0.05 to 5 seconds, and more preferably 0.1 to 1 second. The third voltage in the step 3 may be either the same as or different from the second voltage in the step 2.

The third voltage and the application time of the third voltage may be selected based on the first current value obtained in the step 2. Specifically, when the first current value is 0.01 to 0.1 V, the third voltage may be 2 to 2.5 V and the application time of the third voltage may be 0.2 to 1 second. When the first current value is 0.1 to 1 V, the third voltage may be 2.5 to 3 V and the application time of the third voltage may be 0.2 to 1 second.

Before the first step, the first voltage may be applied to the first electrode system to detect a third current value that flows through the first electrode system, and the third voltage and the application time of the third voltage may be selected by the first current value obtained in the step 2, based on the third current value. Specifically, when the first current value is 0.01 to 0.1 V, the third voltage may be 2 to 2.5 V and the application time of the third voltage may be 0.2 to 1 second. When the third current value is 0.1 to 1 V, the third voltage may be 2.5 to 2 V and the application time of the third voltage may be 0.1 to 1 second.

(Step 4: Correction of Blood Component)

The amount of glucose obtained in the step 2 (the first step) is corrected with the Hct value detected in the step 3 (the second step). This correction is preferably performed based on the calibration curve (including the calibration table) which has been previously prepared. The corrected amount of glucose is displayed or stored in the measuring device. Instead of correcting the amount of glucose after the Hct value has been determined, as described above, the amount of glucose may be corrected by directly using the current value (the second current value) that depends on the Hct value detected in the step 3 (the second step).

EXAMPLE 8

In this example, a sensor shown in FIGS. 35 to 37 is produced in the same manner as Example 7. Using the sensor that includes the electrode B as the working electrode of the first electrode system, the electrode E and the electrode G as the counter electrode of the first electrode system, the electrode F as the working electrode of the second electrode system, and the electrode A, the electrode C, and the electrode D as the counter electrode of the second electrode system, a response current and a sensitivity difference are determined by varying the blood component amount in blood. Moreover, as Comparative Example 2, using the same sensor that includes the electrode B as the working electrode of the first electrode system, the electrode E and the electrode G as the counter electrode of the first electrode system, the electrode F as the working electrode of the second electrode system, and the electrode A, the electrode C, and the electrode D as the counter electrode of the second electrode system, a response current and a sensitivity difference are determined by varying the blood component amount in blood. The measurement of a sample (blood) and a blood component (glucose) and the correction of the blood component are performed in the same manner as Example 7. The reagent layer is formed in the following manner. A reagent solution is prepared by dissolving glucose dehydrogenase, potassium ferricyanide (60 mM), and taurine (80 mM) in a CMC aqueous solution (0.1 wt %). Then, the reagent solution is dropped onto the electrodes and dried. The distance between the working electrode and the counter electrode is 0.1 mm or more. Three types of blood samples, in which the Hct values are adjusted to 25%, 45%, and 65%, respectively, are prepared for each glucose concentration. For the three blood samples, the sensor is used to measure a current flowing through both of the electrodes of the sensor and to determine a response current value and a sensitivity difference in the measurement of the Hct value under the following conditions: the first voltage is 400 mV and the application time of the first voltage is from 3 to 5 seconds; the second voltage is 2500 mV and the application time of the second voltage is from 4.5 to 5 seconds; and the third voltage is 2500 mV and the application time of the third voltage is from 5 to 5.5 seconds (see FIG. 39(a)). In FIG. 39(a), "Glu (B-EG)" represents the application of the voltage to the first electrode system, and "Hct (F-ACD)" represents the application of the voltage to the second electrode system. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds.

COMPARATIVE EXAMPLE 2

In Comparative Example 2, for the three blood samples, the sensor is used to measure a current flowing through both of the electrodes of the sensor and to determine a response current value and a sensitivity difference in the measurement of the Hct value under the following conditions: the first voltage is 400 mV and the application time of the first voltage is 3 to 5 seconds; and the second voltage is 2500 mV and the application time of the second voltage is 5 to 5.5 seconds (see FIG. 38(a)). In FIG. 38(a), "Glu (B-ACDEG)" represents the application of the voltage to the first electrode system, and "Hct (F-AF)" represents the application of the voltage to the second electrode system. As can be seen from FIG. 38(a), the voltage is applied to the first electrode system, and then the voltage is applied to the second electrode system. Unlike the step 2 of the present invention, the first voltage and the second voltage are not simultaneously applied to the first electrode system and the second electrode system, respectively.

EXAMPLE 9

In this example, a response current value and a sensitivity difference in the measurement of the Hct value are determined in the same manner as Example 8, except that using a sensor that includes the electrode B as the working electrode of the first electrode system, the electrode A, the electrode C, and the electrode D as the counter electrode of the first electrode system, the electrode F as the working electrode of the second electrode system, the electrode A and the electrode G as the counter electrode of the second electrode system, the electrode F as the working electrode of a third electrode system, and the electrode E as the counter electrode of the third electrode system, a current flowing through both of the electrodes of the sensor is measured under the following conditions: the first voltage is 400 mV and the application time of the first voltage is from 3 to 5 seconds; the second voltage is 2500 mV and the application time of the second voltage is from 4.5 to 5 seconds; and the third voltage is 2500 mV and the application time of the third voltage is from 5 to 5.5 seconds (see FIG. 40(a)). In FIG. 40(a), "Glu (B-ACD)" represents the application of the voltage to the first electrode system, "Hct (FAG)" represents the application of the voltage to the second electrode system, and "Hct (F-EG)" represents the application of the voltage to the third electrode system. In this case, the step 2 (the first step) corresponds to a measuring time from 4.5 to 5 seconds, and the step 3 (the second step) corresponds to a measuring time from 5 to 5.5 seconds. The previous step corresponds to a measuring time from 3 to 4.5 seconds. The reagent layer 21 is arranged to cover a part of the electrodes A, B, C, D, E, and G. In this example, the third voltage is applied to the third electrode system instead of applying the third voltage to the second electrode system in the second step.

Figure 38:
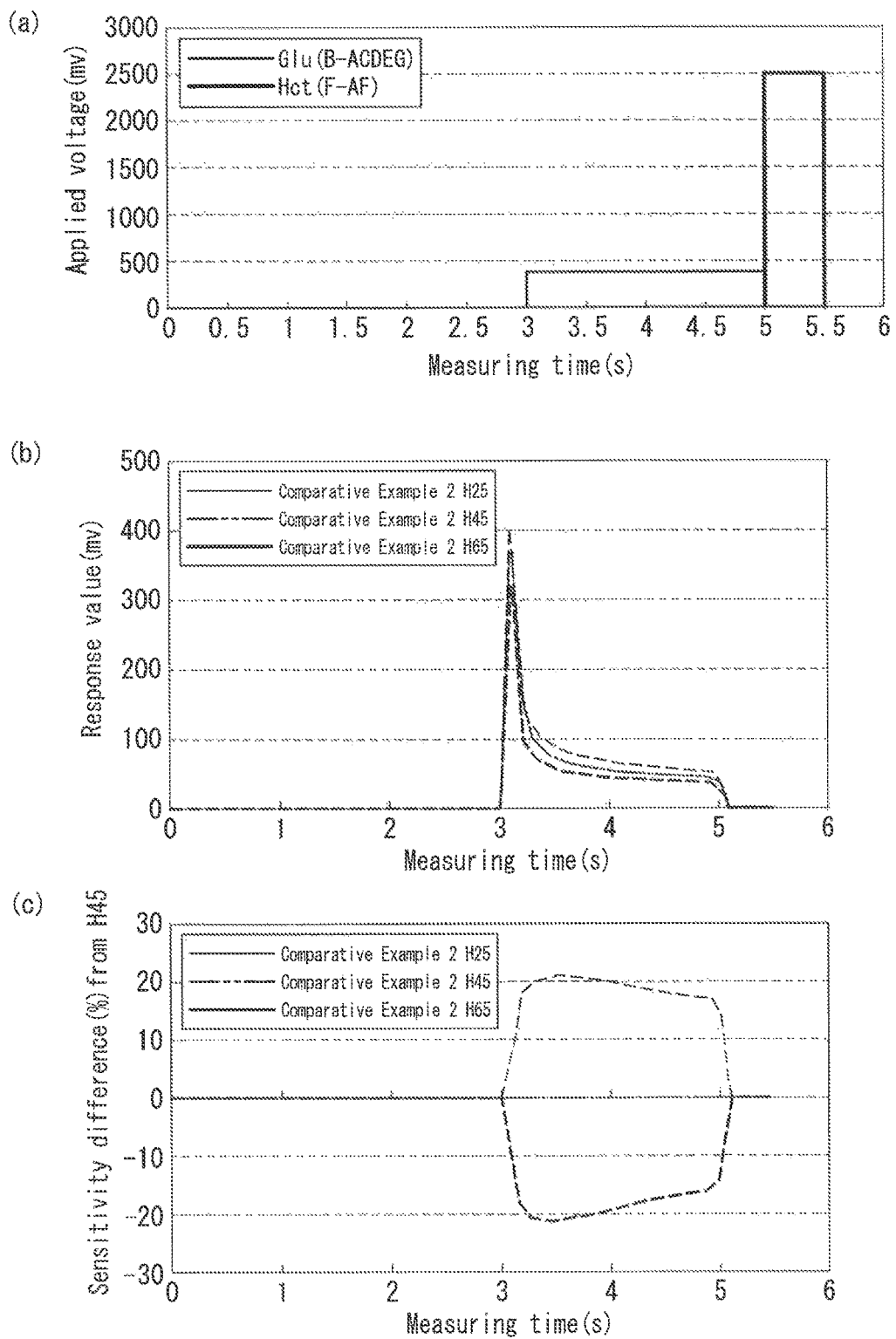
FIG. 38 shows the results of blood samples in which a blood component (glucose) concentration is 75 mg/dl.

FIG. 38 shows the results of the blood samples in which the blood component (glucose) concentration is 75 mg/dl. FIG. 38(a) is a graph showing the relationship between the application time and the applied current. FIG. 38(b) is a graph showing changes in the response current value (mV) over time with respect to the applied voltage (mV) in Comparative Example 2. FIG. 38(c) is a graph showing changes in the sensitivity difference (%) over time with respect to the applied voltage (mV) in Comparative Example 2. Specifically, using the blood sample with an Hct value of 45% as a reference, a calibration curve is obtained from the correspondence between the first current value and the blood component (glucose) concentration. FIG. 38(c) shows the sensitivity difference (%) from the true value when the calibration curve is applied to the blood sample with an Hct value of 25% and the blood sample with an Hct value of 65%.

Figure 39:
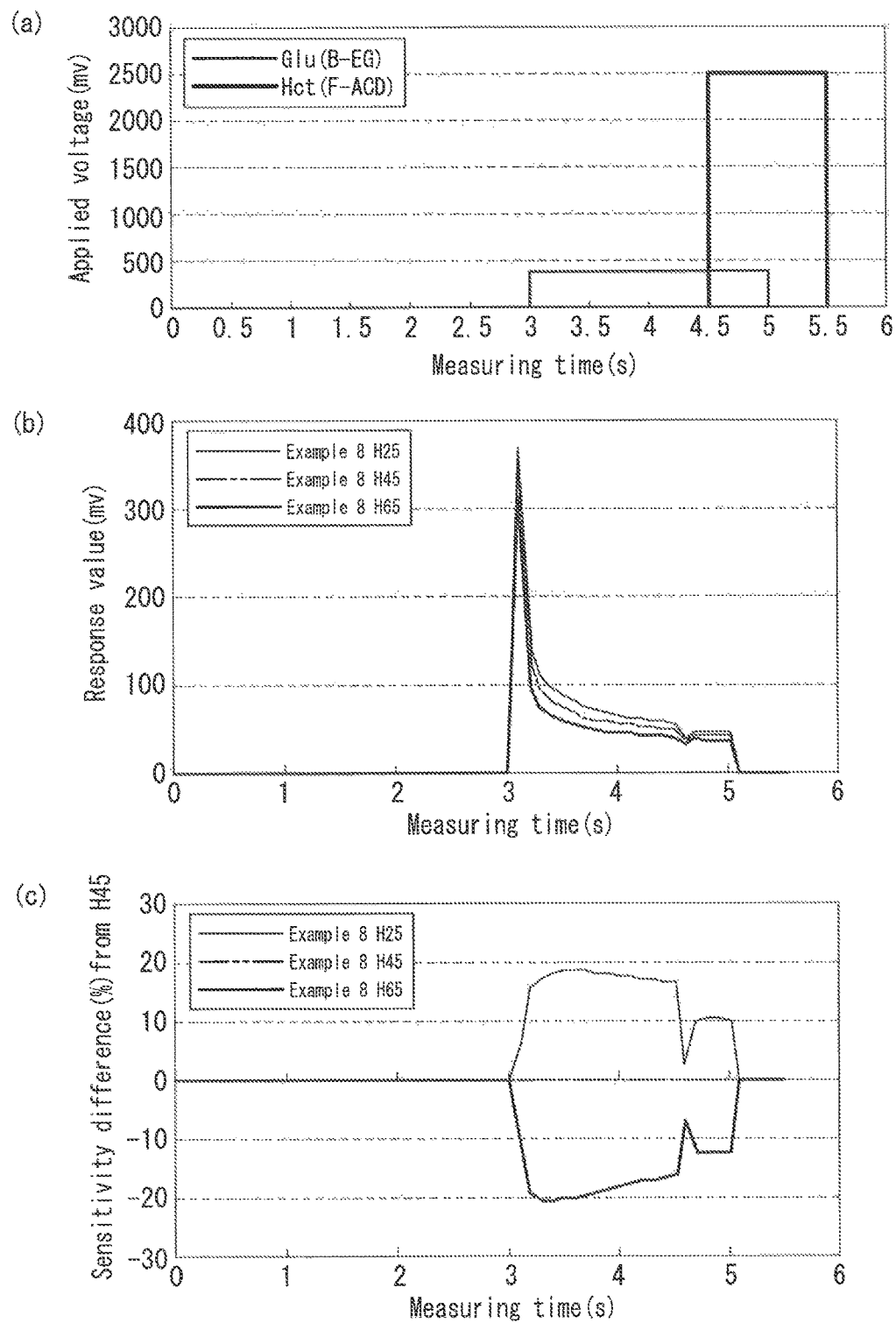
FIG. 39 shows the results of blood samples in which a blood component (glucose) concentration is 75 mg/dl.

FIG. 39 shows the results of the blood samples in which the blood component (glucose) concentration is 75 mg/dl. FIG. 39(a) is a graph showing the relationship between the application time and the applied current. FIG. 39(b) is a graph showing changes in the response current value (mV) over time with respect to the applied voltage (mV) in Example 8. FIG. 39(c) is a graph showing changes in the sensitivity difference (%) over time with respect to the applied voltage (mV) in Example 8. Specifically, using the blood sample with an Hct value of 45% as a reference, a calibration curve is obtained from the correspondence between the first current value and the blood component (glucose) concentration. FIG. 39(c) shows the sensitivity difference (%) from the true value when the calibration curve is applied to the blood sample with an Hct value of 25% and the blood sample with an Hct value of 65%.

Figure 40:
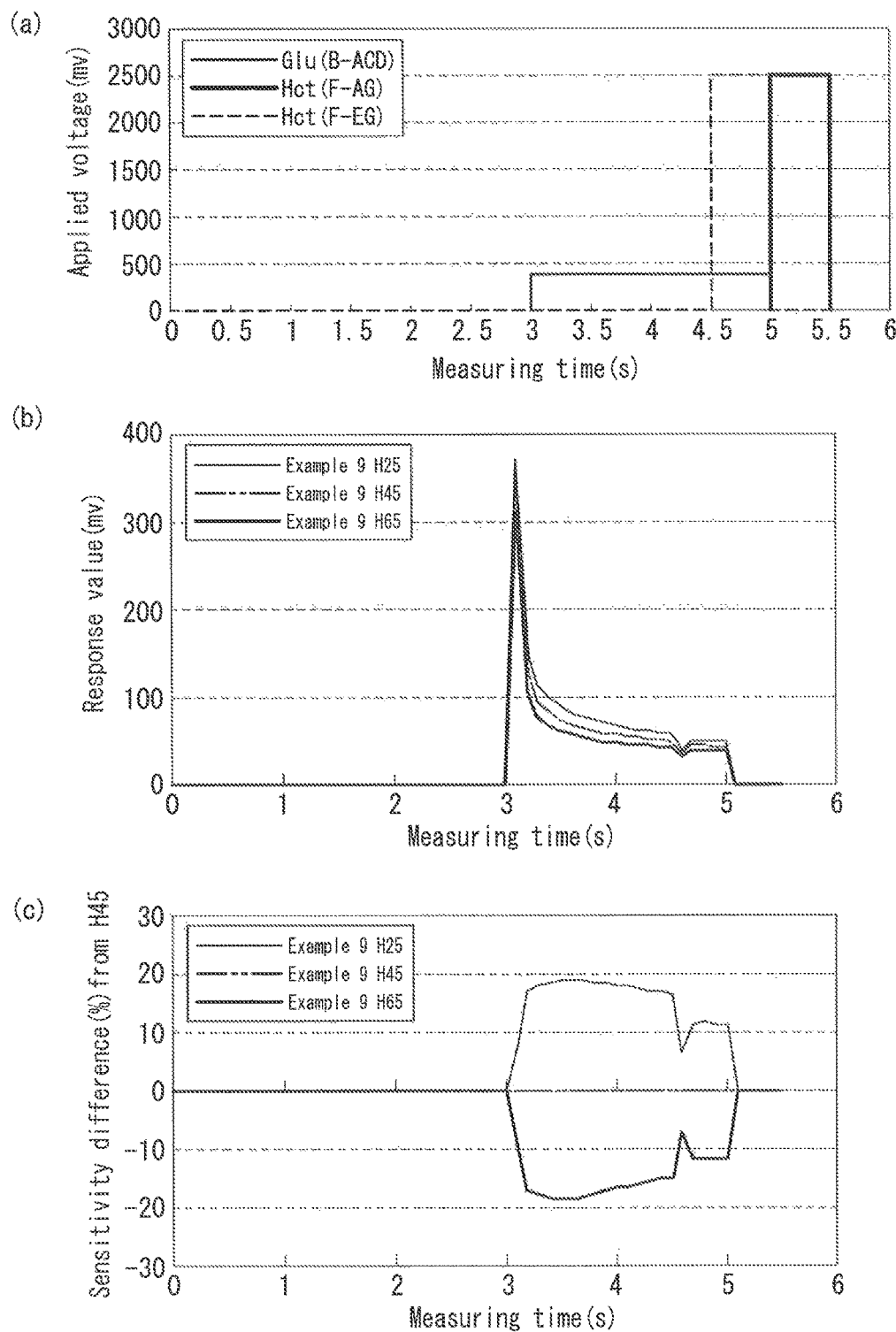
FIG. 40 shows the results of blood samples in which a blood component (glucose) concentration is 75 mg/dl.

FIG. 40 shows the results of the blood samples in which the blood component (glucose) concentration is 75 mg/dl. FIG. 40(a) is a graph showing the relationship between the application time and the applied current. FIG. 40(b) is a graph showing changes in the response current value (mV) over time with respect to the applied voltage (mV) in Example 9. FIG. 40(c) is a graph showing changes in the sensitivity difference (%) over time with respect to the applied voltage (mV) in Example 9. Specifically, using the blood sample with an Hct value of 45% as a reference, a calibration curve is obtained from the correspondence between the first current value and the blood component (glucose) concentration. FIG. 40(c) shows the sensitivity difference (%) from the true value when the calibration curve is applied to the blood sample with an Hct value of 25% and the blood sample with an Hct value of 65%. In FIGS. 39 to 40, "H25" represents the use of the blood sample with an Hct value of 25%, "H45" represents the use of the blood sample with an Hct value of 45%, and "H65" represents the use of the blood sample with an Hct value of 65%.

Compared to FIG. 38(b) and FIG. 38(c), in the measuring method of the present invention, as shown in FIG. 39(b) and FIG. 39(c), the sensitivity difference (%) after a measuring time of 4.5 seconds in FIG. 39(c) is smaller than the sensitivity difference (%) in FIG. 38(c). This can confirm that the effect of the Hct is reduced when the blood component amount is measured for each of the blood samples with different Hct values, and thus the accuracy of the measured blood component amount is improved. Moreover, compared to FIG. 38(b) and FIG. 38(c), in the measuring method of the present invention, as shown in FIG. 40(b) and FIG. 40(c), the sensitivity difference (%) after a measuring time of 4.5 seconds in FIG. 40(c) is smaller than the sensitivity difference (%) in FIG. 38(c). This can confirm that the effect of the Hct is reduced when the blood component amount is measured for each of the blood samples with different Hct values, and thus the accuracy of the measured blood component amount is improved.

Figure 41:
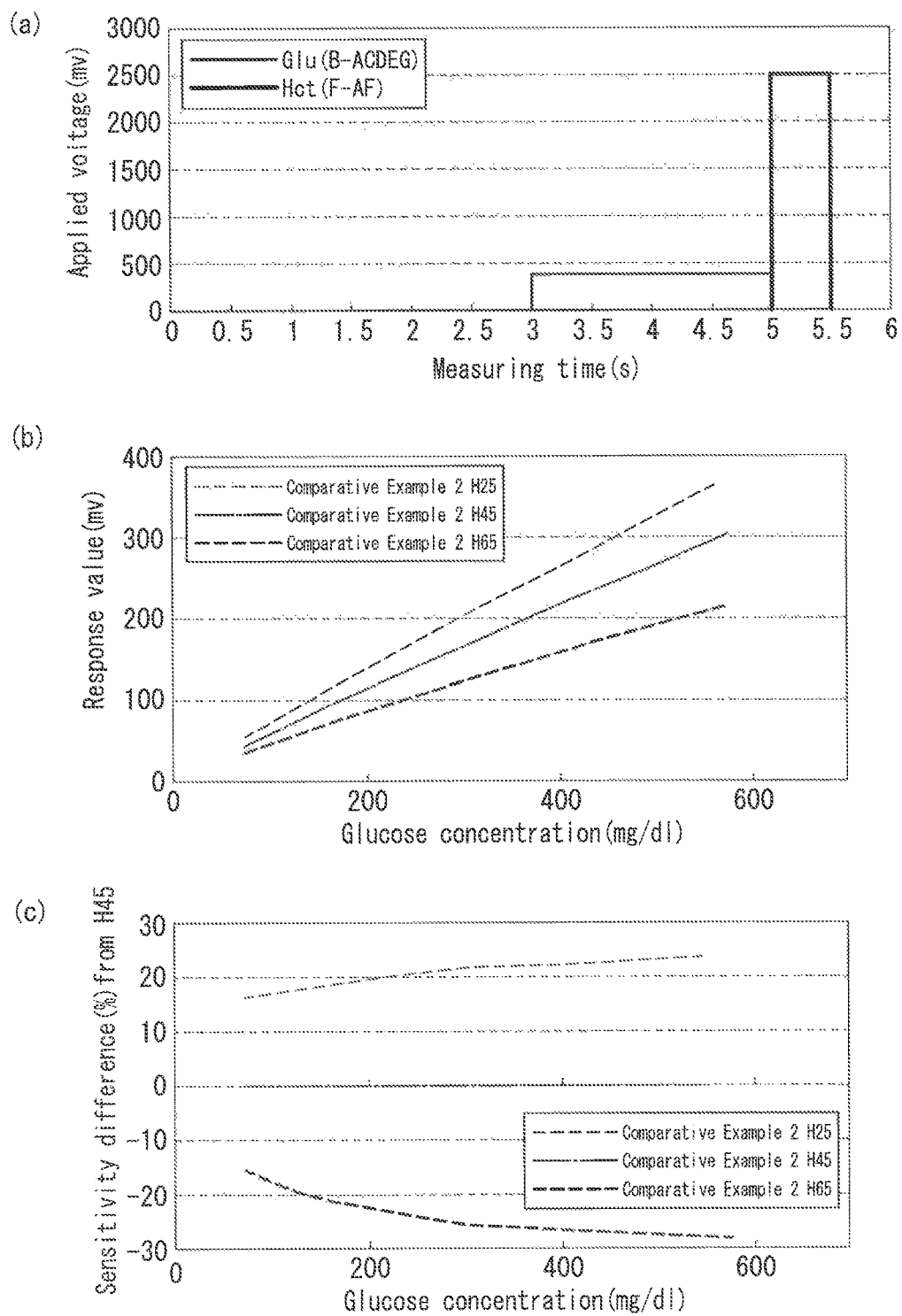
FIG. 41 is a summary of the results shown in FIG. 38.

FIG. 41 is a summary of the results shown in FIG. 38. FIG. 41(a) is a graph showing the relationship between the application time and the applied current. FIG. 41(b) is a graph showing changes in the blood component (glucose) concentration and the response current value (mV) over time when the application time is 5 seconds in Comparative Example 2. FIG. 41(c) is a graph showing the blood component (glucose) concentration and the sensitivity difference (%) when the application time is 5 seconds in Comparative Example 2.

Figure 42:
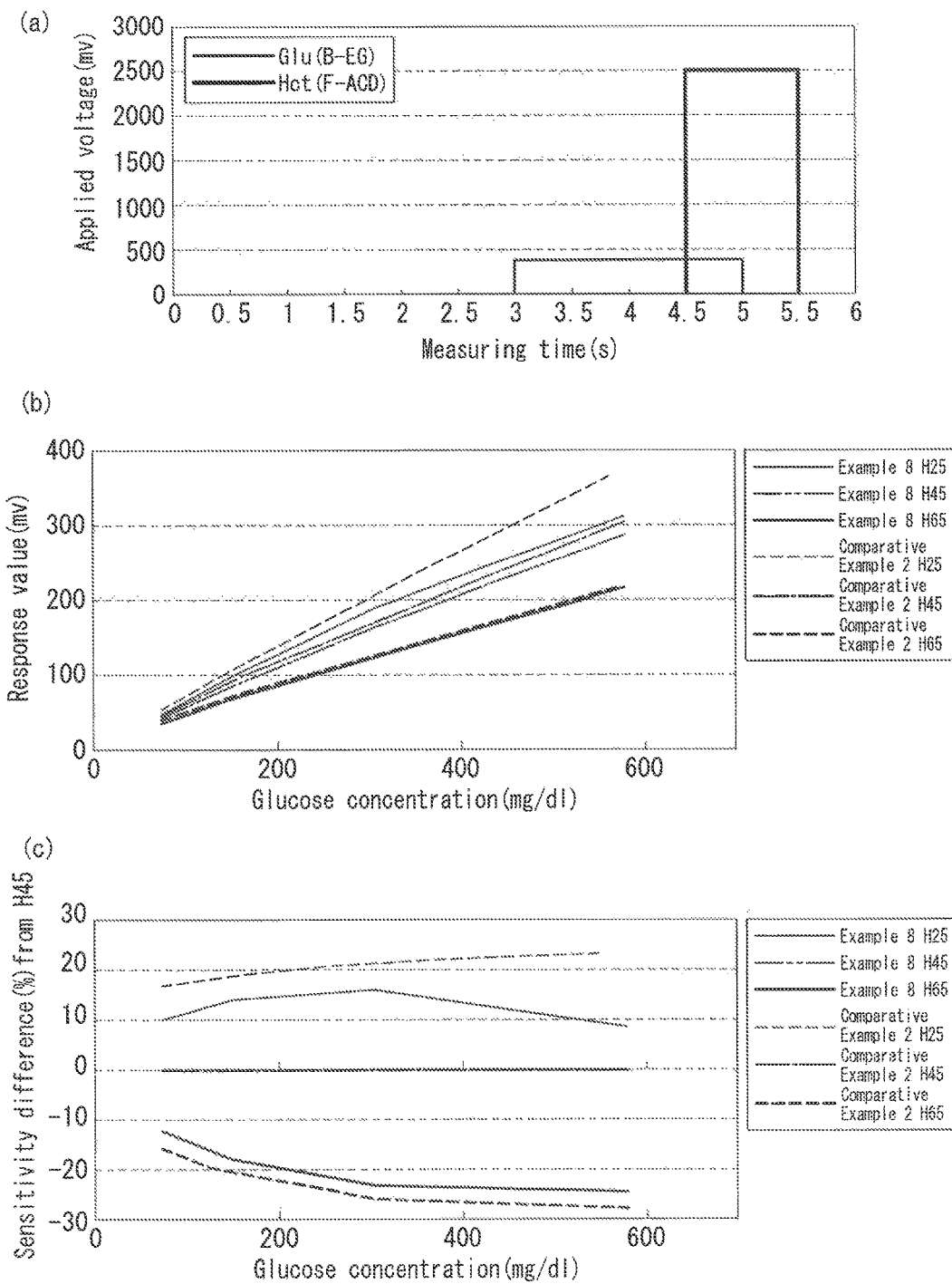
FIG. 42 is a summary of the results shown in FIG. 39.

FIG. 42 is a summary of the results shown in FIG. 39. FIG. 42(a) is a graph showing the relationship between the application time and the applied current. FIG. 42(b) is a graph showing changes in the blood component (glucose) concentration and the response current value (mV) over time when the application time is 5 seconds in Example 8. FIG. 42(c) is a graph showing the blood component (glucose) concentration and the sensitivity difference (%) when the application time is 5 seconds in Example 8.

As shown in FIGS. 42(a) to 42(c), in the measuring method of the present invention, the absolute value of the sensitivity difference (%) in Example 8 is small compared to the sensitivity difference (%) in Comparative Example 2 in FIG. 42(c). This can confirm that the effect of the Hct is reduced when the blood component amount is measured for each of the blood samples with different Hct values, and thus the accuracy of the measured blood component amount is improved.

Figure 43:
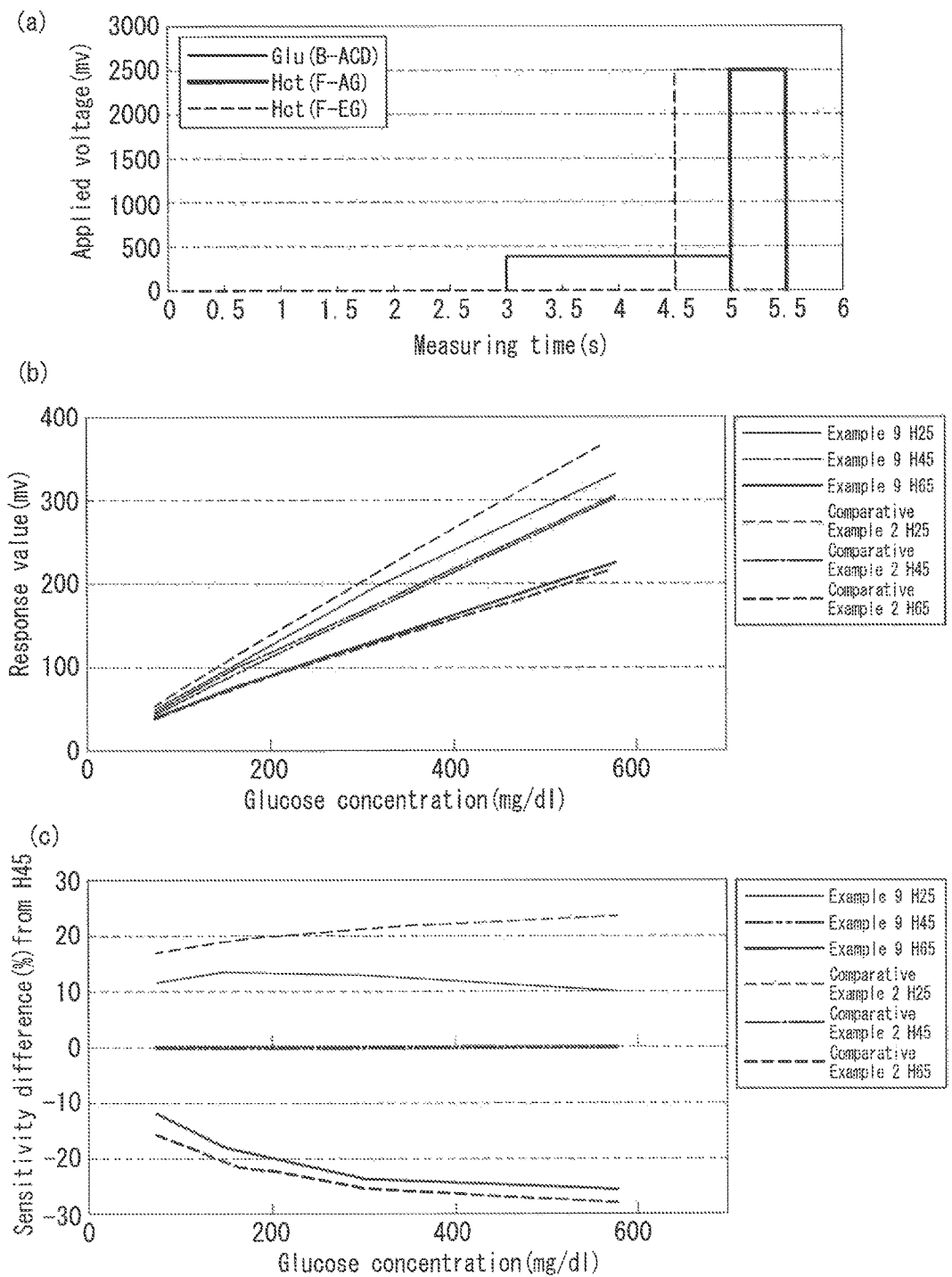
FIG. 43 is a summary of the results shown in FIG. 40.

FIG. 43 is a summary of the results shown in FIG. 40. FIG. 43(a) is a graph showing the relationship between the application time and the applied current. FIG. 43(b) is a graph showing changes in the blood component (glucose) concentration and the response current value (mV) over time when the application time is 5 seconds in Example 9. FIG. 43(c) is a graph showing the blood component (glucose) concentration and the sensitivity difference (%) when the application time is 5 seconds in Example 9.

As shown in FIGS. 43(a) to 43(c), in the measuring method of the present invention, the absolute value of the sensitivity difference (%) in Example 8 is small compared to the sensitivity difference (%) in Comparative Example 2 in FIG. 43(c). This can confirm that the effect of the Hct is reduced when the blood component amount is measured for each of the blood samples with different Hct values, and thus the accuracy of the measured blood component amount is improved.

INDUSTRIAL APPLICABILITY

As described above, the method for measuring a blood component amount of the present invention reduces the effect of Hct, and thus improves the accuracy of the measured blood component amount. Therefore, the measuring method of the present invention can be preferably used in all fields that require the measurement of blood components such as biology, biochemistry, and medicine. In particular, the measuring method of the present invention is suitable for the field of clinical examination.

DESCRIPTION OF REFERENCE NUMERALS

A Electrode A
B Electrode B
C Electrode C
D Electrode D
E Electrode E
F Electrode F
G Electrode G
11, 12 Reagent layer
12, 22 Blood inlet
13, 23 Air hole
14, 24 Flow path
101, 201 Insulating substrate
102, 202 Spacer
103, 203 Cover
1 Sensor
2 Measuring device
4 Display unit
5 Insertion port
6 Input terminal portion
12 Sample inlet
30 A/D converter
31 Determination portion
32 Display portion
33 Power source
34 Memory
35 Clock
36 Correction portion
37 Voltage application portion
38 Current-voltage converter
39 Control portion

The invention claimed is:
1. A method for measuring a blood component amount that uses a biosensor to calculate a blood component amount in blood,
the biosensor comprising:
a first electrode system having a first working electrode and a first counter electrode;

a second electrode system having a second working electrode and a second counter electrode; and a reagent portion arranged in a form that covers at least a part of the first electrode system, but does not cover the second working electrode, the method comprising:

a preliminary step of applying a first voltage to the first electrode system;

a first step of detecting a first current value that flows through the first electrode system and calculating an apparent blood component amount in the blood based on the first current value, during a period in which the first voltage is applied to the first electrode system and a second voltage is applied to the second electrode system while the first voltage is being applied, after the previous step;

following the first step, a second step of stopping the application of the first voltage to the first electrode system and the second voltage to the second electrode system, applying a third voltage to the second electrode system, and detecting a second current value that depends on a hematocrit value; and a step of calculating a true blood component amount using the apparent blood component amount and the second current value.

2. The method for measuring a blood component amount according to claim 1, wherein the second voltage and the third voltage are equal.

3. The method for measuring a blood component amount according to claim 1, wherein the second voltage and the third voltage are different.

4. The method for measuring a blood component amount according to claim 1, wherein the first current value is detected at an end of the period in which the first voltage is applied to the first electrode system and the second voltage is applied to the second electrode system while the first voltage is being applied.

5. The method for measuring a blood component amount according to claim 1, wherein the biosensor further comprises a third electrode system having a third working electrode and a third counter electrode, the reagent portion is arranged in a form that also covers at least a part of the third counter electrode, but does not cover the third working electrode, and the third voltage is applied to the third electrode system instead of applying the third voltage to the second electrode system in the second step.

6. The method for measuring a blood component amount according to claim 1, wherein the first electrode system is independent of the counter electrode of the second electrode system.

7. The method for measuring a blood component amount according to claim 1, wherein the first step and the second step are performed with a time interval between them.

8. The method for measuring a blood component amount according to claim 7, wherein the time interval is 0.01 to 10 seconds.

9. The method for measuring a blood component amount according to claim 1, wherein the second voltage is 0.5 to 5 V.

10. The method for measuring a blood component amount according to claim 1, wherein the third voltage is 0.1 to 10 V.

11. The method for measuring a blood component amount according to claim 1, wherein the first voltage is 0.05 to 1 V and an application time of the first voltage is 0.05 to 30 seconds, and the second voltage is 0.5 to 5 V and an application time of the second voltage is 0.01 to 5 seconds.

* * * * *